US012703637B2

(12) United States Patent
Turker et al.

(10) Patent No.: US 12,703,637 B2
(45) **Date of Patent: *Aug. 11, 2026**

(54) FUNCTIONALIZED SILICA NANORINGS, METHODS OF MAKING SAME, AND USES THEREOF

(71) Applicant: CORNELL UNIVERSITY, Ithaca, NY (US)

(72) Inventors: Melik Z. Turker, Princeton, NJ (US); Thomas C. Gardinier, II, Raritan, NJ (US); Ulrich B. Wiesner, Ithaca, NY (US); Kai Ma, Belle Mead, NJ (US)

(73) Assignee: Cornell University, Ithaca, NY (US)

( * ) Notice: Subject to any disclaimer, the term of this patent is extended or adjusted under 35 U.S.C. 154(b) by 1111 days.

This patent is subject to a terminal disclaimer.

(21) Appl. No.: 17/459,562

(22) Filed: Aug. 27, 2021

(65) Prior Publication Data

US 2022/0153596 A1 May 19, 2022

Related U.S. Application Data

(63) Continuation-in-part of application No. PCT/US2020/028372, filed on Apr. 15, 2020.

(60) Provisional application No. 63/071,268, filed on Aug. 27, 2020, provisional application No. 62/834,302, filed on Apr. 15, 2019.

(51) Int. Cl.

| | |
|---|---|
| ***C01B 33/12*** | (2006.01) |
| ***A61K 9/51*** | (2006.01) |
| ***A61K 33/00*** | (2006.01) |
| ***A61K 49/00*** | (2006.01) |
| ***A61K 51/12*** | (2006.01) |

(52) U.S. Cl.

CPC .............. *C01B 33/124* (2013.01); *A61K 9/51* (2013.01); *A61K 33/00* (2013.01); *A61K 49/005* (2013.01); *A61K 51/1244* (2013.01)

(58) Field of Classification Search

CPC ........ C01B 33/124; A61K 9/51; A61K 33/00; A61K 51/1244

See application file for complete search history.

(56) References Cited

U.S. PATENT DOCUMENTS

| | | | | |
|---|---|---|---|---|
| 9,028,880 | B2 | 5/2015 | Cheng et al. | |
| 9,682,063 | B2 * | 6/2017 | Weng .................. | A61K 9/5115 |
| 11,291,737 | B2 | 4/2022 | Wiesner et al. | |
| 2010/0255103 | A1 | 10/2010 | Liong et al. | |
| 2015/0366995 | A1 | 12/2015 | Wiesner et al. | |
| 2016/0008283 | A1 | 1/2016 | Nel et al. | |
| 2016/0287717 | A1 * | 10/2016 | Brinker ................ | A61K 9/5115 |
| 2018/0133346 | A1 | 5/2018 | Wiesner et al. | |
| 2020/0179538 | A1 | 6/2020 | Ma et al. | |
| 2021/0030901 | A1 | 2/2021 | Wiesner et al. | |
| 2021/0048414 | A1 | 2/2021 | Gardinier et al. | |

FOREIGN PATENT DOCUMENTS

| | | | |
|---|---|---|---|
| WO | 2016179260 | A1 | 11/2016 |
| WO | 2018213851 | A1 | 11/2018 |
| WO | 2019195858 | A1 | 10/2019 |
| WO | 2019213456 | A1 | 11/2019 |
| WO | 2020214741 | A1 | 10/2020 |
| WO | 2021092065 | A1 | 5/2021 |

OTHER PUBLICATIONS

Ma et al., J. Am. Chem. Soc. 2018, 140, 17343-17348. (Year: 2018).*

Zhong et al., ACS Appl. Mater. Interfaces 2016, 8, 10451-10458 (Year: 2016).*

Ma, et al., "Early formation pathways of surfactant micelle directed ultrasmall silica ring and cage structures," Journal of the American Chemical Society, vol. 140, No. 50, (2018) (6 pages).

Ma, et al., "Elucidating the Mechanism of Silica Nanoparticle PEGylation Processes Using Fluorescence Correlation Spectroscopies," Chem. Mater. Vol. 28, No. 5 (2016) (9 pages).

Turker et al. "Bimodal Morphology Transition Pathway in the Synthesis of Ultrasmall Fluorescent Mesoporous Silica Nanoparticles" J. Phys. Chem. (2019) (8 pages).

Turker et al. "Inner and Outer Surface Functionalizations of Ultrasmall Fluorescent Silica Nanorings As Shown by High Performance Liquid Chromatography" Chem. Mater. (2019) (10 pages).

Zhou, et al. "Ring assembly of silica nanospheres mediated by amphiphilic block copolymers with oxyethylene moieties," Polymer Journal, vol. 47, No. 2 (2014) (8 pages).

* cited by examiner

*Primary Examiner* — Robert S Cabral

(74) *Attorney, Agent, or Firm* — Young Basile Hanlon & MacFarlane, P.C.

(57) ABSTRACT

Silica nanorings, methods of making silica nanorings, and uses of silica nanorings. The silica nanorings may be PEGylated. The silica nanorings may be surface functionalized, which may be surface selective functionalization, with one or more polyethylene glycol (PEG) group(s), one or more display group(s), one or more functional group(s), or a combination thereof. The silica nanorings may have a size of 5 to 20 nm. The silica nanorings may be made using micelles. The absence or presence of the micelles during PEGylation and/or functionalization allows for surface selective functionalization. The silica nanorings may be used in various diagnostic and/or treatment methods.

23 Claims, 55 Drawing Sheets c
Fluorescent silica matrix
d
DEAC-NHS
APTES
DEAC-silane e TMR-maleimide
MPTMS
TMR-silane
f
MPTMS
Cy5-Maleimide
Cy5-silane e f g

| | Elution (min) | Elution (min) |
|---|---|---|
| Run time | 55 minutes | 35 minutes |
| Solvents | Water/Acetonitrile | Water/Acetonitrile |
| Gradient | Step+Linear | Linear |
| Column | 4.6 x 150 mm, C4 300 A pore size,<br>3.5 µm particle size | 4.6 x 50 mm, C18 300A pore size,<br>3.5 µm particle size |
| Flow rate | 0.75 mL/min | 1.2 mL/min |

Figure 7 (cont.)

Cy5-silane
MW 802

TMR-silane
MW 748 d e b m

TEM Size Analysis (100 particles measured for each)

| | | | | |
|---|---|---|---|---|
| **Average Size (nm):** | 7.3±0.9 nm | 10.8±0.8 nm | 12.3±1.1 nm | 12.1±1.4 nm |
| **Topology:** | sphere | hollow bead | cage | ring |

Figure 15 (cont.)

a b g h i $$M_1 \propto r_1^4 E K$$

$$M_2 \propto r_2^4 E K$$

$$\frac{M_2}{M_1} = 0.1 = \frac{r_2^4}{r_1^4}$$

$$r_2 = \sqrt[4]{0.1}\, r_1 = 0.56\, r_1$$

FUNCTIONALIZED SILICA NANORINGS, METHODS OF MAKING SAME, AND USES THEREOF

CROSS-REFERENCE TO RELATED APPLICATIONS

This application claims priority to U.S. Provisional Patent Application No. 63/071,268, filed on Aug. 27, 2020, and is a continuation-in-part of International Patent Application No. PCT/US2020/028372, filed on Apr. 15, 2020, which claims priority to U.S. Provisional Patent Application No. 62/834,302, filed on Apr. 15, 2019, the disclosures of each of which are hereby incorporated herein in their entirety by reference.

STATEMENT REGARDING FEDERALLY SPONSORED RESEARCH

This invention was made with government support under grant nos. CA199081 awarded by the National Institutes of Health and 1719875 awarded by the National Science Foundation. The government has certain rights in the invention.

BACKGROUND OF THE DISCLOSURE

In the past two decades, the field of ultrasmall nanoparticles (NPs) with sizes below 10 nm and potential applications ranging from catalysis to nanomedicine has garnered significant interest. While early efforts focused on dense spherical NPs, the field has since expanded to NPs with a variety of forms and shapes including high aspect ratio materials (i.e., rods and worms), star shaped NPs, as well as nanocages. The resulting silica nanomaterials have advantages, including robust synthetic protocols and high potential drug payloads. They do not, however, typically activate the renal pathway for rapid whole particle excretion in mammalian organisms, which requires particle diameters below the cut-off for renal clearance, i.e., below ~10 nm, thereby lowering the potential for adverse side effects. Synthesis and characterization of ultrasmall silica NPs (SNPs) with a number of different morphologies including single-pore mesoporous SNPs, silica nanorings, and silica nanocages have been reported. These types of NPs are of interest as they provide a pathway for clinical translation as a result of proven favorable biodistribution and pharmacokinetics profiles of ultrasmall SNPs, while simultaneously offering distinguishable inside and outside surfaces for orthogonal functionalization for surface directed multi-functionalization of NPs. Spherical multifunctional fluorescent oxide NPs have previously been reported with only one (outside) surface type available for ligand conjugation, but having two distinct surfaces in combination with ultrasmall particle sizes offers unique advantages, e.g., in therapeutic applications in nanomedicine as well as other applications such as the self-assembly of NPs.

In order to take advantage of distinct surfaces such as those present in ultrasmall single-pore mesoporous NPs or nanorings, the surface chemistry should be carefully characterized. Surface chemistry assessments of NPs remain challenging, however, as results of standard characterization techniques such as zeta potential measurements or dynamic light scattering are often limited to ensemble measurements, which do not offer a comprehensive description of the heterogeneity of surface chemical NP properties within a single sample batch.

SUMMARY OF THE DISCLOSURE

In an aspect, the present disclosure provides silica nanorings. Silica nanorings may be fluorescent silica nanorings. The silica nanorings comprise a single mesopore. The mesopore may be referred to as an aperture. The silica nanorings are discrete nanoscale structures. The silica nanorings may be circular or substantially circular. A silica nanoring may be a torus defining a single aperture. The silica nanorings may have a size 20 nm or less (e.g., 5 nm to 20 nm). The silica matrix of a silica ring may comprise one or more dye group(s). A nanoparticle may have various numbers of polyethylene glycol (PEG) groups covalently bonded to at least a portion of or all of the surfaces of a nanoring. The silica nanoring may be functionalized (e.g., surface selectively functionalized or the like) with one or more display group(s) that may have various function (e.g., imaging, sensing functionality, chelating ability, targeting ability, diagnostic ability, therapeutic ability, reactivity to form a group having such function, etc.

In an aspect, the present disclosure provides compositions comprising silica nanorings of the present disclosure. The compositions comprise one or more silica nanoring(s) of the present disclosure. A composition may comprise additional components. For example, the composition comprises a buffer solution suitable for administration to an individual (e.g., a mammal such as, for example, a human or a non-human). A composition may include one or more standard pharmaceutically acceptable carrier(s). A composition may comprise combinations of silica nanorings (e.g., two or more structurally distinct silica nanorings).

In an aspect, the present disclosure provides methods of making silica nanorings. A method may be based on self-assembly of silica nanorings. A method of making silica nanorings may comprise forming a reaction mixture comprising one or more silica precursor(s) (one or more of which may comprise a dye group); one or more surfactant(s); one or more pore expander(s); and holding the reaction mixture at a time and/or temperature, whereby silica nanorings having an average size of 20 nm or less are formed; and optionally, adding a PEG precursor or functionalized PEG precursor) to the reaction mixture. The silica nanorings may be further functionalized with display group(s) and/or functional group(s). The functionalization may be surface specific. The silica nanorings may be subjected to post-synthesis processing steps.

In an aspect, the present disclosure provides methods of characterizing silica nanorings. In various examples, silica nanorings and/or functionalized silica nanorings (which may be present in a composition) are characterized by high performance liquid chromatography (HPLC). High performance liquid chromatography (HPLC) may be used to determine the location of display groups functionalized on the surface of the silica nanorings. HPLC methods described herein may be used to identify and/or separate nanorings selectively surface functionalized on the inner and/or outer surface of a single batch of silica nanorings.

In an aspect, the present disclosure provides uses of silica nanorings. In various examples, silica nanorings or a composition comprising silica nanorings are used in delivery and/or imaging methods. The present disclosure provides methods of using one or more silica nanoring(s) and/or one or more composition(s) comprising administering one or more silica nanoring(s) to treat cancer.

In an aspect, the present disclosure provides kits. In various examples, a kit comprises one or more silica nanoring(s) and/or one or more composition(s) of the present disclosure.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
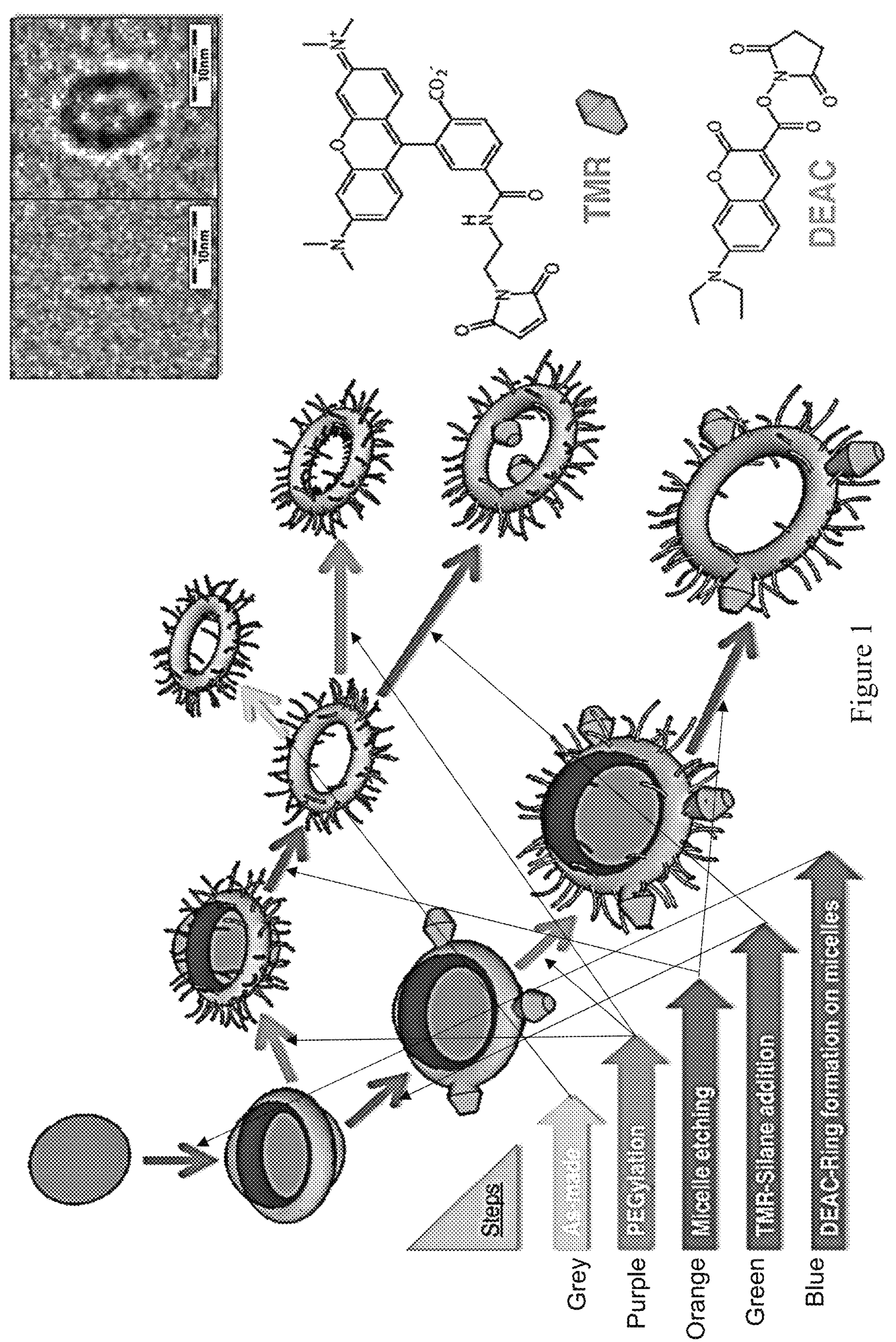
FIG. 1 shows steps (bottom left, not in representative sequence) to orthogonally PEGylate and functionalize inside and outside surfaces of ultrasmall silica nanorings. Surfactant micelles (top left) act as templates for silica nanoring growth, simultaneously encapsulating DEAC dye in the silica matrix. After dyed silica nanoring formation, individual steps along two different pathways are taken in order to be able to specifically PEGylate and/or functionalize the outside (bottom sequence) and inside (top sequence) surfaces of the rings. Individual steps include PEGylation, micelle removal, and TMR-silane additions. Representative cryo-EM/TEM images show two orthogonal projections of a silica nanoring (edge on, left; planar, right) formed around a TMB swollen CTAB micelle (top right).

Although claimed subject matter will be described in terms of certain examples and embodiments, other examples and embodiments, including examples and embodiments that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (e.g., either lower limit value or upper limit value) and ranges between the values of the stated range.

As used herein, unless otherwise indicated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent radicals and multivalent radicals, such as, for example, divalent radicals, trivalent radicals, and the like). Examples of groups include, but are not limited to:

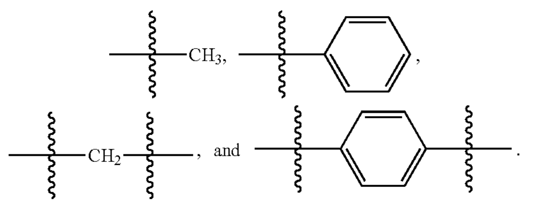

A group may be alternatively referred to as a moiety.

Some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. In various examples, about refers to ±1%, ±2%, ±3%, ±4%, ±5%. ±6%, ±7%, ±8%, ±9%, or ±10% of the given value.

The present disclosure provides silica nanorings. The present disclosure also provides methods of making and using the silica nanorings.

In an aspect, the present disclosure provides silica nanorings. Silica nanorings may be fluorescent silica nanorings. The silica nanorings comprise a single mesopore. The mesopore may be referred to as an aperture. In an example, a silica nanoring does not have icosahedral symmetry. In various examples, a silica nanoring is not a silica cage or a silica nanoparticle.

The silica nanorings are discrete nanoscale structures. The silica nanorings may be circular or substantially circular. A silica nanoring may be a torus defining a single aperture.

A silica nanoring comprises a silica matrix. A portion of or all the silica matrix of a silica nanoring is microporous. A portion or portions of or all the silica matrix of a silica nanoring may be functionalized. Non-limiting examples of functionalization(s) are provided herein.

The silica matrix may have various sizes. The silica matrix may have modulated thickness (e.g., one or more modulated dimension(s) normal to a long axis of the silica matrix or the like). In various examples, the silica matrix has a modulated diameter, modulated radius, or the like. In various examples, the silica matrix does not have homogeneous (e.g., constant) diameter, radius, or the like, or a combination thereof.

In various examples, the silica matrix has a plurality of silica domains, where at least two domains (which may be referred to as first domains) are connected (e.g., covalently bonded by a plurality of Si—O—Si bonds or the like) by a silica domain (which may be referred to as a second silica domain) and this domain (e.g., second silica domain) has a dimension normal to a long axis of the silica matrix that is 50% or less (e.g., 10-50%, including all 0.1% values and ranges therebetween) than a dimension normal to a long axis of the silica matrix of one or both of the two domains (e.g., first domain(s)). The two domains (e.g., first domain(s)) may have (e.g., predominantly have) a Q3 silica structure (e.g., may comprise a plurality of Q3 bonded silicon atoms). A second domain may be referred to as a linker. A linker may have (e.g., predominantly have) a Q2 silica structure (e.g., a linker may comprise a plurality of linear silicon-oxygen-silicon groups (e.g., a plurality of —O—Si—O—Si—O— groups arranged in a linear manner, which may be considered an oligomeric siloxane group or a polysiloxane group or oligomeric siloxane groups or polysiloxane groups)). A silica matrix may comprise a plurality of first domains, where adjacent first domains are linked by a thinner (e.g., linking or the like) second domain, may be referred to as "pearl chain" structure. In various examples, the silica matrix comprises 30% or more, 40% or more, 50% or more, or 60% or more Q4 silicon atoms. In various other examples, the silica matrix does not comprise 40% or more, 50% or more, 60% or more, or 70% or more Q4 silicon atoms.

Without intending to be bound by any particular theory, it is considered that a silica matrix comprising a plurality of first domains, where adjacent first domains are linked by a thinner (e.g., linking) second domain are able to deform (e.g., exhibit a bending modulus or the like that allows the silica nanoring to adopt a shape with at least one dimension that is smaller than the diameter of the silica nanoring that is not deformed) and pass thru an aperture having an opening smaller than the longest dimension of this silica nanoring. In various examples, a silica nanoring having a longest dimension greater than 6 nm (generally considered to be the limit of renal clearance of an individual, such as, for example, a human, a non-human animal, or the like) can clear (e.g., pass thru) the kidneys of an individual, such as, for example, a human, a non-human animal, or the like).

Silica nanorings may have various sizes. The silica nanorings may have a size, e.g., a longest dimension or the like, which may be a longest linear dimension, such as, for example, an outer diameter, of 20 nm or less (e.g., 5 nm to 20 nm, such as, for example, 5 nm to 8 nm, 7 nm to 15 nm or 9 nm to 12 nm, including every 0.1 nm value and range therebetween. The size may or may not include any surface dye group(s), display group(s), or the like. The silica nanoring size can be measured by methods known in the art. In various examples, the size is a hydrodynamic size or is measured using transmission electron microscopy (TEM).

Silica nanorings may have various sizes (e.g., hydrodynamic sizes or sizes measured using TEM or the like). For example, a silica nanoring has a hydrodynamic size of 7 nm to 15 nm, including every 0.1 nm value and range therebetween. For example, the silica nanoring has a hydrodynamic size of 9 to 12 nm (e.g., 9.1 nm, 9.6 nm, 10.0 nm, 10.4 nm, 10.7 nm, 11.0 nm, 11.1 nm, or 11.7 nm).

A pore (or aperture) of a silica nanoring can have various sizes (e.g., diameter or the like). For example, a silica nanoring has an inner diameter of 3 nm to 13 nm, 3 nm to 8 nm or 4 nm to 8 nm, including every 0.1 nm value and range therebetween. For example, the pore of a silica nanoring is about 6 nm.

The width/thickness of a non-surface functionalized (e.g., no PEG functionalization or the like) silica nanoring is typically about 2 nm, and when the silica nanorings are surface functionalized (e.g., with 6-9 EO unit PEG groups) are conjugated to the ring surface, this may add about 1 nm thickness (on either side of the nanoring, i.e., approximately 1 nm on the outer surface (e.g., depending on the number of EO groups in the PEG groups), and approximately 1 nm on the inner surface (e.g., depending on the number of EO groups in the PEG groups)).

Without intending to be bound by any particular theory, it is considered the silica nanorings are flexible and can deform to pass through channels having a width smaller than the silica nanoring size. It is considered that silica nanorings having a size of 10 nm or greater that would not typically allow renal clearance from an individual by the kidneys can be cleared from an individual by the kidneys.

The silica matrix of a silica ring may comprise one or more dye group(s). Non-limiting examples of dyes and dye groups are described herein. The silica matrix may have one or more dye group(s) disposed in (e.g., encapsulated within) the silica matrix and/or disposed on (e.g., covalently bonded to) at least a portion of the surface of the silica matrix. In various examples, a silica ring comprises 1, 2, 3, 4, or 5 dye groups disposed in (e.g., encapsulated within) the silica matrix and/or disposed on (e.g., covalently bonded to or the like) at least a portion of the surface of the silica matrix.

A nanoparticle may have various numbers of polyethylene glycol (PEG) groups (which may be referred to as PEG chains) covalently bonded to at least a portion of or all of the surfaces of a nanoring. In various examples, least a portion of a surface (e.g., an outer surface, an inner surface, or a combination thereof) or all of the surfaces of a silica nanoring have 300 to 500 PEG groups, including all integer number of PEG groups and ranges therebetween, covalently bonded to the surface(s) of the nanoring. It may be desirable that at least a portion of or all of the outer surface is functionalized with PEG groups independently at each occurrence comprising 6, 7, 8, or 9 ethylene glycol repeat units and/or at least a portion of or all of the inner surface is functionalized with PEG groups independently at each occurrence comprising 2, 3, or 4 ethylene glycol repeat units, and, optionally, the silica matrix of the nanoring having a plurality of fluorescent display groups (e.g., dye groups or the like) covalently bound to the silica matrix.

The silica nanoring may be functionalized (e.g., as described herein) with one or more display group(s). The silica nanorings can be functionalized using various methods (e.g., as described herein). At least a portion of a surface (e.g., at least a portion of an outer surface and/or at least a portion of an inner surface of the silica nanorings may be functionalized (e.g., covalently functionalized and/or non-covalently functionalized).

Various display groups can be used. A display group may be referred to as a ligand. A display group may be a functional group (e.g., metal chelator groups, reactive group (which may be reacted to form a display group), or the like) that may be further reacted to form a display group. In an example, a reactive group comprises a chemical functional group that can be conjugated to molecule (such as, for example, a drug molecule, targeting molecule, or the like), atom, or the like, to form a display group. Non-limiting examples of reactive groups include amines, thiols, carboxylic acids/carboxylates, esters (e.g., activated esters and the like), azides, alkenes, alkynes, and the like. A display group may be conjugated (e.g., covalently bonded or non-covalently), which may be via a liking group, to a silica surface of the silica nanoring. A display group may be conjugated to a surface of a silica nanoring via a linking group. The linking group may be a part of a display group precursor or a PEG group. A display group may be covalently bonded to a PEG group that is covalently bonded to a silica surface. In various examples, a display group is conjugated to a PEG group via a functional group formed using a Click reaction. A linker group may comprise a group (e.g., a disulfide group or the like) that allows the display group to be released (e.g., in an individual) under certain conditions (e.g., reducing conditions for a disulfide group or the like). In various examples, a silica nanoring has one or more display group(s) covalently bonded to and encapsulated by the silica matrix of the silica nanoring.

The display groups can have various functionality (e.g., absorbance/emission behavior, such as, for example, fluorescence and phosphorescence, which may be used for imaging, sensing functionality (e.g., pH sensing, ion sensing, oxygen sensing, biomolecules sensing, temperature sensing, and the like), chelating ability, targeting ability (e.g., antibody fragments, aptamers, proteins/peptides/oligomers (natural, truncated, or synthetic), nucleic acids, such as, for example, DNA and RNA, and the like), diagnostic ability (e.g., radioisotopes and the like), therapeutic ability (e.g., radiotherapeutics, drugs (e.g., gefitinib and the like), nucleic acids, and the like), reactivity to form a group having such functionality (which may be referred to as a reactive group), and the like, and combinations thereof. A display group can be formed from a compound exhibiting functionality by derivatization of the compound using conjugation chemistry and reactions known in the art. Non-limiting examples of display groups include dye groups, metal chelating groups (with or without a metal), therapeutic groups, functional groups, which may be referred to as functional chemical groups, and the like, and combinations thereof. In various examples, a silica nanoring has 3 to 300 display groups, including all integer number of display groups and ranges therebetween, covalently or non-covalently bound to a surface of the silica nanorings.

The display groups carried by the silica nanorings may include groups formed from diagnostic and/or therapeutic agents. Non-limiting examples of diagnostic agents include, but are not limited to, dyes, radioisotopes, and the like, and combinations thereof. Non-limiting examples of therapeutic agents include, but are not limited to, drugs, such as, for example, chemotherapeutic agents, antibiotics, antifungal agents, antiparasitic agents, antiviral agents, nucleic acids, and the like, and combinations thereof.

A silica nanoring may comprise a combination of different display groups. For example, a silica nanoring may have 0-10 (e.g., 0, 1, 2, 3, 4, 5, 6, 7, 8, 9, or 10) structurally distinct display group(s).

A display group may comprise (or be) a therapeutic agent or a group formed from a therapeutic agent. Non-limiting examples of therapeutic agents, which may be drugs, include, but are not limited to, chemotherapeutic agents, antibiotics, antifungal agents, antiparasitic agents, antiviral agents, and combinations thereof, and groups derived therefrom. Examples of suitable drugs/agents are known in the art.

A silica nanoring may comprise various dyes (e.g., display groups formed from a dye or the like). In various examples, the dyes are organic dyes. In an example, a dye does not comprise a metal atom. Non-limiting examples of dyes include those described in Example 1. Non-limiting examples of dyes include fluorescent dyes (e.g., near infrared (NIR) dyes and the like), phosphorescent dyes, non-fluorescent dyes (e.g., non-fluorescent dyes exhibiting less than 1% fluorescence quantum yield and the like), fluorescent proteins (e.g., EBFP2 (variant of blue fluorescent protein), mCFP (Cyan fluorescent protein), GFP (green fluorescent protein), mCherry (variant of red fluorescent protein), iRFP720 (Near Infra-Red fluorescent protein)), and the like, and groups derived therefrom. In various examples, a dye absorbs in the UV-visible portion of the electromagnetic spectrum. In various examples, a dye has an excitation and/or emission in the near-infrared portion of the electromagnetic spectrum (e.g., 650-1700 nm).

Non-limiting examples of organic dyes include cyanine dyes (e.g., Cy5®, Cy3®, Cy5.5®, Cy7®, Cy7.5®, and the like), carborhodamine dyes (e.g., ATTO 647N (available from ATTO-TEC and Sigma Aldrich®), coumarin dyes (e.g., 7-diethylaminocoumarin-3-carboxylic acid, and the like), BODIPY dyes (e.g., BODIPY 650/665 and the like), xanthene dyes (e.g., fluorescein dyes such as, for example, fluorescein isothiocyanate (FITC), Rose Bengal, and the like), eosins (e.g., Eosin Y and the like), and rhodamines (e.g., TAMRA, tetramethylrhodamine (TMR), TRITC, DyLight® 633, Alexa 633, HiLyte 594, and the like), Dyomics® DY800, Dyomics® DY782, and IRDye® 800CW, and the like, and groups derived therefrom.

A silica nanoring may comprise various sensor groups. Non-limiting examples of sensor groups include pH sensing groups, ion sensing groups, oxygen sensing groups, biomolecule sensing groups, temperature sensing groups, and the like, and combinations thereof. Examples of suitable sensing compounds/groups are known in the art.

A silica nanoring may comprise various chelator groups. Non-limiting examples of chelator groups include deferoxamine (DFO), 1,4,7,10-tetraazacyclododecane-1,4,7,10-tetraacetic acid (DOTA), 1,4,7-triazacyclononane-1,4,7-triacetic acid (NOTA), ethylenediaminetetraacetic acid (EDTA), diethylenetriaminepentaacetic acid (DTPA), porphyrins, and the like, and groups derived therefrom. A chelator group may comprise a radioisotope. Examples of radioisotopes are described herein and are known in the art.

A display group may comprise one or more radioisotope(s). A radioisotope may be a diagnostic agent and/or a therapeutic agent. A radioisotope may be a radiotherapeutic label (e.g., $^{225}$Ac, $^{177}$Lu, and the like) or a radionuclide (e.g., $^{89}$Zr, $^{124}$I, $^{131}$I, and the like, and the like). For example, a radioisotope, such as, for example, $^{124}$I, is used for positron emission tomography (PET) imaging. A radioisotope may be chelated to a chelating group.

A targeting group may also be conjugated to the silica nanoring to allow targeted delivery of a silica nanoring. A targeting group can be formed from (derived from) a targeting molecule. For example, a targeting group, which is capable of binding to a cellular component (e.g., on the cell membrane or in the intracellular compartment or the like) associated with a specific cell type, is conjugated to the silica nanoring. The targeting group may be a tumor marker or a molecule in a signaling pathway. The targeting group may have specific binding affinity to certain cell types, such as, for example, tumor cells. In certain examples, the targeting group may be used for guiding the silica nanorings to specific areas, such as, for example, liver, spleen, brain or the like, or a specific cancer tissues, for example melanoma, brain tumors, breast cancer, prostate cancer, or the like. Imaging can be used to determine the location of the silica nanorings in an individual. Examples of targeting groups include, but are not limited to, linear and cyclic peptides (e.g., $\alpha_v\beta_3$ integrin-targeting cyclic(arginine-glycine-aspartic acid, tyrosine-cysteine) peptides, c(RGDyC), and the like), antibodies, antibody fragments, various DNA and RNA segments (e.g., siRNA), and the like, groups derived therefrom, and combinations thereof. A peptide may be a targeting peptide, such as, for example, cRGDyC, α-MSH, PSMAi, and the like. Targeting peptide groups may be cancer targeting peptide groups.

As used herein, unless otherwise stated, the term "derived" refers to formation of a group by reaction of a native functional group of a compound (e.g., formation of a group via reaction of an amine of a compound and a carboxylic acid to form a group or the like) or chemical modification of a compound to introduce a new chemically reactive group on the compound that is reacted to form a group.

The silica nanorings may be selectively functionalized with various display groups. Multiple different display groups and combinations of display groups may be functionalized on an inner and/or an outside surface of a silica nanoring. In an example, a silica nanoring comprises an inner surface, outer surface, and pore, wherein the silica nanoring may optionally be functionalized (e.g., selectively functionalized) on the inner surface and/or outer surface with one or more display groups(s). In an example, the silica nanorings (which may be PEGylated) are functionalized with a drug and/or drug linker on the inner surface and a targeting group on the outside surface. In various examples, at least a portion or all of the display groups are hydrophilic and/or hydrophobic. In various examples, at least a portion of or all of a functionalized inner surface is hydrophobic or hydrophilic and/or at least a portion of or all of a functionalized outer surface is hydrophilic.

The silica nanorings may be surface selectively functionalized. A silica nanoring (e.g., a fluorescent silica nanoring) may be selectively functionalized on the inner surface and/or outer surface of the silica nanoring. The functionalization may be the same for the inner surface and outer surface of the silica nanoring or may be different for the inner surface and outer surface of the silica nanoring. The inner and outer surface of the silica nanorings may be selectively modified with desired display groups via both covalent and non-covalent interactions for different applications. For example, the outer surface of a silica nanoring is covalently functionalized with PEG for improving bio-compatibility. In another example, the outer surface of the silica nanorings is further covalently functionalized with display group groups for theranostic applications, including, but not limited to, peptide groups, RNA groups, DNA groups, drug groups, sensor groups, antibody groups, antibody fragments groups, radioisotope groups, and the like, and combinations thereof. The silica matrix of the silica nanorings may be covalently labeled with a fluorescent dye to endow the silica nanorings with fluorescence properties. The functionalization location may be confirmed by using high performance liquid chromatography.

The display group(s) carried by the silica nanorings may comprise (or be) diagnostic and/or therapeutic agents (e.g., radioisotopes, drugs, nucleic acids, and the like). In various examples, the silica matrix of a silica nanoring comprises DEAC groups covalently bonded to the silica matrix. In various examples, a silica nanoring is surface functionalized with TMB groups and Cy5 groups. In various examples, the silica matrix of a silica nanoring comprises 7-diethylamino-coumarin-3-carboxylic acid groups covalently bonded to the silica matrix and the silica nanoring is surface functionalized with TMB groups and Cy5 groups.

The silica nanoring may comprise one or more fluorescent dye(s) (florescent dye group(s)). In various examples, the silica ring matrix comprise one or more dye group(s) and/or the inner and/or outer surface of the ring are surface functionalized with the dye groups(s). The silica nanoring may comprise one or more radiolabel(s). In various examples, the inner and/or outer surface of the ring are surface functionalized with the radiolabel(s).

In an aspect, the present disclosure provides compositions comprising silica nanorings of the present disclosure. The compositions comprise one or more silica nanoring(s) of the present disclosure.

A composition may comprise additional components. For example, the composition comprises a buffer solution suitable for administration to an individual (e.g., a mammal such as, for example, a human or a non-human mammal). An individual may be a subject. The buffer solution may be a pharmaceutically-acceptable carrier.

A composition may include one or more standard pharmaceutically acceptable carrier(s). Non-limiting examples of compositions include solutions, suspensions, emulsions, solid injectable compositions that are dissolved or suspended in a solvent before use, and the like. Injections may be prepared by dissolving, suspending or emulsifying one or more of the active ingredient(s) in a diluent. Non-limiting examples of diluents include distilled water for injection, physiological saline, vegetable oil, alcohol, and the like, and combinations thereof. Further, the injections may contain stabilizers, solubilizers, suspending agents, emulsifiers, soothing agents, buffers, preservatives, and the like. Injections may be sterilized in the final formulation step or prepared by sterile procedure. The composition may also be formulated into a sterile solid preparation, for example, by freeze-drying, and can be used after sterilized or dissolved in sterile injectable water or other sterile diluent(s) immediately before use. Non-limiting examples of pharmaceutically acceptable carriers can be found in: *Remington: The Science and Practice of Pharmacy* (2005) 21st Edition, Philadelphia, PA Lippincott Williams & Wilkins.

A composition may comprise a plurality silica nanorings. A composition may comprise combinations of silica nanorings (e.g., two or more structurally distinct silica nanorings or the like). Any of the silica nanorings may be surface functionalized with one or more kind of PEG group(s) (e.g., PEG group(s), functionalized (e.g., functionalized with one or more display group(s)) PEG group(s), or a combination thereof). The silica nanorings may be made by a method of the present disclosure.

In an aspect, the present disclosure provides methods of making silica nanorings. A method may be based on self-assembly of silica nanorings.

Silica nanorings may be produced through self-assembly. Without intending to be bound by any particular theory, it is considered that under synthesis conditions, the silica precursors condense forming primary clusters that self-assemble into silica nanoring structures on a surface of the micelles. The micelles may be structure directing. In various examples, the following are introduced during synthesis: i) hydrophobic reagent(s) (which may be referred to as pore expander(s)), such as, for example, TMB, are encapsulated inside the surfactant micelles, to increase micelle deformability, facilitating the silica nanoring formation; ii) desired reaction kinetics of the silica precursors are realized by adjusting reaction conditions to the point that primary inorganic particles can form in solution to self-assemble on micelle surface. At a desired point, condensation of silica precursors is rapidly terminated to prevent further growth of the silica nanorings; and iii) water is used as the reaction media, and thus hydrophobicity/hydrophilicity and electrostatic interactions can simultaneously take effect to trigger self-assembly. Without intending to be bound by any particular theory, it is considered the silica nanoring structure results from a balance between these different interactions among the reaction components.

A method of making silica nanorings may comprise forming a reaction mixture comprising one or more precursor(s); one or more surfactant(s) (e.g., surfactant(s) including positively charged head group/groups or surfactant(s) including negatively charged head group/groups); one or more pore expander(s) (e.g., a hydrophobic pore expander); and holding the reaction mixture at a time (e.g., $t^1$) and/or temperature (e.g., $T^1$), whereby silica nanorings having an average size (e.g., average longest dimension, which may be an average longest linear dimension, such as, for example, an average outer diameter) of 20 nm or less are formed; and optionally, adding a terminating agent (which may be a PEG precursor or functionalized PEG precursor) to the reaction mixture. Without intending to be bound by any particular theory, it is considered that the surfactant(s) and pore expander(s) form micelles that can function as templates for silica nanoring formation.

Various silica precursors can be used. Combinations of silica precursors may be used. A silica precursor may be a silica-generating sol-gel precursor. A silica precursor may be a silicon alkoxide (e.g., tetraalkoxysilane, alkyltrialkoxysilane, or the like) or a functionalized silicon alkoxide, or the like, and may have a plurality of alkoxy groups and the alkyl group of each of the alkoxy groups may independently be a $C_1$ to $C_4$ alkyl group and, optionally one or more alkyl group(s) directly bonded to the silicon, where the alkyl group(s) may independently be a $C_1$ to $C_6$ alkyl group. Non-limiting examples of silica precursors include tetraalkoxysilanes (e.g., tetramethylorthosilicate (TMOS), tetraethylorthosilicate (TEOS), tetrapropylorthosilicate (TPOS), and the like), alkyltrialkoxysilanes (e.g., methyltrimethylorthosilicate), functionalized silica precursors (e.g., (3-aminopropyl)triethoxysilane (APTES), (3-aminopropyl) trimethoxysilane (APTMS), (3-mercaptopropyl)trimethoxysilane (MPTMS), and the like and combinations thereof), and the like, and combinations thereof. In various examples, functionalized silica precursors are amino-functionalized silica precursors, thiol-functionalized silica precursors or the like, such as, for example, aminoalkyl-functionalized silica precursors, alkylthiol-functionalized silica precursors, and the like. It may be desirable that at least one of the silica precursors is TMOS or the only silica precursor is TMOS. A functionalized silica precursor may be 0.1 to 20 mol % (of the total moles of precursors), including all 0.1 mol % values and ranges therebetween.

A silica precursor may be a functionalized silica precursor. A functionalized silica precursor may comprise one or more display group(s) (e.g., one or more display group(s) described herein). In non-limiting examples, a silica precursor comprises a fluorescent dye group (e.g., is a dye-silane conjugate, such as, for example, ATTO647N-silane, 7-diethylaminocoumarin-3-carboxylic acid, succinimidyl ester (DEAC), and the like) and/or a peptide group (e.g., is a peptide-silane conjugate, such as, for example, cRGDY-silane) and/or a drug (e.g., is a drug-silane conjugate). In other non-limiting examples, a silica precursor comprises one or more iodide atom(s).

A reaction mixture can comprise various surfactants. A reaction mixture may comprise combinations of surfactants. A surfactant may be a cationic surfactant, which may form a micelle with a positive surface charge. A surfactant may be an anionic surfactant, which may form a micelle with a negative charge.

Without intending to be bound by any particular theory, it is considered that the silica precursor(s) form silica clusters (e.g., silica clusters having a size, which may be a longest dimension, which may be a longest linear dimension, of 10 nm or less or about 2 nm) in the reaction mixture and the silica clusters (which may be positively or negatively charged) are electrostatically attracted to a micelle surface (which may be negatively or positively charged, respectively) and selectively deposit on one or more surface(s) of the micelle forming a silica nanoring. The clusters may be referred to as primary silica clusters. The clusters may comprise a plurality of —O—Si—O— groups. It is desirable that the precursor(s) form clusters having a charge opposite that of the micelle. The pH of the reaction mixture may be adjusted to form micelles and/or clusters with a desired charge.

A cationic surfactant may be a $C_{10}$ to $C_{18}$ alkyltrimethylammonium halide. Non-limiting examples of $C_{10}$ to $C_{18}$ alkyltrimethylammonium halides include cetyltrimethylammonium bromide (CTAB), decyltrimethylammonium bromide ($C_{10}$TAB), dodecyltrimethylammonium bromide ($C_{12}$TAB), myristyltrimethylammonium bromide ($C_{14}$TAB), octadecyltrimethylammonium bromide ($C_{18}$TAB), and the like, and combinations thereof.

Various anionic surfactants can be used. Combinations of surfactants may be used. An anionic surfactant may be an alkyl sulfate. Non-limiting examples of anionic surfactants include sodium dodecyl sulfate (SDS), N-myristoyl-L-glutamic acid (C14GluA), and the like, and combinations thereof.

Various amounts of surfactant(s) can be used. The surfactant(s) may be present in a reaction mixture at a concentration of 1 mg/mL to 50 mg/mL, including all integer mg/mL values and ranges therebetween.

Various pore expanders can be used. Combinations of pore expanders may be used. A pore expander is a hydrophobic molecule. A pore expander may be disposed in a surfactant micelle (e.g., disposed in the center or in about the center of a surfactant micelle). A pore expander may be referred to as an oil. A pore expander can provide micelles that are larger than micelles formed using the same surfactant(s) in the absence of that pore expander.

A pore expander may be an alkylated benzene (e.g., a mono-, di-, or trialkylated benzene or the like). The alkyl group(s) of the alkylated benzenes may independently be $C_1$ to $C_6$ alkyl group(s) (e.g., $C_1$, $C_2$, $C_3$, $C_4$, $C_5$, or $C_6$ alkyl groups(s)). Non-limiting examples of alkylated benzenes include 1,2,4-trimethylbenzene (TMB), toluene, and the like. A pore expander may be a polymer monomer with one or more polymerizable group(s). Non-limiting examples of polymer monomers include styrenes, alkylstyrenes (e.g., methyl styrene, and the like). The alkyl group(s) of the alkylstyrenes may be $C_1$ to $C_6$ alkyl group(s) (e.g., $C_1$, $C_2$, $C_3$, $C_4$, $C_5$, or $C_6$ groups(s)). A pore expander may be a hydrophobic solvent. Non-limiting examples of hydrophobic solvents include alkanes (e.g., hexane and the like), cycloalkanes (e.g., cyclohexane and the like), benzene, alkylated benzenes (e.g., toluene and the like), chlorinated alkanes (e.g., chloroform and the like)), and the like, and combinations thereof.

Various amounts of pore expander(s) can be used. The pore expander(s) may be present in a reaction mixture at a concentration of 0.05 mg/mL to 150 mg/mL, including all integer mg/mL values and ranges therebetween.

The surfactant(s) and pore expander(s) can be used in various ratios. The surfactant(s) and pore expander(s) may be present in a reaction mixture at molar ratio of 1:2 to 1:10, including all 0.1 ratio values and ranges therebetween.

A nanoring forming reaction can be carried out for various times and/or temperatures. The reaction time may be 1 minute to 48 hours and/or the reaction temperature may be room temperature to 95° C. A reaction mixture may be formed by combining the surfactant(s), pore expanding molecule(s), and, solvent(s), if present and holding this mixture for a selected time (e.g., up to 24 hours) and temperature and subsequently adding the silica precursor(s).

A reaction mixture may comprise one or more solvent(s). In an example, a reaction mixture further comprises a solvent and the solvent is water and the pH of the reaction mixture is 5 or greater (e.g., 5-9) or 6 or greater (e.g., 6-9). In various examples, ammonium hydroxide is used as a base, to make the aqueous solution pH slightly basic (approximately pH 8).

The methods may be carried out in a reaction mixture comprising an aqueous reaction medium (e.g., water or the like). For example, the aqueous medium comprises water. Certain reactants may be added to the various reaction mixtures as solutions in a polar aprotic solvent (e.g., DMSO, DMF, or the like). In various examples, the aqueous medium does not contain organic solvents (e.g., alcohols such as, for example, $C_1$ to $C_6$ alcohols) other than polar aprotic solvents at 10% or greater, 20% or greater, or 30% or greater by weight (based on the total weight of the solvent). In an example, the aqueous medium does not contain alcohols at 1% or greater, 2% or greater, 3% or greater, 4% or greater, or 5% or greater by weight (based on the total weight of the solvent). In an example, the aqueous medium does not contain any detectible alcohols. For example, the reaction medium of any of the steps of any of the methods disclosed herein consists essentially of water and, optionally, a polar aprotic solvent.

At various points in the methods, the pH can be adjusted to a desired value or within a desired range. It may be desirable that the pH of the reaction mixture be such that negatively charged primary silica particles or positively charged silica particles are formed (e.g., stabilized). The pH of the reaction mixture can be increased by addition of a base and/or lowered by addition of an acid. Non-limiting examples of bases include ammonium hydroxide (which may be desirable in the case of methods of making silica nanorings), alkali hydroxides, such as, for example, sodium hydroxide or potassium hydroxide, and the like, and combinations thereof. Non-limiting examples of suitable acids include inorganic acids (e.g., hydrochloric acid, nitric acid, sulfuric acid, and the like), organic acids (e.g., acetic acid and the like), and the like, and combinations thereof.

The nanoring matrix or a surface of a nanoring may be functionalized without a PEG linker. In various examples, fluorescent dye-silane conjugates are co-condensed into the silica matrix, or the fluorescent dyes are directly attached to one or more silica nanoring surface(s) via amine-active ester conjugation (amine silane on silica surface, active ester group on dye) or thiol-maleimido chemistry (thiol-silane on silica surface and maleimido functional group on dye), or both. In various examples, the display group(s) encapsulated in the silica matrix is/are fluorescent dye group(s), and other display groups are either disposed on one or more silica surface(s) or attached to the PEG groups covalently bonded to one or more silica surface(s).

Formation of the silica nanorings may be terminated by addition of one or more PEG-silane(s), any of which may be functionalized as described herein. Combinations of terminating agents may be used. This is an example of PEGylation.

PEGylation of at least a portion of a surface (e.g., an outer surface, an inner surface, or a combination thereof) or all of the surfaces of a silica nanoring, which may be used to terminate and/or functionalize a silica nanoring, may be carried out at a variety of times and/or temperatures. For example, PEGylation is carried out by contacting the silica nanorings with one or more PEG-silane(s), any one of which may be functionalized as described herein, at room temperature up to 100° C. for 0.5 minutes to 48 hours (e.g., overnight). PEGylation may be carried out before or after the surfactant(s) and/or pore expander(s) (e.g., micelles) are removed from the nanorings.

The chain length of the PEG group of a PEG-silane (i.e., the number of ethylene glycol repeat units of the PEG chain) can be tuned from 3 to 24 (e.g., 3, 4, 5, 6, 7, 8, 9, 10, 11, 12, 13, 14, 15, 16, 17, 18, 19, 20, 21, 22, 23, or 24) EO units (e.g., 3 to 6, 3 to 9, 6 to 9, 8 to 12, or 8 to 24 EO units). The PEG chain length of PEG-silane may be selected to tune the thickness of the PEG layer surrounding the silica nanorings and/or the pharmaceutical kinetics profiles of the PEGylated silica nanorings. The PEG chain length of display group-functionalized PEG-silane may be used to tune the accessibility of the display groups on the surface of the PEG layer of the silica nanorings resulting in varying binding and targeting performance.

PEG-silane conjugates may comprise a display group or a functional group. The display group or functional group is covalently bound to the PEG group of the PEG-silane conjugates (e.g., via the hydroxy terminus of the PEG-silane conjugates or the like). A display group or functional group may be conjugated to a terminus of the PEG group opposite the terminus conjugated to the silane group. A PEG-silane conjugate can be formed using a heterobifunctional PEG compound (e.g., maleimido-functionalized heterobifunctional PEG precursors, NHS ester-functionalized heterobifunctional PEG precursors, amine-functionalized heterobifunctional PEG precursors, thiol-functionalized heterobifunctional PEG precursors, and the like).

For example, a PEG-silane conjugate comprising a display group is added in addition to PEG-silane. In this case, a silica nanoring surface functionalized with PEG groups and PEG groups comprising a display group. The conversion percentage of display group-functionalized or reactive group-functionalized PEG-silane is 40% to 100% and the number of display group-functionalized PEG-silane precursors reacted with each particle is 3 to 300, including all integer number of display group-functionalized PEG-silane precursors and ranges therebetween. It may be desirable that a protein group, peptide group, oligomer group, nucleic acid group, antibody/antibody fragment group be formed using a PEG group functionalized with a functional group (e.g., using a heterobifunctional PEG precursor or the like).

Co-condensation of PEG-silane and display group-PEG-silanes on a surface of a silica nanoring, it typically carried out at room temperature or about room temperature. The display group-PEG-silane conjugate may be added first, followed quickly by the unfunctionalized PEG-silane. If a display group is a peptide, because of the enhanced affinity of the peptide to the silica surface relative to PEG, a majority of the display group-PEG-silanes adsorb on the silica surface, while the remainder of the surface gets covered with PEG-silane. This adsorption is driven by hydrogen bonding, both of the PEGs and peptides (which have lots of amines and carboxyl-groups, which form hydrogen bonds easily). At this point at room temperature, typically, most of the PEG silanes are not yet covalently bonded to the silica surface. Subsequent to the co-condensation, typically, the temperature of the reaction mixture is increased (e.g., to about 80° C. and the reaction mixture held at this temperature overnight). Without intending to be bound by any particular theory, it is considered that increased temperatures accelerate the condensation reaction of PEG-silane and display group-PEG-silane to the silica surface. At the same time, it significantly weakens the hydrogen bonds, which can make the PEG chains "stand up" on the silica surface, leading to denser PEG coatings, thus improving particle stability. The display group-PEG-silane of the foregoing section may be replaced by or used with a functional group-PEG-silane. Carrying out these processes provides a PEGylated surface or surfaces with additional functional groups on some or all of the PEG chains, which may subsequently be reacted with additional desired display group precursors.

In various examples, a silica nanoring surface or surfaces is/are reacted with one or more heterobifunctional PEG precursor(s), which are then further reacted with a desired complementary chemical functionality on a display group precursor to provide a display group. Reaction of the heterobifunctional PEG precursor(s) with a desired complementary chemical functionality (e.g., reactive group) on a display group precursor may be carried out before or after the heterobifunctional PEG precursors are attached to the silica surface.

A display group precursor comprises a display group and a group that can react with a reactive group of the silica surface (e.g., a display group-silane conjugate or the like) or a reactive group of a functional group, which may be added to or part of the original molecule from which the display group is formed. A display group may be a dye, drug, oligomer, peptide, protein, antibody, antibody fragment, aptamer, chelating group (with or without a metal ion), which may be a radioisotope, nucleic acid, reactive group, or the like or a group derived therefrom.

A display group precursor may react with a reactive group of a silica nanoring to form a display group covalently bound to a surface of the silica nanoring. A functional group precursor comprises a functional group (e.g., a dye group, chelator group, targeting group, drug group, radio label/isotope group, and the like, which may be derived from a dye molecule, chelator molecule, targeting molecule, or the like) and a group that can react with a reactive group of a silica nanoring. Non-limiting examples of groups that react with a reactive group include an amine group, a thiol group, a carboxylic acid group, a carboxylate group, an ester group (e.g., an activated ester group), a maleimide group, an allyl group, a terminal alkyne group, an azide group, a thiocyanate group, and the like, and combinations thereof. In various examples, a functional group precursor comprises one or more group(s) that react in a particular conjugation chemistry or reaction known in the art (e.g., the functional group precursor comprises one or more group(s), such as, for example, an azide or the like, that is complementary to a reactive group of the nanoparticle, such as, for example, a terminal alkyne or the like, in a particular conjugation chemistry/reaction, such as, for example, click chemistry, known in the art). Examples of functional group precursors are known in the art and are commercially available or can be made using methods known in the art.

In various examples, deferoxamine (DFO) is used as a chelator for zirconium-89 radiolabeling for Positron Emission Tomography applications. For example, DFO is conjugated to the silica surface is by first reacting one or more silica surface(s) of the silica nanorings with an amino-silane, and then reacting deferoxamine-Bn-NCS-p (DFO-NCS) with the aminated surface(s). In various examples, targeting peptides (such as, for example, cRGD, alpha-MSH, and the like), are attached via click chemistry to heterobifunctional PEGs (e.g., maleimido-PEG-active esters, and the like) first, which are then in a subsequent step conjugated to the unfunctionalized silica surface in a PEGylation step.

In various examples, a silica nanoring surface or surfaces is/are functionalized by post-PEGylation surface modification by insertion (PPSMI). This functionalization is carried out after PEGylation. This process comprises reacting a silane precursor with a functional group (e.g., an amine group, a thiol group, or the like) with one or more remaining silanol group(s) on a silica surface or surfaces. These silane precursors are of a size that allows the silane precursor to react with the PEGylated surface/surfaces. Subsequently, the functional groups are reacted with a display group precursor comprising one or more complementary functional group(s) (for example an activated ester in the case of the amine, or a maleimido group in case of the thiol) to form display groups forming a surface or surfaces with PEG groups and display groups. An advantage of PPSMI is that reaction conditions do not need to be optimized for each reaction of a display group precursor/functional group, as the silica nanorings are stabilized by the PEG groups (which may be referred to as steric stabilization) and are not sensitive to the particular functionalization chemistry.

In an example, a PEGylated silica nanoring (which may be a fluorescent PEGylated silica nanoring) is reacted with one or more display group precursor(s) and/or one or more functional group precursor(s). The reactions may be carried out in any order. In an example, the silica nanoring is first reacted with at least one display group precursor. For example, a silica nanoring with a single kind of reactive group is reacted with one or more functional group precursor(s). In another example, a silica nanoring with two or more structurally and/or chemically different reactive groups (e.g., 2, 3, 4, or 5 structurally and/or chemically different reactive groups) is reacted with two or more different display group precursors (e.g., 2, 3, 4, or 5 structurally different functional group precursors), where the individual reactive groups/functional group precursors may have orthogonal reactivity.

For example, before or after (e.g., 20 seconds to 5 minutes before or after) the PEG-silane conjugate is added, a PEG-silane conjugate comprising a display group (e.g., at concentration of 0.05 mM to 2.5 mM) is added at room temperature to the reaction mixture comprising the silica nanorings, respectively. The resulting reaction mixture is held at a time and temperature (e.g., 0.5 minutes to 48 hours at room temperature up to 100° C.), where at least a portion of the PEG-silane conjugate molecules are adsorbed on at least a portion of the surface of the silica nanorings. Subsequently, the reaction mixture is heated at a time and temperature (e.g., 0.5 minutes to 48 hours at 40° C. to 100° C.), where silica nanorings surface functionalized with PEG groups and PEG groups comprising a display group are formed. Optionally, subsequently adding at room temperature to the resulting reaction mixture comprising silica nanorings surface functionalized with PEG groups comprising a display group a PEG-silane conjugate (the concentration of PEG-silane display group is 10 mM and 75 mM) (e.g., PEG-silane conjugate dissolved in a polar aprotic solvent such as, for example, DMSO or DMF), holding the resulting reaction mixture at a time and temperature (e.g., 0.5 minutes to 48 hours at room temperature to 100° C.) (whereby at least a portion of the PEG-silane conjugate molecules are adsorbed on at least a portion of the surface of the silica nanorings surface functionalized with PEG groups comprising a display group, and heating the resulting mixture from at a time and temperature (e.g., 0.5 minutes to 48 hours at 40° C. to 100° C.), whereby silica nanorings surface functionalized with PEG groups and PEG groups comprising a display group are formed.

In another example, at least a portion of or all of the PEG-silane has a reactive group on a terminus of the PEG group opposite the terminus conjugated to the silane group of the PEG-silane conjugate (is formed from a heterobifunctional PEG compound) and after formation of the silica nanorings surface functionalized with PEG groups having a reactive group. Optionally, PEG groups are reacted with a second display group (which can be the same or different than the display group of the silica nanoring surface functionalized with PEG groups and PEG group comprising a display group) functionalized with a second reactive group (which can be the same or different than the reactive group of the silica nanoring surface functionalized with PEG groups and PEG group comprising a display group) thereby forming silica nanorings surface functionalized with PEG groups functionalized with a second display group and, optionally, PEG groups.

In another example, at least a portion of or all of the PEG-silane has a reactive group on a terminus of the PEG group opposite the terminus conjugated to the silane group of the PEG-silane conjugate (is formed from a heterobifunctional PEG compound) and after formation of the silica nanorings surface functionalized with PEG groups and, optionally having a reactive group, and, optionally, PEG groups, silica nanoring surface functionalized with PEG groups having a reactive group, and, optionally, PEG groups, are reacted with a second display group (which can be the same or different than the display group of the silica nanorings surface functionalized with PEG groups and PEG group comprising a display group) functionalized with a second reactive group (which can be the same or different than the reactive group of the silica nanorings surface functionalized with PEG groups and PEG group comprising a display group) thereby forming silica nanorings surface functionalized with PEG groups functionalized with a second display group and, optionally, PEG groups, where at least a portion of the PEG-silane has a reactive group on a terminus of the PEG group opposite the terminus conjugated to the silane group of the PEG-silane conjugate (is formed from a heterobifunctional PEG compound) and after formation of the silica nanorings surface functionalized with PEG groups having a reactive group or silica nanorings surface functionalized with PEG groups having a reactive group and PEG groups comprising a display group are reacted with a second display group functionalized with a reactive group (which can be the same or different than the display group of the silica nanorings surface functionalized with PEG groups and PEG group comprising a display group) thereby forming silica nanorings surface functionalized with PEG groups and PEG groups functionalized with a second display group or silica nanorings surface functionalized with PEG groups comprising a display group, or silica nanorings functionalized with PEG groups and PEG groups comprising a display group that is functionalized with the second display group.

The silica nanorings with PEG groups functionalized with reactive groups may be further functionalized with one or more display group(s). For example, a functionalized display group can be reacted with a reactive group of a PEG group. Examples of suitable reaction chemistries and conditions for post-synthesis functionalization of the silica nanorings are known in the art.

The silica nanorings may be functionalized. The silica nanorings can be functionalized using various methods. At least a portion of a surface (e.g., at least a portion of an outer surface (which may be an exterior surface) and/or at least a portion of an inner surface of the silica nanorings may be functionalized (e.g., covalently functionalized and/or non-covalently functionalized).

In various examples, a plurality of silica nanorings is reacted to form an average of 3 to 300 display groups, including all integer number of display groups and ranges therebetween, covalently or non-covalently bound to a surface of each of the silica nanorings.

The silica nanorings may be selectively functionalized. The functionalization may be the same for the inner surface and outer surface of the silica nanorings or may be different for the inner surface and outer surface of the silica nanorings. The silica nanorings may be selectively functionalized by functionalizing the outer surface of the silica nanorings while the micelle is disposed in the inner of the silica nanoring and subsequently functionalizing the inner of the silica nanoring after removal of the micelle. Any one or more of or all of the functionalization reactions may be carried out before and/or after the surfactant(s) and/or pore expander(s) (e.g., micelles) are removed from the nanorings.

The surfactant(s) and/or pore expander(s) (e.g., micelles) may be removed from the silica nanorings at various points of the reaction. For example, the surfactant(s) and/or pore expander(s) (e.g., micelles) are removed to allow surface specific functionalization, which may be orthogonal functionalization. For example, the surfactant(s) and/or pore expander(s) (e.g., micelles) are removed from the silica nanorings by dialysis. For example, after synthesis of the nanorings or at least partially functionalized nanorings, the solution of nanorings is cooled to room temperature and then transferred into a dialysis membrane tube (e.g., a dialysis membrane tube having a molecular weight cut off of 10,000, which are commercially available (e.g., from Pierce), or the like). The solution in the dialysis tube is dialyzed in a solvent mixture of DI-water, ethanol, and acetic acid at a volume ratio of 500:500:1 to 500:500:50 (volume of solvent is 50 times more than the reaction volume, e.g., 500 mL water for a 10 mL reaction). The washing solvent is changed every day for one to six days to extract surfactant(s) and/or pore expander(s) from the interior of the rings and wash away remaining reagents e.g., ammonium hydroxide, surfactant, oil, and free silane molecules. The solution in the dialysis tube is then dialyzed in DI-water (volume of water is 200 times more than the reaction volume, e.g., 2000 mL water for a 10 mL reaction) and the water is changed every day for one to six days to wash away reagents ethanol and acetic acid.

In various examples, after synthesis of the nanorings and before the dialysis step removing the micelles, the micelles inside the ring aperture are covering the inner surface of the silica nanorings. Surface functionalization (which may be PEGylation) in the presence of silica nanorings that include the micelles exclusively surface functionalizes the outer nanoring surface. Functionalization may be carried out using heterobifunctional PEG-silane conjugates that carry, for example, a targeting group (e.g., a peptide group/groups, antibody group/groups, or the like) or with mixtures of heterobifunctional PEG-silane conjugate(s) and PEG-silane conjugate(s), to control the density of the targeting groups on the outer surface of the nanorings. After this outer surface functionalization (which may be PEGylation), the micelles are removed via dialysis, rendering inner surface of the rings accessible. Subsequent surface functionalization (which may be PEGylation) is preferentially directed to the inner surface of the rings (as the outer surface is already functionalized. The inner surface may be functionalized with, for example, PEG group(s), drug group(s), chelator group(s) (which may be used to functionalize the nanorings with radiometals, or a combination thereof. The PEG-silane conjugates for functionalization of the outside surface of the nanorings may comprise PEG groups with 6-9 EO groups and/or the PEG-silane conjugates for functionalization of the inner surface of the nanorings may comprise PEG groups with 3 EO groups.

Various conjugation chemistries/reactions may be used to covalently link a functional group to the surface of a silica nanoring. Accordingly, a functionalizing precursor can comprise various reactive groups. Numerous suitable conjugation chemistries and reactions are known in the art. In various examples, a reactive group is one that reacts in particular conjugation chemistry or reaction known in the art and the functional group precursor comprises a complementary group of the particular conjugation chemistries/reactions known in the art. In various examples, the conjugation chemistry/reaction is click chemistry/reaction.

Functional group precursors may comprise one or more reactive group(s) and a group (e.g., a silane group or the like) that can react with the surface of the silica nanoring to form a covalent bond. The reactive group(s) can react with a functional group precursor to form a functional group that is covalently bound to the surface of the silica nanoring. Non-limiting examples of reactive groups include an amine group, a thiol group, a carboxylic acid group, a carboxylate group, an ester group (e.g., an activated ester group), a maleimide group, an allyl group, a terminal alkyne group, an azide group, a thiocyanate group, and the like, and combinations thereof. Examples of functionalizing precursors are known in the art and are commercially available or can be made using methods known in the art.

In various examples, a display group precursor or functional group precursor comprises a silane group that comprises one or more —Si—OR group(s) (e.g., 1, 2, or 3 Si—OR groups), where R is an alkyl group (e.g., a $C_1$, $C_2$, $C_3$, or $C_4$ alkyl group), and at least one reactive group (e.g., 1, 2, or 3 reactive groups). The silane group(s) and reactive group(s) may be covalently bonded directly or via a linking group such as, for example, an alkyl group (e.g., a $C_1$, $C_2$, $C_3$, $C_4$, $C_5$, or $C_6$ alkyl group). Without intending to be bound by any particular theory, it is considered that the Si—OH group of the functionalizing precursor reacts with a surface hydroxyl group of the silica nanoring (e.g., a surface Si—OR group).

A silica nanoring or a plurality of silica nanorings may be reacted to form various numbers of display groups and/or functional groups. Determining reaction conditions (e.g., reactant concentrations, reaction time, reaction temperature, or the like, or a combination thereof) to form a desired number of group(s) and/or functional group(s) is within the purview of one having skill in the art.

The silica nanorings may be subjected to post-synthesis processing steps. For example, after synthesis, the solution is cooled to room temperature and then transferred into a dialysis membrane tube (e.g., a dialysis membrane tube having a molecular weight cut off of 10,000, which are commercially available (e.g., from Pierce)). The solution in the dialysis tube is dialyzed in a solvent mixture of DI-water, ethanol, and acetic acid at a volume ratio of 500:500:1 to 500:500:50 (volume of solvent is 50 times more than the reaction volume, e.g., 500 mL water for a 10 mL reaction). The washing solvent may be changed every day for one to six days to extract surfactant molecules and/or pore expander molecules from the aperture of the silica nanorings and wash away remaining reagents (e.g., ammonium hydroxide, surfactant, oil, and free silane molecules). The solution in the dialysis tube may then be dialyzed in DI-water (volume of water is 200 times more than the reaction volume, e.g., 2000 mL water for a 10 mL reaction) and the water is changed every day for one to six days to wash away remaining reagents, e.g., ammonium hydroxide and free silane molecules. The particles are then filtered through a 200 nm syringe filter (Fisher Brand) to remove aggregates or dust. If desired, additional purification processes, including gel permeation chromatography and high-performance liquid chromatography, can be applied to the silica nanorings to further ensure the high purify of the synthesized particles (e.g., 1% or less unreacted reagents or aggregates). After any purification processes, the purified silica nanorings can be transferred back to deionized water if other solvent is used in the additional processes.

In a non-limiting examples, a method comprises, before or after the PEG-silane conjugate is added, if a PEG-silane is added, adding a PEG-silane conjugate comprising a display group at room temperature to the reaction mixture, holding the resulting reaction mixture at a time (e.g., $t^2$) and temperature (e.g., $T^2$), subsequently heating the resulting reaction mixture at a time (e.g., $t^3$) and temperature (e.g., $T^3$), whereby silica nanorings surface functionalized with PEG groups comprising a display group are formed.

In other non-limiting examples, at least a portion of or all of the PEG-silane has a reactive group on a terminus of the PEG group opposite the terminus conjugated to the silane group of the PEG-silane conjugate and after formation of the silica nanorings surface functionalized with PEG groups having a reactive group, and, optionally, PEG groups, are reacted with a second display group functionalized with a second reactive group thereby forming silica nanorings surface functionalized with PEG groups functionalized with a second display group and, optionally, PEG groups.

In still other examples, at least a portion of or all of the PEG-silane has a reactive group on a terminus of the PEG group opposite the terminus conjugated to the silane group of the PEG-silane conjugate and after formation of the silica nanorings surface functionalized with PEG groups and, optionally having a reactive group, and, optionally, PEG groups, are reacted with a second display group functionalized with a second reactive group thereby forming silica nanorings surface functionalized with PEG groups functionalized with a second display group and, optionally, PEG groups, A method may comprise one or more isolation/separation process(es). A isolation/separation process or processes may be carried out during silica nanoring synthesis or after the silica nanoring synthesis is complete. Non-limiting examples of isolation/separation processes include size dialysis, exclusion chromatography, high performance liquid chromatography, gel permeation chromatography, and combinations thereof. Using one or more isolation/separation process(es) at least a portion (or all) of the silica nanorings are isolated from the reaction mixture (e.g., unreacted precursor(s) or the like).

The isolation/purification of the nanorings may comprise dialysis. For example, after synthesis of the nanorings or at least partially functionalized nanorings, the solution of nanorings is cooled to room temperature and then transferred into a dialysis membrane tube (e.g., a dialysis membrane tube having a molecular weight cut off of 10,000, which are commercially available (e.g., from Pierce)). The solution in the dialysis tube is dialyzed in a solvent mixture of DI-water, ethanol, and acetic acid at a volume ratio of 500:500:1 to 500:500:50 (volume of solvent is 50 times more than the reaction volume, e.g., 500 mL water for a 10 mL reaction). The washing solvent is changed every day for one to six days to extract surfactant(s) and/or pore expander(s) from the interior of the rings and wash away remaining reagents e.g., ammonium hydroxide, surfactant, oil, and free silane molecules. The solution in the dialysis tube is then dialyzed in DI-water (volume of water is 200 times more than the reaction volume, e.g., 2000 mL water for a 10 mL reaction) and the water is changed every day for one to six days to wash away reagents ethanol and acetic acid. In various examples, after synthesis the nanorings are transferred into a dialysis membrane (MWCO 10 k). Then, the sample is dialyzed in 200 mL of ethanol/deionized water/glacial acetic acid solution (500:500:7 volume ratio), and the acid solution is changed once a day for 3 days to remove/etch the surfactant(s) and pore expander(s) from the interior of the silica nanorings (micelle removal) and to remove unreacted reagents from the sample, if present.

In the case of reaction mixtures comprising polymerizable pore expander molecules, the polymerizable pore expander molecules may be polymerized to form silica nanoring composites. The polymerizable pore expander molecules may be polymerized by methods known in the art. For example, the polymerization can be carried out by use of a water insoluble radical initiator that generates radicals via heating or illumination with light (typically UV light) which in turn initiates the radical polymerization.

The methods can provide silica nanoring may have various sizes. The silica nanorings may have a size (or average size), which may be a longest linear dimension (or average longest linear dimension), such as, for example, an outer diameter (or average outer diameter), of 20 nm or less. The size or average size may or may not include any surface functional groups of a silica nanoring. In various examples, the size or average size of all of the silica nanorings in a batch (silica nanorings formed in a single reaction) is within 30% or less of the average size, 25% of the average size, 20% or less of the average size, 15% or less of the average size, or 10% or less of the average size. For the exemplary size distributions, the silica nanorings may not have been subjected to any particle-size discriminating (size selection/removal) processes (e.g., filtration, dialysis, chromatography (e.g., GPC), centrifugation, or the like).

Without intending to be bound by any particular theory, it is considered that the average size of a batch (silica nanorings formed in a single reaction) can be selected by selecting on or more of the reaction components, ratio of two or more reaction components, reaction conditions, or the like. As an illustrative example, the size of the silica nanorings, typically, when all other things being the same, increases when the surfactant:pore expander molar ratio decreases.

In an aspect, the present disclosure provides methods of characterizing silica nanorings. In various examples, silica nanorings and/or functionalized silica nanorings (which may be present in a composition) are characterized by high performance liquid chromatography (HPLC). In various examples, preparative HPLC, which may be preparative scale HPLC, is used to isolate one or more nanoring(s), some or all of which may be functionalized nanoring(s), from a mixture of such nanoring(s), which may be a reaction mixture. HPLC methods described herein may be used to determine an effective loading capacity of the inner surface of the silica nanorings.

Figure 10:
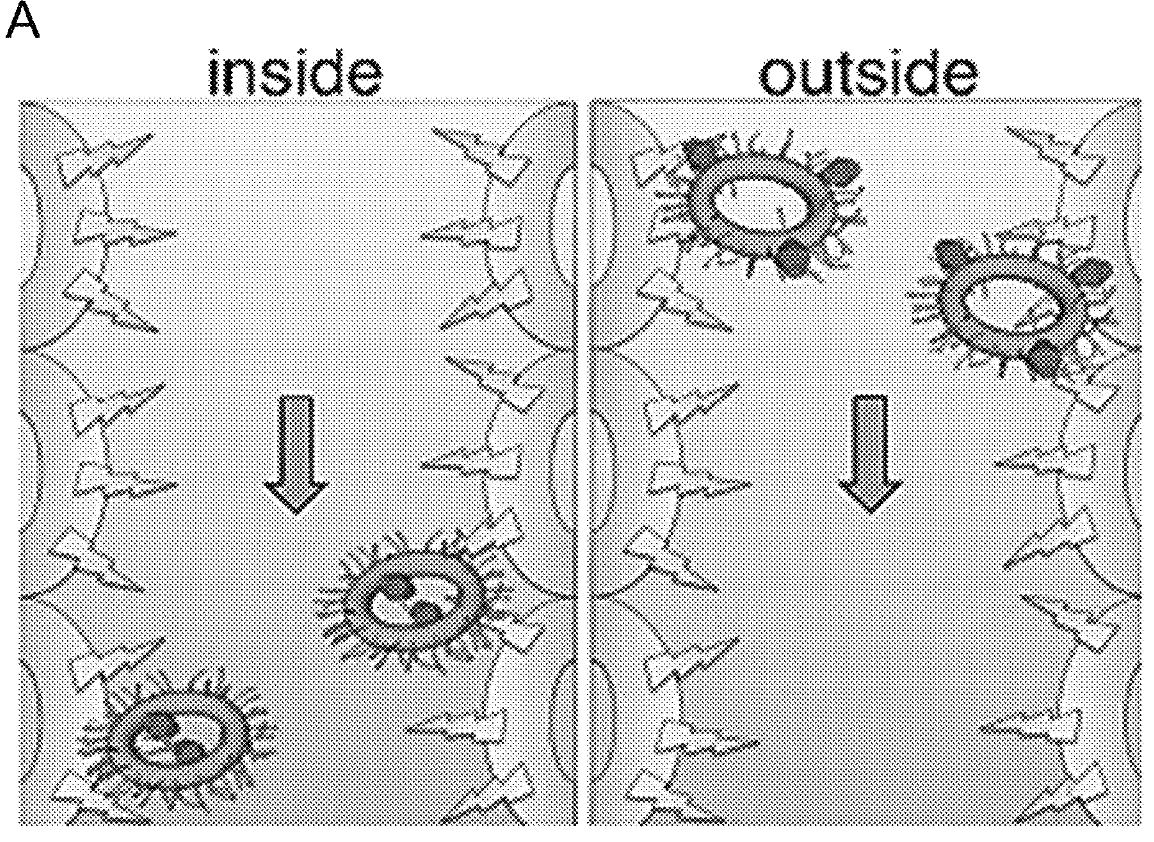
FIG. 10 shows (a) a graphical representation of how nanorings functionalized on the inside (inner) surface (left side in (a)) as compared to the outside (outer) surface (right side in (a)) interact less with the HPLC column material and therefore pass faster through the HPLC column. (b) A graphical representation of how this behavior in (a) translates into different elution times from the HPLC column. Therefore, HPLC allows differentiating between inner and outer nanoring functionalization.
Figure 10:
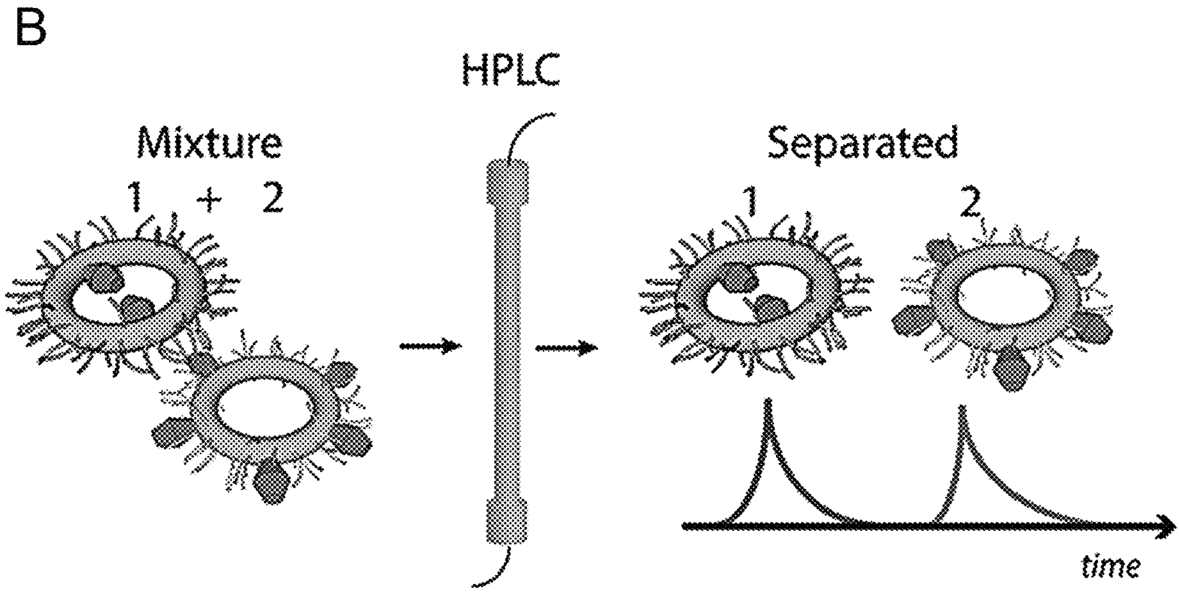

High performance liquid chromatography (HPLC) may be used to determine the location of display groups functionalized on the surface of the silica nanorings. See, e.g., FIG. 10. That is, HPLC may be used to determine whether display groups are located on the inner surface, outer surface, or both surfaces of a silica nanoring.

HPLC methods described herein may be used to identify and/or separate nanorings selectively surface functionalized on the inner and/or outer surface of a single batch of silica nanorings. Such methods may be used to develop of synthetic protocols that allow hitherto inaccessible surface selective functionalization of silica nanorings.

In an aspect, the present disclosure provides uses of silica nanorings. In various examples, silica nanorings or a composition comprising silica nanorings are used in delivery and/or imaging methods.

The display groups functionalized to the silica nanorings may include diagnostic and/or therapeutic agents (e.g., drugs and the like). Examples of therapeutic agents include, but are not limited to, chemotherapeutic agents, antibiotics, antifungal agents, antiparasitic agents, antiviral agents, and combinations thereof. An affinity display group may be also be conjugated to the silica nanorings to allow targeted delivery of the silica nanorings. For example, the silica nanorings is conjugated to a display group capable of binding a cellular component (e.g., on the cell membrane or in the intracellular compartment) associated with a specific cell type. The targeted molecule may be a tumor marker or a molecule in a signaling pathway. The display group can have specific binding affinity to certain cell types, such as, for example, tumor cells. In certain examples, the display group may be used for guiding the silica nanorings to specific areas, such as, for example, liver, spleen, brain or the like. Imaging can be used to determine the location of the silica nanorings in an individual.

The silica nanorings or compositions comprising silica nanorings may be administered to individuals for example, in pharmaceutically-acceptable carriers, which facilitate transporting the silica nanorings from one organ or portion of the body to another organ or portion of the body. Examples of individuals include animals such as, for example, human and non-human animals. Examples of individuals also include mammals.

Compositions comprising the present silica nanorings can be administered to an individual by any suitable route—either alone or in combination with other agents. Administration can be accomplished by any means, such as, for example, by parenteral, mucosal, topical, catheter-based, or oral means of delivery, or the like. Parenteral delivery can include, for example, subcutaneous, intravenous, intramuscular, intercranial, intra-arterial delivery, which may be injection into the tissue of an organ. Mucosal delivery can include, for example, intranasal delivery. Catheter-based delivery can include delivery by iontophoretic catheter-based delivery. Oral delivery can include delivery of an enteric coated pill, or administration of a liquid by mouth. Transdermal delivery can include delivery via the use of dermal patches.

Following administration of a composition comprising the present silica nanorings, the path, location, and clearance of the silica nanorings can be monitored using one or more imaging technique(s). Imaging may be used to determine the location of the silica nanorings in an individual Examples of suitable imaging techniques include fluorescence imaging (e.g., using the Artemis Fluorescence Camera System or the like) or positron emission tomography (PET) when using a radiolabel attached to the silica nanorings. In various examples, a combination of imaging techniques is used. It may be desirable to use PET to image a portion of or all of an individual.

The present disclosure provides methods for imaging (which may be optical imaging methods, such as, for example, fluorescence imaging methods and the like, PET and the like) biological materials, such as, for example, cells, extracellular components, or tissues comprising contacting the biological material with silica nanorings comprising one or more dye group(s), or compositions comprising the silica nanorings; directing excitation electromagnetic (e/m) radiation, such as, for example, light, on to the tissues or cells thereby exciting the dye groups; detecting e/m radiation emitted by the excited dye group(s); and capturing and processing the detected e/m radiation to provide one or more image(s) of the biological material. One or more of these steps can be carried out in vitro or in vivo. For example, the cells or tissues can be present in an individual or can be present in culture. Exposure of cells or tissues to e/m radiation can be effected in vitro (e.g., under culture conditions) or can be effected in vivo. For directing e/m radiation at cells, extracellular materials, tissues, organs and the like within an individual or any portion of an individual's body that are not easily accessible, fiber optical instruments can be used.

For example, a method for imaging of a region within an individual comprises (a) administering to the individual silica nanorings or a composition of the present disclosure comprising one or more dye group(s); (b) directing excitation light into the individual, thereby exciting at least one of the one or more dye groups(s); (c) detecting excited light, the detected light having been emitted by the dye group(s) in the individuals as a result of excitation by the excitation light; and (d) processing signals corresponding to the detected light to provide one or more image(s) (e.g., a real-time video stream) of the region within the individual. In another example, in the case were at least a portion of or all of the administered nanorings comprise one or more radioisotope(s), the method of imaging comprises PET imaging, which may be in combination with fluorescence imaging (e.g., as described in the example of imaging above) or in the absence of fluorescence imaging.

For example, a drug-linker conjugate, where the linker group can be specifically cleaved by an enzyme, reduction (e.g., of a disulfide bond or the like), or an acid condition in a tumor for drug release, can be covalently attached to the functional display groups on the particles for drug delivery. For example, drug-linker-thiol conjugates can be attached to maleimido-PEG-particles through thiol-maleimido conjugation reaction post the synthesis of maleimido-PEG-particles. Additionally, both drug-linker conjugate and cancer targeting peptides can be attached to the nanoring surface for drug delivery specifically to tumor.

The silica nanorings or compositions comprising silica nanorings may be administered to individuals for example, in pharmaceutically-acceptable carriers, which facilitate transporting the silica nanorings from one organ or portion of the body to another organ or portion of the body. Examples of individuals include animals such as, for example, human and non-human animals. Examples of individuals also include mammals.

Because the fluorescent silica nanorings are brighter than free dye, fluorescent silica nanorings can be used for tissue imaging, as well as to image metastatic tumors. Additionally or alternatively, radioisotopes can be further attached to the display group groups (e.g., tyrosine residue or chelator, and the like) of the display group-functionalized silica nanorings or to the silica matrix of the PEGylated particles without specific display group functionalization for PET imaging. If the radioisotopes are chosen to be therapeutic, such as, for example, $^{225}$Ac, $^{177}$Lu, and the like, this in turn would result in silica nanorings with additional radiotherapeutic properties.

The present disclosure provides methods of using one or more silica nanoring(s) and/or one or more composition(s) comprising administering one or more silica nanoring(s) to treat cancer. Examples of cancers, include but are not limited to, lung cancer, dermatological cancer, premalignant lesions of the upper digestive tract, malignancies of the prostate, malignancies of the brain, malignancies of the breast, and the like, and combinations thereof). A method may be carried out in combination with one or more known therapy (ies). Non-limiting examples of known therapies include other agents used to treat cancer (such as, for example, drugs, which may be chemotherapeutic drugs), immunotherapy, radiation, surgery, and the like. A method may be carried out in conjunction with an imaging method. In various examples, a method of treating cancer is carried out in conjunction with an imaging method of the present disclosure.

Various cancers may be treated via a method of the present disclosure. Non-limiting examples of cancers include leukemia, lung cancer (e.g., non-small cell lung cancer and the like), dermatological cancers, premalignant lesions of the upper digestive tract, malignancies of the prostate, malignancies of the brain, malignancies of the breast, solid tumors, and the like, and combinations thereof. In various examples, one or more silica nanoring(s) and/or one or more composition(s) comprising one or more silica nanoring(s) described herein is administered to an individual in need of treatment using any known method and route, including, but not limited to, parenteral, mucosal, topical, catheter-based, oral, or transdermal means of delivery, or the like.

Compositions comprising silica nanorings can be administered to an individual by any suitable route—either alone or in combination with other agents. Administration can be accomplished by any means as described herein.

A method can be carried out in an individual in need of treatment who has been diagnosed with or is suspected of having cancer. A method can also be carried out in an individual who have a relapse or a high risk of relapse after being treated for cancer.

An individual in need of treatment may be a human or non-human mammal or other animal. Non-limiting examples of non-human mammals include cows, pigs, mice, rats, rabbits, cats, dogs, or other agricultural mammals, pets, or service animals, and the like.

In various examples, silica nanorings are used in a therapeutically effective amount (e.g., administered to an individual in need of treatment). The term "therapeutically effective amount" as used herein refers to an amount of an agent sufficient to achieve, in a single or multiple doses, the intended purpose of treatment. Treatment does not have to lead to complete cure, although it may. Treatment may mean alleviation of one or more of the symptom(s) (e.g., may at least shrink a solid tumor) and/or marker(s) of the indication. The exact amount desired or required will likely vary depending on the particular silica nanoring(s) or composition(s) used, its mode of administration, patient specifics, and the like. An appropriate effective amount may be determined by one of ordinary skill in the art informed by the instant disclosure using only routine experimentation. Treatment can be affected over a short period, over a medium term, or can be a long-term treatment, such as, for example, within the context of a maintenance therapy. Treatment can be continuous or intermittent.

The silica nanorings may exhibit desirable renal clearance. In various examples, the silica nanorings to do not exhibit substantial uptake in one or more of an individual's organ(s) of the reticuloendothelial system (RES), such as, for example, liver, spleen, or the like, or a combination thereof. By substantial uptake it is meant that less than 10% of the nanorings, less than 5% of the nanorings, less than 1% of the nanorings, less than 0.1% of the nanorings are observed in an individual's organ(s), such as, liver, spleen, or the like, or a combination thereof, 3 days or more, 5 days or more, or 7 days or more days after administration of the silica nanorings. The presence and/or absence of nanorings in an individual's organ(s) can be determined by imaging methods. In various examples, the presence and/or absence of nanorings in one or more of individual's organ(s) is determined by positron emission tomography (PET), optical imaging methods, or the like, or a combination thereof, examples of which are provided herein. Without intending to be bound by any particular theory, it is considered that the uptake of silica nanorings is correlated with the diffusion coefficient of the nanorings.

In an aspect, the present disclosure provides kits. In various examples, a kit comprises one or more silica nanoring(s) and/or one or more composition(s) of the present disclosure. In an example, a kit comprises a closed or a sealed package that contains the silica nanoring(s) and/or the composition(s). In certain examples, the package can comprise one or more closed or sealed vial(s), bottle(s), blister (bubble) pack(s), or any other suitable packaging for the sale, or distribution, or use of the silica nanoring(s) and/or the composition(s). The printed material can include printed information. The printed information may be provided on a label, or on a paper insert, or printed on the packaging material itself. The printed information may include information that identifies the some or all of the contents of the package, the amounts and types of other active and/or inactive ingredients, and instructions for taking the composition, such as, for example, the number of doses to take over a given period of time, and/or information directed to a pharmacist and/or another health care provider, such as, for example, a physician, or a patient. The printed material may include an indication that the silica nanoring(s) and/or the composition(s) with it is for treatment and/or diagnosis of an individual having cancer. In various examples, the kit includes a label describing the contents of the container and providing indications and/or instructions regarding use of the contents of the container to treat and/or diagnose an individual having cancer.

The steps of the methods described in the various embodiments and examples disclosed herein are sufficient to carry out the methods of the present disclosure. Thus, in various examples, a method consists essentially of a combination of the steps of the methods disclosed herein. In various other examples, a method consists of such steps.

The following Statements provide examples of silica nanorings, methods making silica nanorings, and uses of silica nanorings of the present disclosure:

Statement 1. A silica nanoring defining a single aperture (e.g., a nanoring with a single pore, which may be a mesopore) and comprising a first surface at a largest circumference of the silica nanoring (which may be an outer surface) and a second surface proximal to the aperture (which may be an inner surface), wherein at least a portion of or substantially all of a surface (e.g., a first surface or outer surface), or at least a portion of or substantially all of a second surface (or inner surface), or all of the surfaces of the silica nanoring are functionalized with PEG groups, functionalized PEG groups, or a combination thereof, and at least a portion of or all the silica matrix of the silica nanoring is microporous. By substantially all, it is meant that the surface(s) of the silica nanoring have the maximum number of PEG groups and/or functionalized PEG groups that can be conjugated to the surface(s) (e.g., using a method of the present disclosure). The silica matrix may have modulated thickness (e.g., one or more modulated dimension normal to a long axis of the silica matrix). In various examples, the silica matrix has a modulated diameter, modulated radius, or the like. In various examples, the silica matrix has a plurality of silica domains, where at least two domains (which may referred to as first domains) are connected (e.g., covalently bonded by a plurality of Si—O—Si bonds) by a silica domain (which may be referred to as a second silica domain) and this domain (e.g., second silica domain) has a dimension normal to a long axis of the silica matrix that is 50% or less (e.g., 10-50%, including all 0.1% values and ranges therebetween) than a dimension normal to a long axis of the silica matrix of one or both of the two domains (e.g., first domain(s)).

Statement 2. The silica nanoring of Statement 1, having a size (e.g., a hydrodynamic size or size determined by transmission electron microscopy (TEM)) (which may be longest dimension (e.g., a longest linear dimension, such as, for example, an outside diameter)) of 5 nm to 20 nm (e.g., 5 nm to 8 nm, 5 nm to 20 nm, 7 nm to 15 nm, or 9 nm to 12 nm), including every 0.1 nm value and range there between.

Statement 3. The silica nanoring of Statement 1 or 2, wherein the single aperture (e.g., the single pore) of the silica nanoring has a size (which may be a linear dimension (e.g., a longest linear dimension, such as, for example, an inside diameter of the silica nanoring) of 3 nm to 13 nm, including every 0.1 nm value and range therebetween.

Statement 4. The silica nanoring of any one of the preceding Statements, wherein the at least a portion or substantially all or all of the first (e.g., outer surface) and/or at least a portion or substantially all or all of the second surface (e.g., inner surface) is functionalized with one or more display group(s) (which may be referred to as or be ligands) chosen from peptide groups (e.g., targeting peptide groups, such as, for example, cRGDyC groups, α-MSH groups, PSMAi groups, and the like, and combinations thereof), nucleic acid groups (e.g., RNA groups, DNA groups, and the like, and combinations thereof), antibody groups, antibody fragment groups, dye groups, metal chelating groups, radiolabels (e.g., $^{89}Zr$, $^{124}I$, and the like), radiotherapeutics (e.g., $^{225}Ac$, $^{177}Lu$, and the like), therapeutic drugs and drug-linker groups, sensor groups, functional chemical groups, and the like, and combinations thereof.

Statement 5. The silica nanoring of any one of the preceding Statements, wherein the silica nanoring comprises more than one display group and at least a portion of the display groups are structurally distinct.

Statement 6. The silica nanoring of claim 1, wherein the at least a portion of or all of the outer surface is functionalized with PEG groups, some or all of which may be functionalized PEG groups, independently at each occurrence comprising 6, 7, 8, or 9 ethyleneoxide groups and, optionally, one or more drug(s) groups, at least a portion of or all of the inner surface is functionalized with PEG groups independently at each occurrence comprising 2, 3, or 4 ethylene oxide groups and optionally, one or more drug(s), and the silica matrix of the nanoring having (comprising) a plurality of fluorescent groups covalently bound to the silica matrix. The nanoring may further comprise one or more additional display group(s).

Statement 7. The silica nanoring of any one of the preceding Statements, wherein the silica nanoring is used as a diagnostic agent (e.g., an imaging agent), drug delivery agent, as a therapeutic agent, a theranostic agent (e.g., acts as both a diagnostic agent and a drug delivery/therapeutic agent), or the like, or a combination thereof.

Statement 8. A composition comprising a plurality of silica nanorings (e.g., silica nanorings of the present disclosure, such as, for example, silica nanorings of any one of Statements 1-7 and/or silica nanoring(s) made by a method of any one of Statements 11-23).

Statement 9. The composition of Statement 8, wherein the composition comprises two or more structurally distinct silica nanorings.

Statement 10. The composition of Statement 8 or 9, the composition further comprising one or more pharmaceutical carrier(s).

Statement 11. A method of making silica nanorings (e.g., silica nanorings of the present disclosure, such as, for example, silica nanorings of any one of Statements 1-7) comprising: forming a reaction mixture comprising: one or more silica precursor(s); one or more surfactant(s) (e.g., a surfactant including positively charged groups or a surfactant including negatively charged groups); one or more pore expander(s) (e.g., one or more hydrophobic pore expander(s)); and holding the reaction mixture at a time ($t^1$) and temperature ($T^1$), whereby silica nanorings (e.g., silica nanorings having an average size (e.g., an average longest linear dimension, such as for example, an average outer diameter) of 20 nm or less) are formed; and adding a PEG-silane, a PEG-silane conjugate comprising a display group, or a combination thereof to the reaction mixture.

Statement 12. The method of Statement 11, where the one or more surfactant(s) is/are chosen from $C_{10}$ to $C_{18}$ alkyltrimethylammonium halides (e.g., cetyltrimethylammonium bromide (CTAB), decyltrimethylammonium bromide ($C_{10}$TAB), dodecyltrimethylammonium bromide ($C_{12}$TAB), myristyltrimethylammonium bromide ($C_{14}$TAB), octadecyltrimethylammonium bromide ($C_{18}$TAB), and the like), sodium dodecyl sulfate (SDS), N-myristoyl-L-glutamic acid (C14GluA), and combinations thereof, and/or the one or more pore expander(s) is/are chosen from trialkylated benzene (e.g., 1,2,4-trimethylbenzene (TMB), and the like), polymers and polymer monomers (e.g., styrenes, alkylstyrenes (e.g., methyl styrene and the like), and the like and monomers thereof), hydrophobic solvents (e.g., alkanes (e.g., hexane and the like), cycloalkanes (e.g., cyclohexane and the like), benzene, alkylated benzene (e.g., toluene and the like), chlorinated alkanes (e.g., chloroform and the like)), and the like, and combinations thereof.

Statement 13. The method of Statement 11 or 12, wherein the one or more surfactant(s) is/are present in the reaction mixture at a concentration ranging from 1 mg/mL to 50 mg/mL, including all 0.1 mg/mL values and ranges therebetween, and/or the one or more pore expander(s) is/are present at a concentration ranging from 0.05 mg/mL to 150 mg/mL including all 0.1 mg/mL values and ranges therebetween.

Statement 14. The method of any one of Statements 11-13, wherein the molar ratio of the one or more surfactant(s) to the one or more pore expander(s) is 1:2 to 1:10, including all 0.1 ratio values and ranges therebetween.

Statement 15. The method of any one of Statements 11-14, wherein the one or more silica precursor(s) is/are chosen from silica precursors (e.g., tetraalkoxysilanes, such as, for example, tetramethylorthosilicate (TMOS), tetraethylorthosilicate (TEOS), tetrapropylorthosilicate (TPOS), and the like), alkyltrialkoxysilanes (e.g., methyltrimethylorthosilicate and the like), functionalized silica precursors, such as, for example, (3-aminopropyl)triethoxysilane (APTES), (3-aminopropyl)trimethoxysilane (APTMS), (3-mercaptopropyl)trimethoxysilane (MPTMS), and the like), and the like, and combinations thereof.

Statement 16. The method of any one of Statements 11-15, wherein at least a portion of or all of the one or more of the silica precursor(s) comprises one or more display group(s) (e.g., a fluorescent dye group (e.g., is a dye-silane conjugate, such as, for example, DEAC-silane, ATTO647N-silane, and the like) or a peptide group and a fluorescent dye group (e.g., is a peptide-dye-silane conjugate, such as, for example, cRGDY-ATTO647N-silane and the like).

Statement 17. The method of any one of Statements 11-17, further comprising functionalization (e.g., covalently functionalized and/or non-covalently functionalized) at least a portion of a surface (e.g., at least a portion of an outer surface and/or at least a portion of an inner surface of the silica nanorings) of the silica nanorings with one or more display group(s).

Statement 18. The method of any one of Statements 11-18, further comprising removing substantially all or all of the surfactant(s) and/or pore expander(s) (e.g., removing the micelle) from the interior of the silica nanoring. In various examples, substantially all or all of the surfactant(s) and/or pore expander(s) (e.g., the micelle) is/are removed by dialysis of the silica nanorings in acidic solution.

Statement 19. The method of Statement 18, wherein substantially all or all of the surfactant(s) and/or pore expander(s) (e.g., the micelle) are removed (i) before addition of the PEG-silane, the PEG-silane conjugate comprising a display group, or the combination thereof, (ii) or after functionalization of the silica nanoparticle.

Statement 20. The method of any one of Statements 11-19, wherein before or after the PEG-silane is added, adding a PEG-silane conjugate comprising a display group is added at room temperature to the reaction mixture, holding the resulting reaction mixture at a second time ($t^2$) and second temperature ($T^2$), and subsequently heating the resulting reaction mixture at a third time ($t^3$) and third temperature ($T^3$), whereby silica nanorings surface functionalized with PEG groups comprising a display group are formed.

Statement 21. The method of any one of Statements 11-20, wherein at least a portion of or all of the PEG-silane has a reactive group on a terminus of the PEG group opposite the terminus conjugated to the silane group of the PEG-silane conjugate and after formation of the silica nanoring surface functionalized with PEG groups having a reactive group, and, optionally, PEG groups, are reacted with a second display group functionalized with a second reactive group thereby forming silica nanorings surface functionalized with PEG groups functionalized with a second display group and, optionally, PEG groups.

Statement 22. The method of any one of Statements 11-21, wherein the reaction mixture further comprises one or more solvent(s) (e.g., wherein the solvent comprises (or is) water and the pH of the reaction mixture is 6 or greater (e.g., 6-9)).

Statement 23. The method of any one of Statements 11-22, further comprises isolation/separation (e.g., using size exclusion chromatography, high performance liquid chromatography, and gel permeation chromatography) of at least a portion, substantially all, or all of the silica nanorings from the reaction mixture.

Statement 24. A method of determining the location of one or more display group(s) on a silica nanoring of the present disclosure (e.g., silica nanorings of any one of Statements 1-7 and/or silica nanoring(s) made by a method of any one of Statements 11-23) comprising subjecting the silica nanoring to high performance liquid chromatography (HPLC) analysis.

Statement 25. The method of Statement 24, comprising: depositing the silica nanoring in an HPLC column comprising an input in fluid communication with a stationary phase in fluid communication with an output in fluid communication with a detector; passing a mobile phase through the HPLC column, such that the silica nanoring elutes from the column and enters the detector, such that the detector generates a signal, wherein the signal indicates the location of the one or more display group(s) on the silica nanoring; and analyzing the signal to determine the location of the one or more display group(s) on the silica nanoring. The signal may be a fluorescence signal, an ultraviolet-visible light signal, or both.

Statement 26. The method of Statement 25, wherein the signal comprises an elution time and the elution time correlates to the location of one or more display group(s) on the silica nanorings, wherein the location corresponds to the inner and/or outer surface.

Statement 27. The method of Statement 25 or 26, wherein the HPLC column is a reverse phase HPLC (RP-HPLC) column.

Statement 28. The method of any one of Statements 25-27, wherein the stationary phase is a $C_4$ to $C_{18}$ functionalized silica.

Statement 29. The method of any one of Statements 25-28, wherein the mobile phase comprises water.

Statement 30. The method of any one of Statements 29, wherein the mobile phase further comprises acetonitrile.

Statement 31. The method of any one of Statements 29, wherein the mobile phase further comprises methanol and/or isopropanol.

Statement 32. The method of any one of Statements 25-30, further comprising utilizing gel permeation chromatography (GPC).

Statement 33. The method of any one of Statements 25-31, further comprising utilizing fluorescence correlation spectroscopy (FCS) to determine the number of display groups and/or silica nanorings.

Statement 32. A method for purifying a plurality of silica nanorings comprising subjecting the plurality of silica nanorings to liquid chromatography and selecting a portion of the plurality of silica nanorings.

Statement 33. The method of Statement 32, further comprising identifying the selected portion of the plurality of silica nanorings.

Statement 34. The method of Statement 32 or 33, wherein the liquid chromatography comprises: depositing the plurality of silica nanoparticles in a chromatography column comprising an input in fluid communication with a stationary phase in fluid communication with an output in fluid communication with a detector; passing a mobile phase through the chromatography column, such that the plurality of silica nanorings elutes from the column; and collecting an eluent comprising the selected portion of the plurality silica nanorings.

Statement 35. The method of any one of Statements 32-34, wherein the chromatography column is a GPC column.

Statement 36. The method of any one of Statements 32-35, further comprising analyzing the selected portion of the silica nanorings by FCS.

Statement 37. The method of any one of Statements 32-36, further comprising analyzing the selected portion of the plurality of silica nanorings by HPLC.

Statement 38. The method of any one of Statements 32-37, wherein analyzing the selected portion of the plurality of silica nanorings by HPLC comprises collecting a fraction of the eluent comprising the selected portion of plurality of silica nanorings.

Statement 39. The method of any one of Statements 32-38, wherein two or more fractions of the eluent comprising the selected portion of plurality of silica nanorings are combined.

Statement 40. A method for imaging of a region of or within an individual comprising: administering to the individual a plurality of silica nanorings of the present disclosure (e.g., silica nanorings of any one of Statements 1-7 and/or silica nanoring(s) made by a method of any one of Statements 11-23), wherein the silica nanorings comprise one or more dye groups(s), one or more radioisotope groups(s), one or more iodide(s), or the like, or a combination thereof; directing excitation electromagnetic radiation into the individual, thereby exciting at least one of the one or more dye molecule(s), one or more radioisotope(s), or one or more iodide(s), or the like; detecting excited electromagnetic radiation, the detected electromagnetic radiation having been emitted by the one or more dye molecule(s), the one or more radioisotope(s), one or more iodide(s), or the combination thereof, in the individuals as a result of excitation by the excitation electromagnetic radiation; and processing signals corresponding to the detected electromagnetic radiation to provide one or more image(s) of the region within the individual. The silica nanorings may exhibit desirable renal clearance.

Statement 41. A method of Statement 40, wherein the imaging is optical imaging (e.g., fluorescence imaging), PET imaging, CT imaging, or a combination thereof.

Statement 42. A method of treating cancer in an individual comprising administering to the individual a therapeutically effective amount of a composition comprising one or more silica nanoring(s) of the present disclosure (e.g., silica nanorings of any one of Statements 1-7 and/or silica nanoring(s) made by a method of any one of Statements 11-23 or a composition of any one of Statements 8-10), wherein the individual's cancer is treated.

Statement 43. The method of Statement 42, wherein at least a portion of the silica nanoring(s) comprise a drug and at least a portion of the drug is released from the silica nanoring(s) and/or at least a portion of the silica nanoring(s) may comprise a radioisotope (which may result in radiotherapy).

Statement 44. The method of Statement 42 or 43, wherein at least a portion of the silica nanoring(s) comprise one or more display group(s) that target(s) the cancer.

Statement 45. The method of any one of Statements 42-44, further comprising visualization of at least a portion of the cancer using optical imaging (e.g., fluorescence imaging), PET imaging, CT imaging, or a combination thereof.

Statement 46. The method of any one of Statements 42-45, further comprising treatment of the individual with one or more known cancer therapy/therapies in conjunction with administration of the silica nanoring(s) (e.g., before and/or after and/or at the same time as the administration of the silica nanoring(s)).

Statement 47. The method of any one of Statements 42-46, wherein the cancer is chosen from brain cancers, melanomas, prostate cancer, breast cancer, lung cancer, and the like, and combinations thereof. The cancer may be a solid tumor.

Statement 48. The method of any one of Statements 42-47, wherein the individual is a human individual or a non-human individual.

The following examples are presented to illustrate the present disclosure. They are not intended to be in any way limiting.

Example 1

This example provides a description of synthesis and use of nanorings of the present disclosure.

Described in this example are fluorescent silica nanorings that are of particular interest for theranostic applications in nanomedicine. Presented are in-depth studies of the synthesis and orthogonal surface functionalization successfully distinguishing the inside and outside of the silica nanorings, utilizing a combination of spectroscopic and analytical techniques including fluorescence correlation spectroscopy (FCS) and reverse phase high performance liquid chromatography (RP-HPLC, which may be referred to as simply HPLC). Results suggest that despite the small silica ring size around 10 nm and below it is possible to effectively "hide"

hydrophobic moieties on the inside of the rings, however their number must be carefully engineered.

A combination of GPC and HPLC was applied to the characterization of fluorescent silica nanorings, mesoporous nanomaterials with a single pore, as a test bed for attempting to differentiate between inside and outside surfaces of the rings. It was demonstrated that HPLC is a rapid and reliable screening tool capable of differentiating the locations of ligands conjugated to either of the two surfaces of these single-pore objects. Furthermore, a transition regime was observed in which as a function of synthesis conditions the ring's inner pore becomes too crowded resulting in the ligands being pushed more and more out of the inner pore of the rings. For a given dye-ligand model, using HPLC in combination with other characterization techniques including fluorescence correlation spectroscopy (FCS), an upper limit of effective ligand loading to the inner surface of the nanorings was defined. This synthesis and characterization method development, enabling first the orthogonal preparation of such ligand-functionalized single-pore nanomaterials and subsequently the quantitative characterization of the distribution of ligands between inside and outside surfaces of such ultrasmall single-pore SNPs, may be of interest to other NP systems. Furthermore, the specific silica nanorings described herein constitute interesting vehicles for theranostics, i.e. combined therapeutic and diagnostic, applications in nanomedicine in general, and oncology in particular.

Materials and Methods/Experimental Section. Materials. All materials were used as received. 7-diethylaminocoumarin-3-carboxylic acid, succinimidyl ester (DEAC), and tetramethylrhodamine-6 $C_2$ maleimide (TMR) were purchased from Anaspec. Cyanine5 maleimide (Cy5) with net positive charge was purchased from Lumiprobe. Sulfo-Cyanine5 maleimide (sulfo-Cy5) with net negative charge was purchased from Click Chemistry Tools. Hexadecyltrimethyl ammonium bromide (CTAB, ≥99%), tetramethyl orthosilicate (TMOS, ≥99%), 2.0 M ammonium hydroxide in ethanol, and anhydrous dimethyl sulfoxide (DMSO, ≥99%) were purchased from Sigma Aldrich. (3-aminopropyl) trimethoxysilane (APTES), 2-[methoxy (polyethyleneoxy) 6-9propyl] trimethoxysilane (PEG-Silane, 6-9 ethylene glycol units), (3-mercaptopropyl) trimethoxysilane (MPTMS, 95%), and methoxy triethyleneoxy propyl trimethoxysilane (PEG-silane, 3 ethylene glycol units) were obtained from Gelest. Mesitylene (TMB, 99% extra pure) was purchased from Acros Organics. Absolute anhydrous ethanol (200 proof) was purchased from Koptec. Glacial acetic acid was purchased from Macron Fine Chemicals. 5.0 M sodium chloride irrigation USP solution was purchased from Santa Cruz Biotechnology. Syringe filters (0.2 μm, PTFE membrane) were purchased from VWR International. Vivaspin sample concentrators (MWCO 30K) and Superdex 200 prep grade were obtained from GE Health Care. Snakeskin dialysis membrane (MWCO 10K) was purchased from Life Technologies. Deionized (DI) water was generated using Millipore Milli-Q system (18.2 MΩ·cm). Glass bottom microwell dishes for FCS were obtained from MatTek Corporation. Carbon film coated copper grids for TEM was purchased from Electron Microscopy Sciences. UHPLC grade acetonitrile was purchased from BDH. Xbridge Protein BEH C4 Column (300 Å, 3.5 μm, 4.6 mm×150 mm, 10K-500K) and BioSuite. High Resolution SEC Column (250 Å, 5 μm, 7.8 mm×300 mm, 10K-500K) were purchased from Waters Technologies Corporation. Trifluoroacetic acid was purchased from Neta Scientific.

Conjugation of fluorescent dyes DEAC, TMR, and Cy5. For a 10 mL batch reaction, 0.2 μmol succinimidyl ester derivative of DEAC dye was conjugated with 5 μmol APTES (1:25 ratio) in 100 μL DMSO for the synthesis of C rings that have DEAC dye covalently encapsulated in the silica matrix. For inner or outer surface dye functionalization of a 10 mL reaction batch, 0.4 μmol of maleimido derivative of TMR dye was conjugated with 10 μmol of MPTMS (1:25 ratio), and 0.18 μmol of Cy5 was conjugated with 4.2 μmol MPTMS (1:23 ratio) in 100 μL DMSO. All of the dye conjugations were made one-day prior to their use in the synthesis by mixing the components by pipette and leaving the solution overnight in the glovebox.

Synthesis of PEGylated fluorescent C rings. Fluorescent C rings were synthesized in aqueous solution using surfactant-micelles templating the silica condensation. For a 10 mL batch reaction, 83 mg of CTAB was dissolved in 9 mL deionized water, and 1 mL of ammonium hydroxide solution (0.02 M) was added to the reaction in a 25 mL round-bottom flask. The solution was stirred at 600 r.p.m. at 30° C. for 30 minutes before the addition of 100 μL TMB to expand the micelles, which was followed by stirring for 1 hour. Afterwards, 68 μL TMOS and 100 μL DEAC dye-conjugate was added into the solution in subsequent steps, and the reaction was left stirring overnight at 30° C. The following day, 100 μL PEG-silane (6-9 ethylene glycol units) was added into the 10 mL reaction under stirring at 600 r.p.m., and the solution was left stirring overnight at 30° C. The concentrations of TMOS, CTAB, TMB, and PEG-silane were approximately 45.6 mM, 22.7 mM, 71.9 mM, and 21.5 mM, respectively. The next day after PEG-silane addition, the sample solution was heated at 80° C. overnight without stirring in order to enhance covalent PEG-silane condensation.

Purification of C rings. The day after 80° C. heating, the solution was cooled down to room temperature, syringe-filtered (MWCO 0.2 μm, PTFE), and transferred into a dialysis membrane (MWCO 10K). Then the sample was dialyzed in 200 mL of ethanol/deionized water/glacial acetic acid solution (500:500:7 volume ratio), and the acid solution was changed once a day for three days to remove/etch CTAB from the pores of the C rings, and to remove unreacted reagents from the sample. Following the acid dialysis, the sample was transferred into 5 L deionized water, and the water was refreshed once a day for three days to remove ethanol and acetic acid solvents.

Synthesis of inner surface-PEGylated fluorescent C rings. Following all of the purification and CTAB removal steps to have the C ring pores accessible for inner surface functionalization, 400 μL of PEG-silane (3-ethylene glycol units) was added into 10 mL of the C ring native synthesis solution (estimated concentration 6 μM) in a 25 mL round-bottom flask under stirring at 600 r.p.m. at room temperature. The solution was left stirring overnight. The concentration of PEG-silane (3-ethylene glycol units) was roughly 142 mM.

Synthesis of inner surface-dye-functionalized fluorescent C rings. Following all of the purification steps and CTAB removal steps to have the C ring pores accessible for inner surface functionalization, 100 μL of TMR-silane conjugate in DMSO was added into 10 mL of native C ring synthesis solution in a 25 mL round-bottom flask under stirring at 600 r.p.m., and room temperature overnight. The concentration of TMR dye was roughly 40 μM. For the dye-loading series experiments, TMR concentrations were varied between 10 μM to 120 μM.

Synthesis of outer surface-dye-functionalized fluorescent C rings. Following the same procedure for the first day of the fluorescent C ring synthesis described above, 100 μL of the TMR-silane conjugate DMSO solution described in the previous section was added into 10 mL of native C ring synthesis solution, just before the addition of PEG-silane (6-9 ethylene glycol units) to the outer surface of the rings in a 25 mL round-bottom flask under stirring at 600 r.p.m. at room temperature.

Synthesis of inner/outer surface-dye-functionalized blank C rings. For the synthesis of inner/outer surface-dye-functionalized blank C rings, the addition of conjugated DEAC dye was skipped after the addition of TMOS on the first day of synthesis, so that the blank nanorings were formed without the encapsulation of fluorescent DEAC dyes in the silica matrix. Replacing the TMR dye-conjugate with Cy5 dye-conjugate for functionalization, inner/outer surface-dye-functionalization procedures described above were followed. The concentration of Cy5 dye for both inner and outer-surface-functionalization was 18 μM.

Gel permeation chromatography (GPC). Following the dialysis step, the solutions were concentrated using spin filters (Vivaspin 20 MWCO 30K) in centrifugation (Eppendorf 5810R) at 4300 r.p.m. for 45 min. 400 μL of the up-concentrated sample were injected into GPC column packed with Superdex 200 prep grade resin using 0.9 wt. % sodium chloride saline as buffer solution. Bio-Rad BioLogic LP system was used to operate the GPC column at 2 mL/min flow rate, and Bio-Rad BioFrac was used to collect the GPC fractions of the samples at 14 sec/fraction times absorbing at 275 nm. C rings were separated from the aggregation products and un-reacted reagents via GPC fractionation, and collected samples were run in GPC again to check sample purity via the single-peak particle distribution. These are the GPC control runs reported in the main text to demonstrate sample purity.

High performance liquid chromatography (HPLC). All HPLC runs were carried out on a Waters Alliance 2965 separations module equipped with a column heater, and a Waters 2996 photodiode array detector. The hardware was controlled by a computer running Empower 3 Feature Release 3. Deionized water was generated from a Millipore IQ7000 water system (18.2 MS/resistivity) and acetonitrile was obtained from BDH (UHPLC grade). The columns used were 150 mm Waters Xbridge BEH C4 Protein separation columns with 300 Å pore size and 3.5 μm particle size and 50 mm Waters Xbridge BEH C18 Protein separation columns with a 300 Å pore size and 3.5 μm particle size. All injections were 10 μL of 15 μM nanorings. Concentrations for injected samples were determined by FCS.

Transmission electron microscopy (TEM). TEM samples were prepared by dropping ~8 μL of the sample solution diluted in ethanol onto a carbon film coated copper TEM grid, and letting the sample air-dry on the grid on a filter paper. Dry-state TEM images were taken using FEI Tecnai T12 Spirit microscope operated at 120 kV. Cryogenic electron microscopy (cryo-EM) was performed on a ring sample.

Fluorescence correlation spectroscopy (FCS) of fluorescent C rings. Fluorescence correlation spectroscopy (FCS) measurements were performed on C rings encapsulating DEAC dye, using a home-built FCS setup with HeNe 445 nm excitation source. FCS samples were prepared by diluting samples in water on a glass-bottom microwell dish. Photons were collected by an avalanche photodiode detector (SPCM 14, Perkin-Elmer. The photocurrent from the detector was digitally auto-correlated with a correlator card (Correlator.com). Before each set of measurements, the observation volume was calibrated with 6CR110 as standard dye such that the ratio of the radial to the axial radii of the focal volume is between 0.1 and 0.2. FCS auto-correlation curves were analyzed to obtain the hydrodynamic size, brightness per particle, and the concentration of the samples as described in previous publications.

Steady state absorption spectroscopy. Varian Cary 5000 spectrophotometer was used to measure the absorption spectra of the samples in parallel to FCS measurements to calculate the number of dyes per particle as described in equation 3 in the Supporting Information. To acquire the absorption spectra, first a baseline subtraction against 3 mL of fresh deionized water in a quartz cuvette was performed. After the blank was measured the sample was added directly to the cuvette and an absorption spectrum was acquired. The absorbance maxima of each sample were kept within the linear region of the Beer-Lambert Law for concentration determinations and further calculations as detailed in the Supporting Information.

Figure 2:
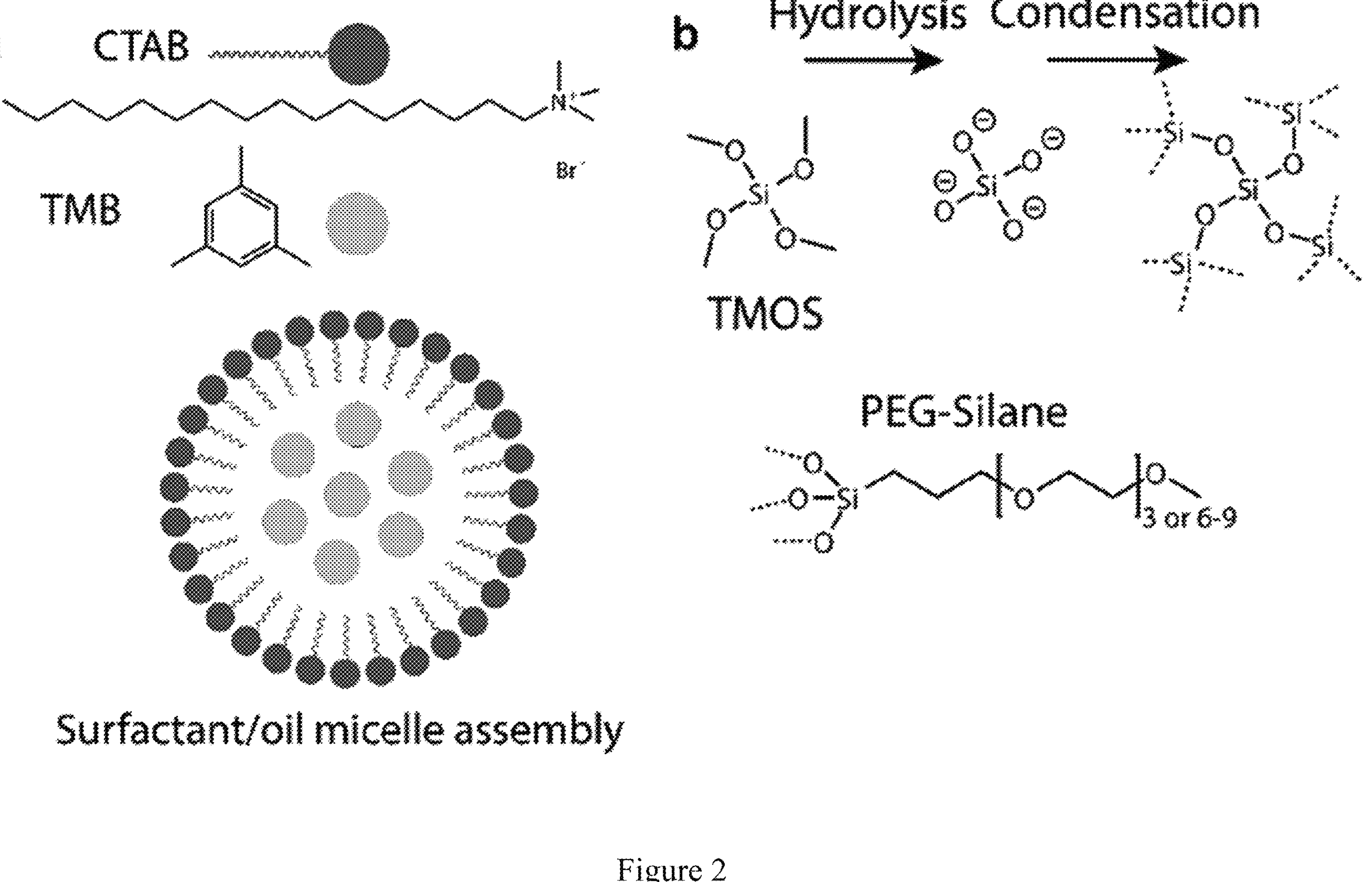
FIG. 2 shows molecular structure of compounds and silica networks as well as dye-silane conjugation chemistry. (a) Chemical structures of surfactant (CTAB) and oil-pore expander (trimethyl benzene, TMB). (b) Hydrolysis and condensation steps of silica precursor (TMOS), and chemical structure of polyethylene glycol (PEG)-silane molecule. (c) Molecular illustration of DEAC dye encapsulating silica matrix. (d,e,f) Conjugation of succinimidyl ester derivative of DEAC dye with aminopropyl-silane (d), as well as maleimido derivatives of TMR (e) and Cy5 dye (f) with mercaptopropyl-silane.
Figure 2:
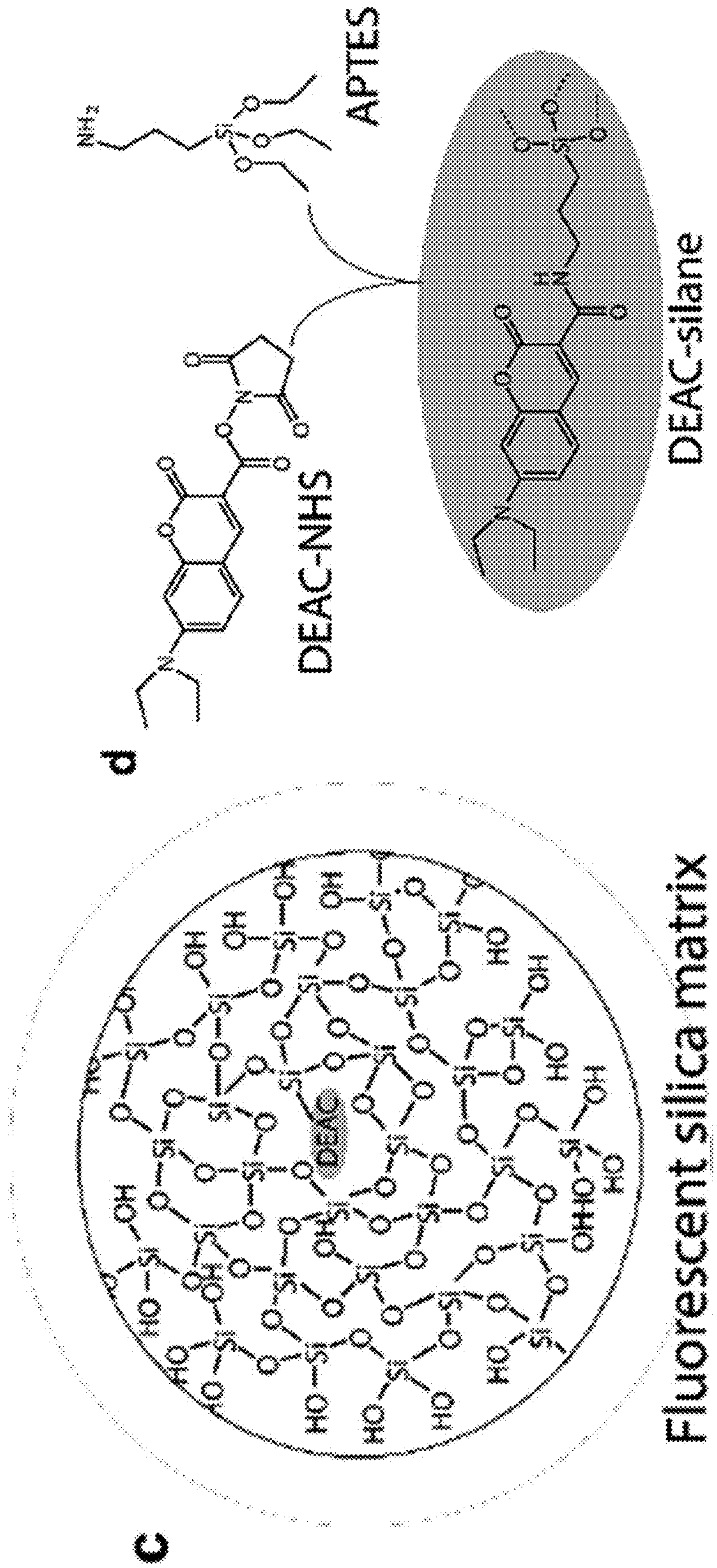
Figure 2:
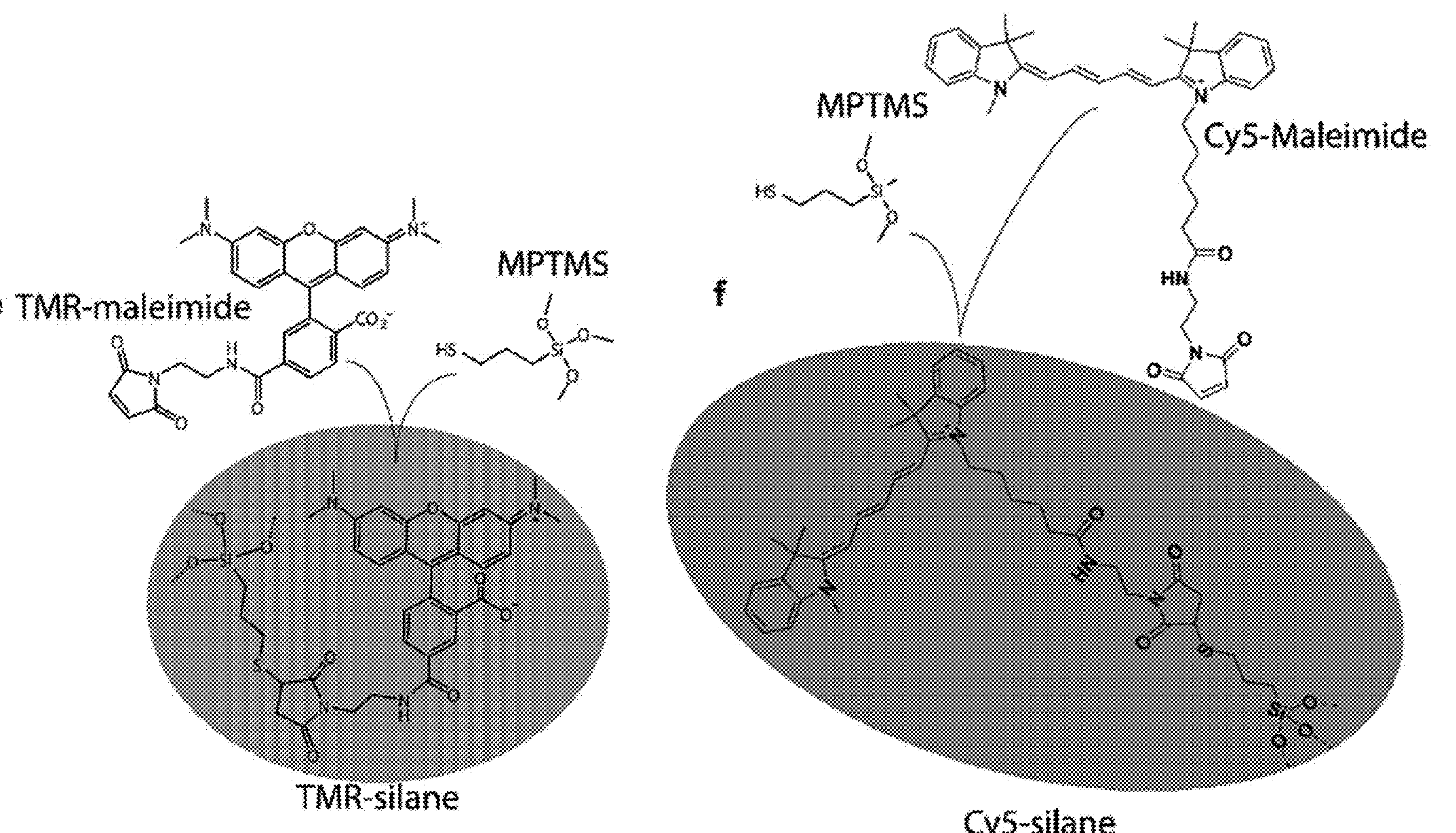

Results and Discussion. Orthogonal pathways to inner and outer C ring surface functionalization. FIG. 1 shows representative cryo- and transmission electron microscopy (cryo-EM/TEM) images of planar and edge-on views of a silica nanoring formed around a TMB swollen hexadecyltrimethyl ammonium bromide (CTAB) micelle, originally used to unambiguously establish the ring geometry. For convenience, these nanomaterials will be referred to as Cornell rings or simply C rings. Because the inner surface of C rings in the surfactant mediated synthesis is originally shielded/covered by the surfactant micelle as illustrated in FIG. 1, this micelle-directed formation mechanism should enable orthogonal functionalization of inner and outer C ring surfaces. This effect is enhanced by partial wrapping of the trimethylbenzene (TMB) swollen micelle around the ring, driven by electrostatic attraction between the positively charged micelle surface (from quaternary ammonia surfactant head groups) and the negatively charged silica surface (from deprotonated Si—OH groups). After C ring synthesis as described above, the inner surface is still covered by the micelle, while the outer bare silica surface is available for coating with a poly(ethylene glycol) layer (PEGylation step) and/or functionalization with other moieties as described in detail in earlier studies on conventional spherically shaped fluorescent core-shell SNPs with sizes below 10 nm referred to as Cornell dots or simply C dots. Once the outer silica surface is covered with these moieties, removal/etching of the surfactant micelles via e.g., dialysis in acidic solutions (see above) exposes bare inner silica surface, which can subsequently be functionalized in an orthogonal fashion with other moieties of interest. Possible steps of such orthogonal functionalization schemes are schematically depicted in FIG. 1, while the molecular structures of all chemical compounds used in the reactions described in this study are shown in FIG. 2. In order to render the original C rings fluorescent for simple optical detection, the succinimidyl ester of 7-diethylamino-coumarin-3-carboxylic acid (DEAC-dye) was used, which has an absorption maximum around 440 nm, i.e. in the blue. This dye molecule can conveniently be reacted with an aminopropyl-triethoxysilane (APTES) to provide a dye-silane conjugate (FIG. 2*d*), which as a result of its neutral charge state and small size (MW~350 g/mole) in turn should get covalently encapsulated reasonably well into the matrix of the silica rings.

Figure 3:
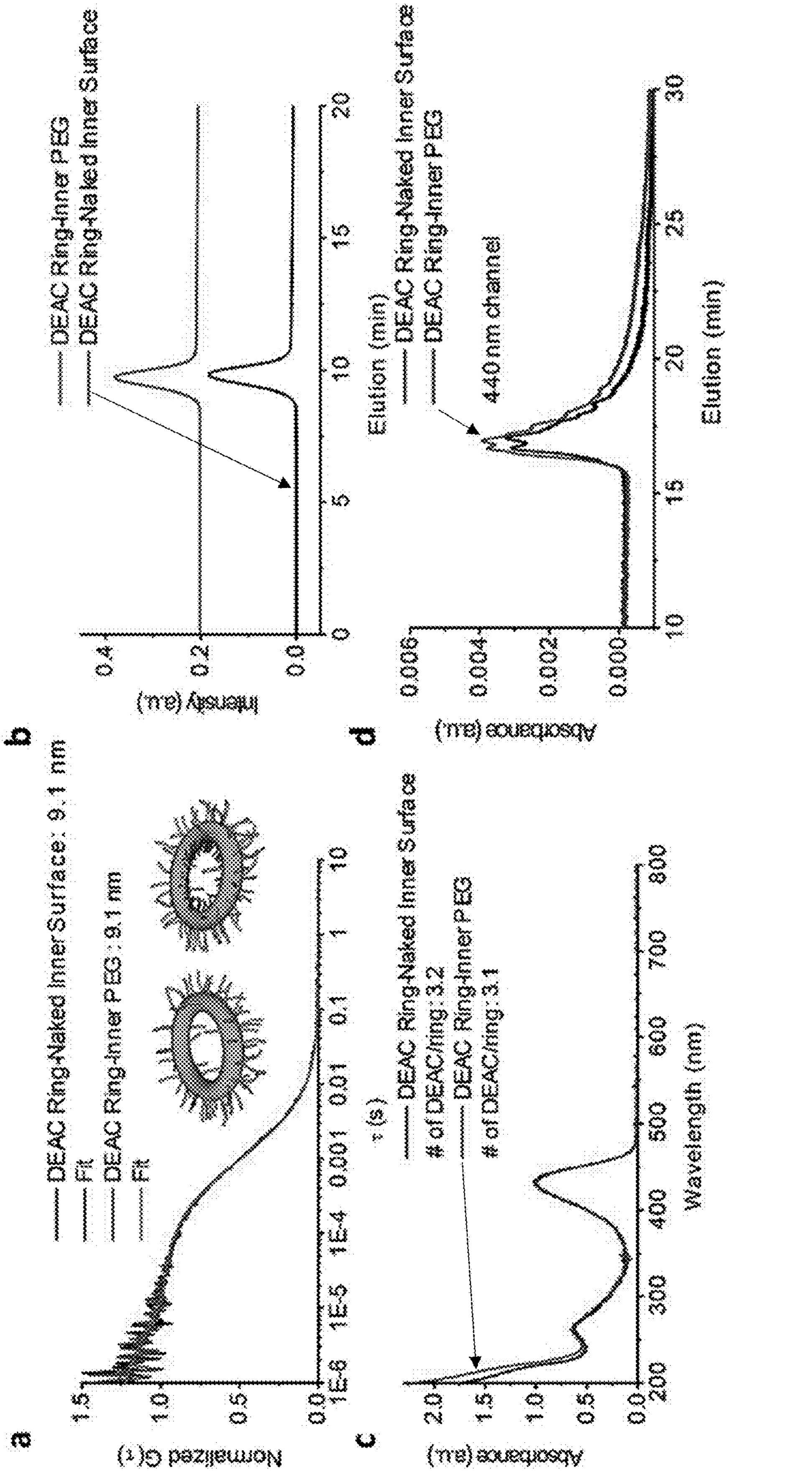
FIG. 3 shows a comparison between fluorescent silica nanorings (DEAC-rings) with and without inner surface PEGylation (with 3 EO containing PEGs). (a) FCS auto-correlation curves suggesting 9.1 nm hydrodynamic sizes for both samples. (b) Analytical scale GPC chromatograms of both samples. (c) Absorption spectra for the naked inner surface and PEGylated inner surface DEAC-rings, suggesting (together with FCS results) 3.2 and 3.1 DEAC dyes per silica nanoring, respectively. (d) HPLC chromatograms at 440 nm read out channel (DEAC dye absorption). (e,f) TEM images of DEAC-rings with naked (e), and PEGylated (f) inner surfaces.
Figure 3:
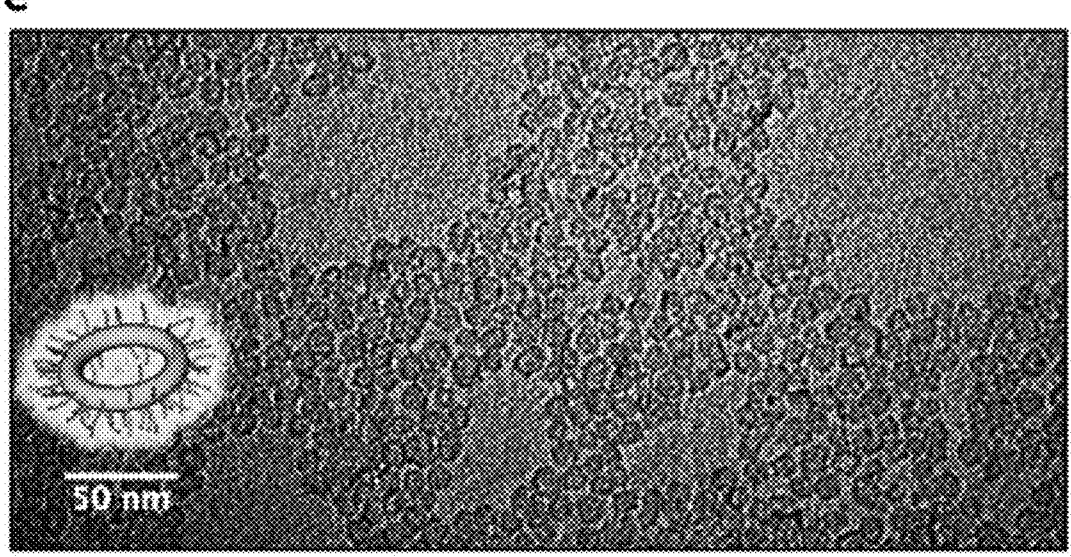
Figure 3:
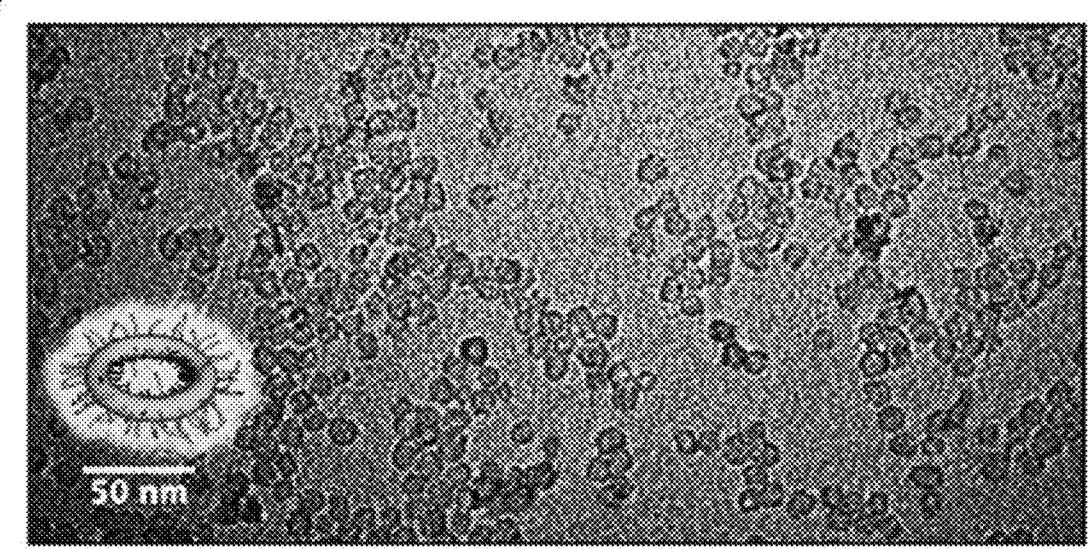

In a first set of experiments to examine orthogonal functionalization pathways of the inner surface of the silica nanorings, two samples were prepared with outer surfaces of both samples functionalized with a 6-9 EO subunit PEG-silane. One sample had a naked inner surface while the other sample had an inner surface functionalized using a 3 EO-chain length PEG-silane as shown in FIG. 2*b*. The same ring synthesis batch was used for the preparation of these two samples in order to minimize the effects of batch to batch synthesis variations. To that end, a mother batch was synthesized by taking the as-prepared C rings and PEGylating their outer silica surface. An aliquot of this batch was simply submitted to surfactant micelle removal/etching providing C rings with a bare inner surface, while a second aliquot underwent inner surface PEGylation after micelle etching. After final purification steps (see Methods section), in order to establish a baseline study, these two C ring samples underwent in-depth characterization via a combination of techniques (FIG. 3) including fluorescence correlation spectroscopy (FCS), analytical gel permeation chromatography (GPC), absorption spectroscopy, high performance liquid chromatography (HPLC), and transmission electron microscopy (TEM). FCS results (FIG. 3*a*) suggested identical hydrodynamic sizes of 9.1 nm for both samples, corroborated by single-peak distributions and equal elution times in GPC (FIG. 3*b*). Successful inner surface PEGylation of the C rings was evidenced by a slightly higher absorption band in the UV region the two ring samples normalized to the 440 nm DEAC dye absorption maximum (FIG. 3*c*), behavior characteristic for the presence of PEG. Results of HPLC runs showed that both C rings elute at the same time and with similar peak shapes (FIG. 3*d*), suggesting that in this particular case of simple PEG coating of the inner surface versus bare silica, HPLC is not very sensitive to the details of the inner surface chemical properties. The shape and fine structure of the HPLC chromatograms with multiple peaks on a curve that first rises sharply and then tapers off at longer times are very similar to those observed for conventional PEGylated fluorescent C' dots suggesting incomplete encapsulation of one or more DEAC dyes leading to hydrophobic patches that prolong the corresponding elution times relative to a fully PEGylated surface. HPLC as a qualitative tool to compare different functionalized C rings. Finally, as expected TEM images of the two C ring batches showed no discernible differences in particle morphology (compare FIGS. 3*e* and 3*f*).

Figure 4:
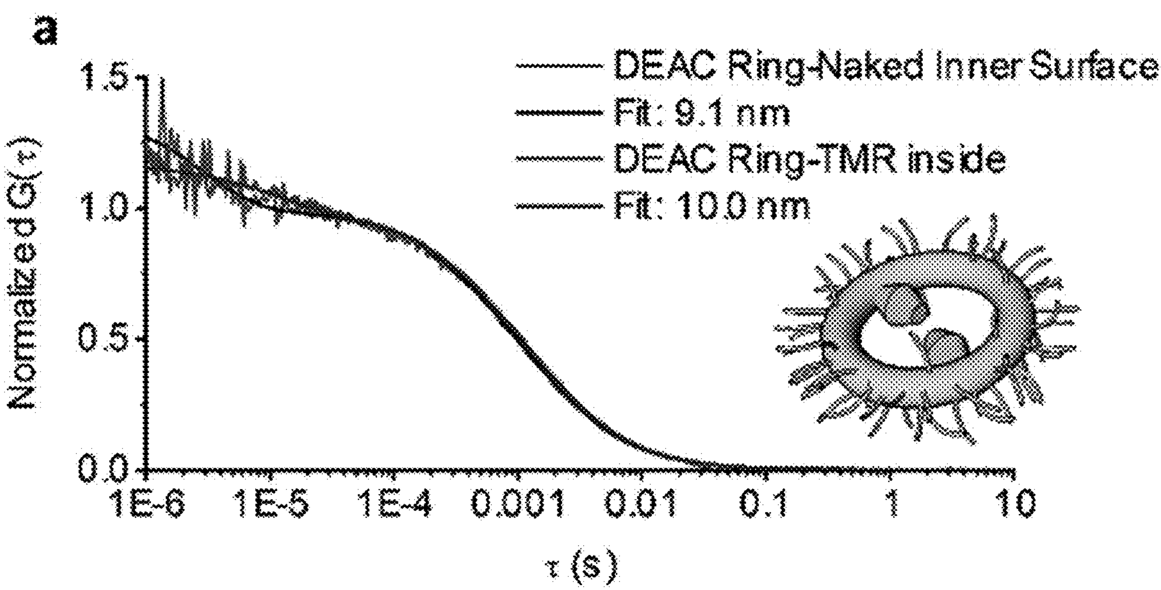
FIG. 4 shows a comparison between DEAC-rings with TMR functionalization inside and outside. (a,c) FCS auto-correlation curves suggesting hydrodynamic sizes of inside (a) and outside (c) TMR functionalized DEAC-rings of 10.0 nm and 11.1 nm, respectively, both larger than the reference DEAC-rings with no extra functionality (9.1 nm, black). (b) GPC chromatograms of these two TMR functionalized ring samples. (d) Absorption spectra of inside and outside TMR-functionalized DEAC-rings compared to reference DEAC-rings and normalized to DEAC absorption maximum at ~440 nm. Combination of absorption and FCS results confirm the same DEAC dye numbers for these two ring samples (3.8 and 3.7 dyes for inner and outer functionalized rings, respectively), but suggest different degrees of TMR functionalization with 1.8 and 4.5 TMR dyes for the inner and outer surface functionalized rings, respectively. (e,f) HPLC chromatograms of inside and outside TMR functionalized DEAC-rings at 550 nm read out channel (e, TMR dye absorption), and at 440 nm read out channel (f, DEAC dye absorption). In (f) results are plotted against the reference DEAC-rings with no TMR functionality.
Figure 4:
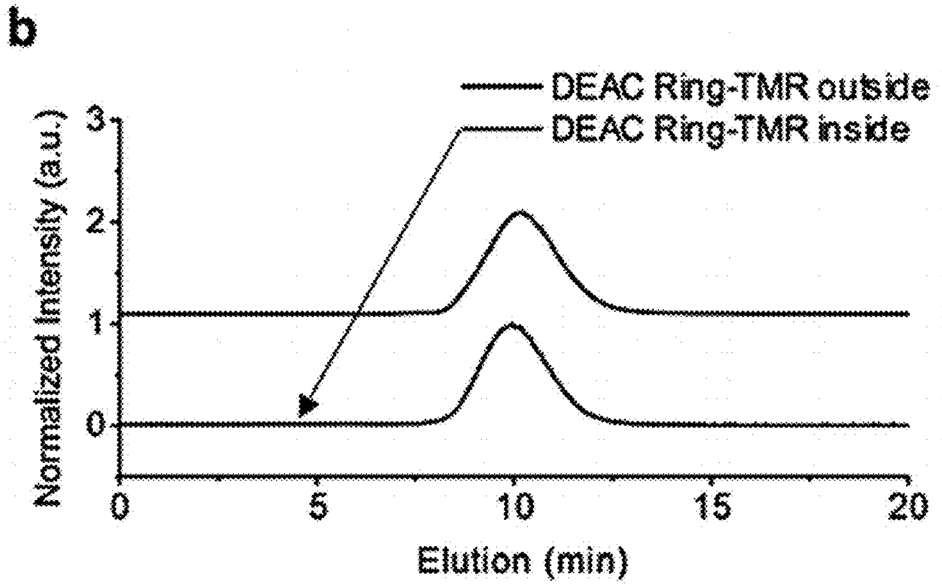
Figure 4:
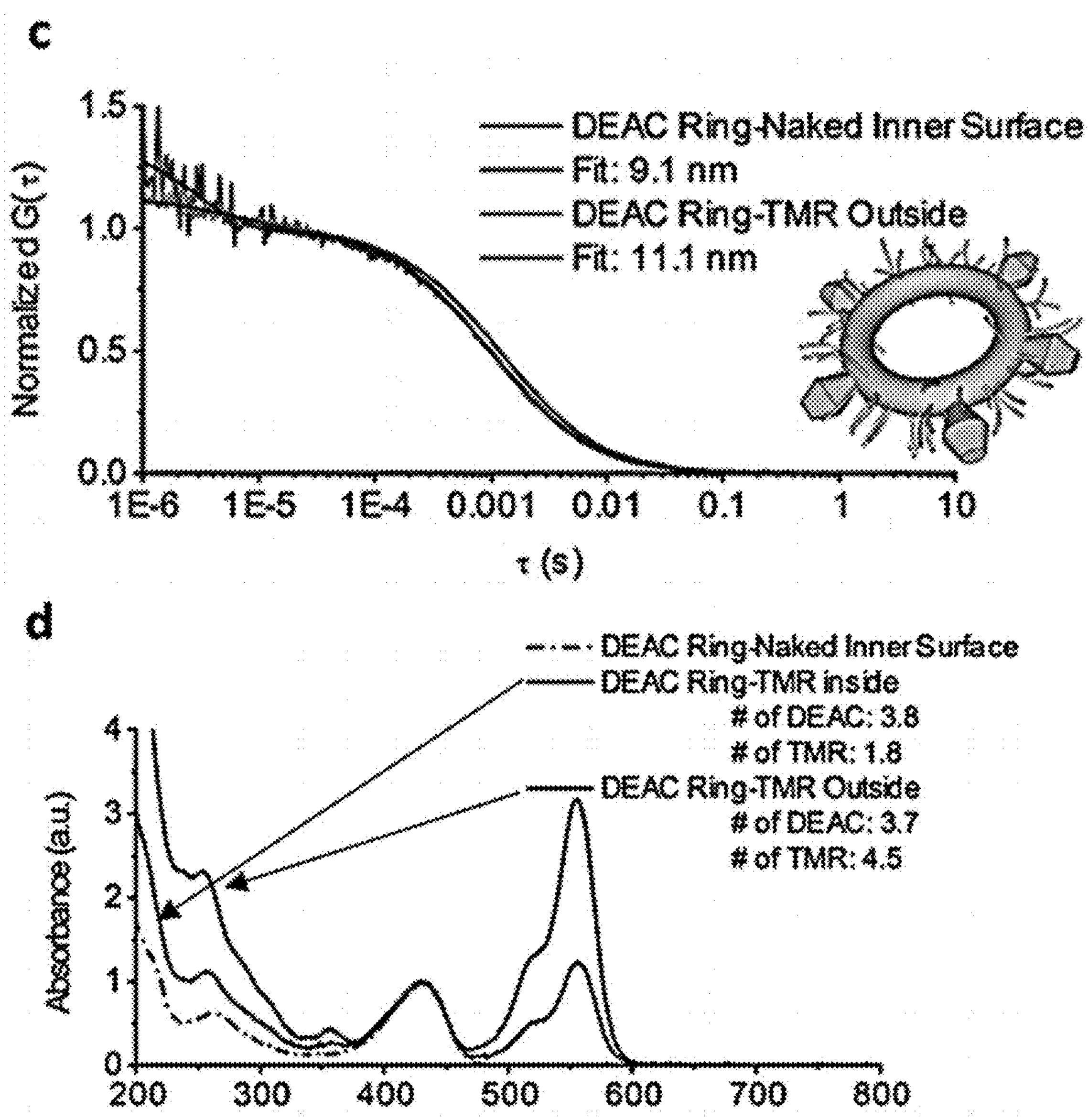
Figure 4:
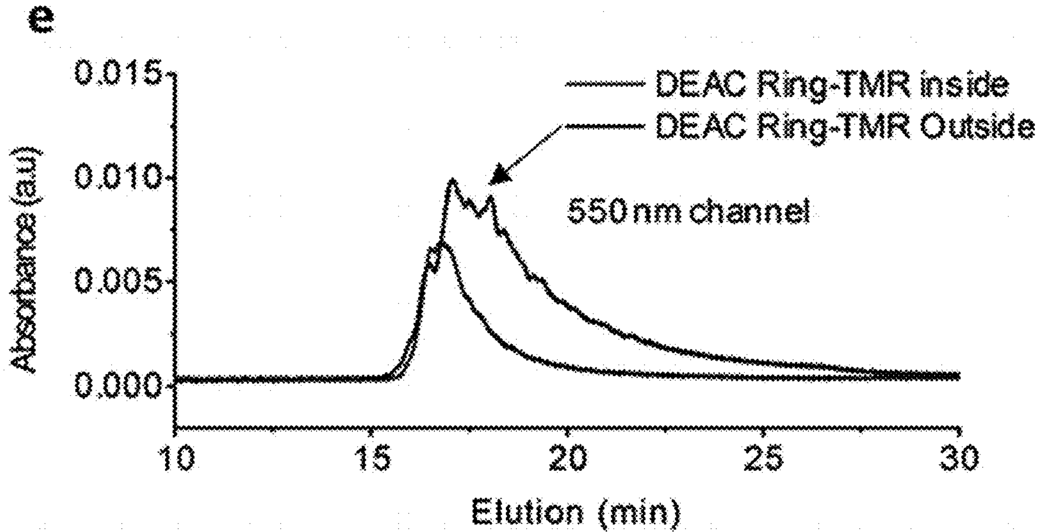
Figure 4:
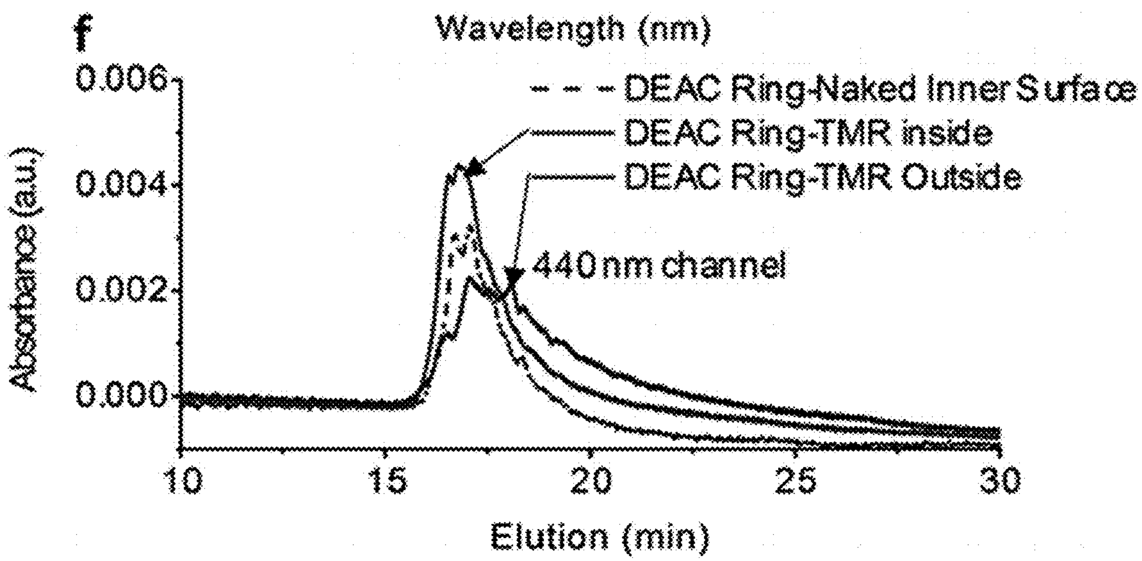

Inner and outer C ring surface functionalization with TMR dye as revealed by HPLC. Next, either the inner or the outer surface of aliquots of the mother batch with zwitterionic (i.e. zero net charge) tetramethyl-rhodamine (TMR) dye, which has an absorption maximum around 550 nm, well separated from that of the DEAC dye around 440 nm encapsulated into the silica ring matrix (vide supra). To that end, TMR-silane was first generated from reaction of the maleimido derivative of TMR with mercaptopropyl-trimethoxysilane (MPTMS, FIG. 2*e*). This dye derivative was then added to an aliquot of the mother batch either shortly before addition of the PEG layer on the outer surface in the presence of the CTAB micelles covering the inner surface or after this PEGylation step and micelle removal thereby functionalizing the inner ring surface with TMR dye (see Method section). In both cases, TMR-silane was added at the same concentration (40 Comparison of characterization results of these two C ring batches is shown in FIG. 4. FIGS. 4*a* and *c* shows FCS correlation curves of inner and outer surface functionalized batches, respectively (i.e. carrying TMR dye either on the inner or outer surface while both encapsulating DEAC dye in the silica ring matrix), plotted against those of unfunctionalized C rings (DEAC dye carrying rings only, see FIG. 3*a*). FCS data analysis suggested that the hydrodynamic particle size for the inner surface functionalized C rings increased from 9.1 nm to 10.0 nm, while that for the outer surface functionalized rings increased from 9.1 nm to 11.1 nm when compared to the reference nanoring without TMR. Both functionalized samples showed a single-peak distribution in GPC (FIG. 4*b*). The outside functionalized C rings were slightly more size dispersed, which correlates with the slightly larger size increase observed in FCS. When comparing absorption spectra of the two TMR-functionalized ring batches normalized to the 440 nm absorption of the DEAC dye (FIG. 4*d*), even though TMR-silane was added at the same concentration for both samples it is apparent from the higher TMR absorption observed around 550 nm that there are substantially more TMR dyes on the outer than on the inner surface. Combining information from FCS on particle concentration with these absorption results (see Methods), the number of TMR dyes per C ring was determined to be 4.5 and 1.8 for outer and inner surface functionalization, respectively, correlating well with the larger size for the former as detected by FCS. This higher dye number could be explained by the larger surface area available on the outside of the C rings, which translates into the availability of more surface silanol groups for TMR dye-silane attachment, as well as the higher accessibility of the outer versus the inner ring surface which suggests steric hindrance of TMR functionalization of the inner surface once the first TMR dye is in place.

In addition to larger hydrodynamic C ring size from higher TMR dye numbers on the outer ring surface relative to the inner surface, HPLC chromatograms collected with read out at 550 nm, the TMR dye absorption maximum, also showed substantial differences between these two batches (FIG. 4*e*). Compared to the inner surface-functionalized C rings, the outer surface-functionalized rings had a wider distribution and tailing that indicates substantially increased nanoring hydrophobicity. Furthermore, using the 440 nm read out channel matching the DEAC dye absorption, HPLC results (FIG. 4*f*) highlight that the inner surface-functionalized nanorings eluted at more similar times and exhibited a more similar elution profile to C rings with no inside or outside surface functionality as compared to the outside functionalized rings. These results establish that in contrast to outer surface conjugations, functionalizing the inner ring surface with hydrophobic moieties, here TMR dyes, effectively "hides" these molecules in the pore of these ultrasmall nanorings, thereby shielding them from interactions with their environment. Taken together, the preceding results unambiguously demonstrate selectively functionalization of the inner versus the outer surface of ultrasmall silica nanorings, and that HPLC is a powerful experimental tool to differentiate between these two functionalization sites. In addition to the relatively rapid (short elution times) screening HPLC method (referred to as Method 2) employed here, a previously developed HPLC method was applied (referred to as Method 1 with longer elution times) to both ring samples described in FIGS. 3 and 4. These studies summarized in FIG. 7 demonstrate that for DEAC- and TMR-functionalized rings HPLC results were robust against changes in both the HPLC parameters and columns. This suggests that a variety of HPLC separation methods may be successful in differentiating between these types of chemical differences and that it may be possible to extend these chromatographic methods to other ultrasmall nanomaterial compositions and morphologies.

Figure 5:
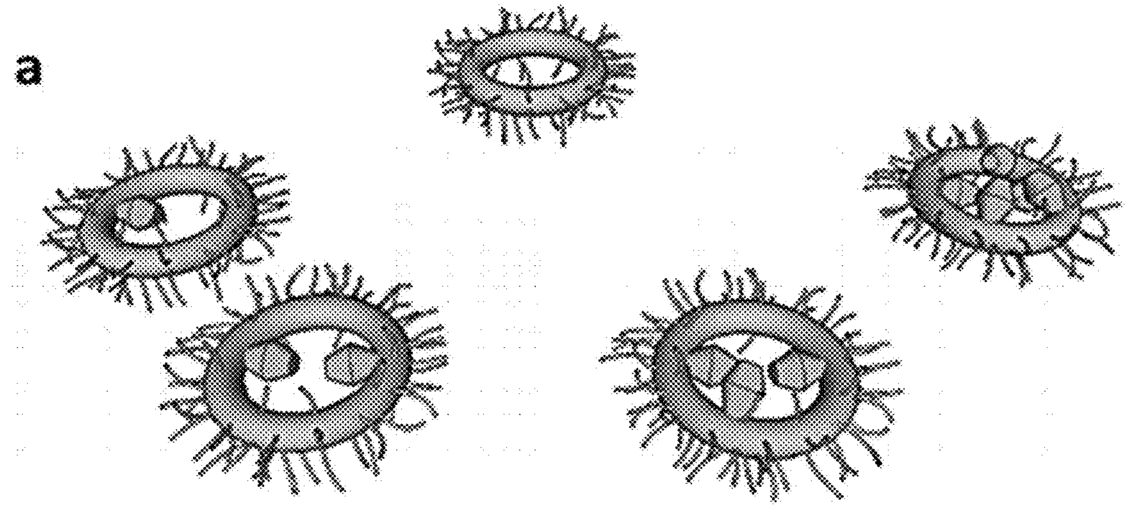
FIG. 5 shows a comparison of DEAC rings with increasing inner surface functionalization with TMR dye. (a) Illustration of TMR loading to the inside surfaces of DEAC-rings, where as a function of TMR concentration in the synthesis, TMR dyes progressively get exposed to the ring outside as the number of TMR dyes per DEAC-ring increases. (b) FCS auto-correlation curves of ring samples obtained from TMR-dye concentrations in the synthesis of 10 μM, 30 μM, 80 μM, and 120 μM resulting in hydrodynamic sizes of 9.6 nm, 10.4 nm, 10.7 nm, and 11.0 nm, respectively. (c) Absorption spectra of the same four samples as in (b) normalized to the 440 nm DEAC dye absorption. Together with FCS results from (b) these data suggest 3.7, 4.2, 3.8, and 4.4 DEAC dyes encapsulated in the silica ring matrix, and 1.0, 2.2, 3.5, and 6.5 TMR dyes on the (inner) silica ring surface for each of the four batches, respectively. (d) GPC chromatograms of these four TMR functionalized ring samples. (e, f) HPLC chromatograms of the same four TMR functionalized DEAC-ring batches as in (b, c, d) measured at the 440 nm read out channel (e, DEAC dye absorption) and the 550 nm read out channel (f, TMR dye absorption). In (e) HPLC data of the four ring batches are compared to results of the parent (non-TMR functionalized, naked) rings.
Figure 5:
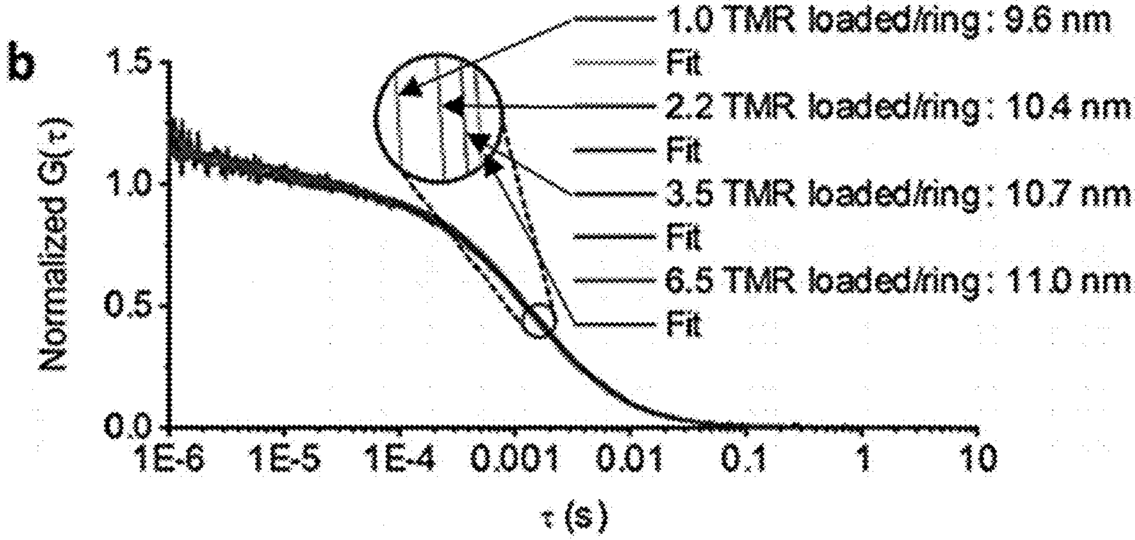
Figure 5:
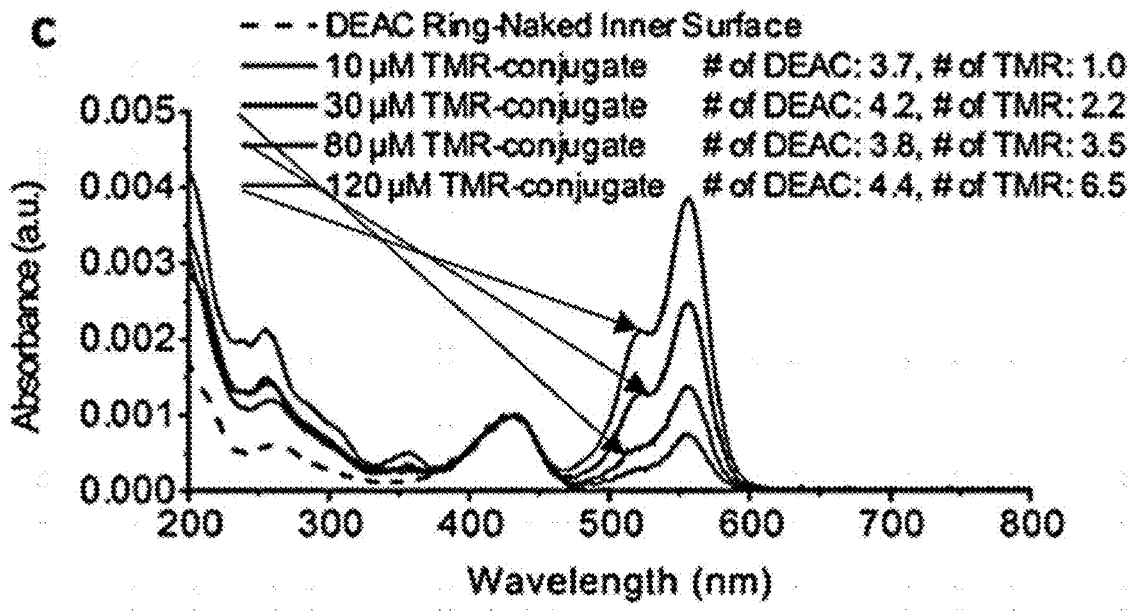
Figure 5:
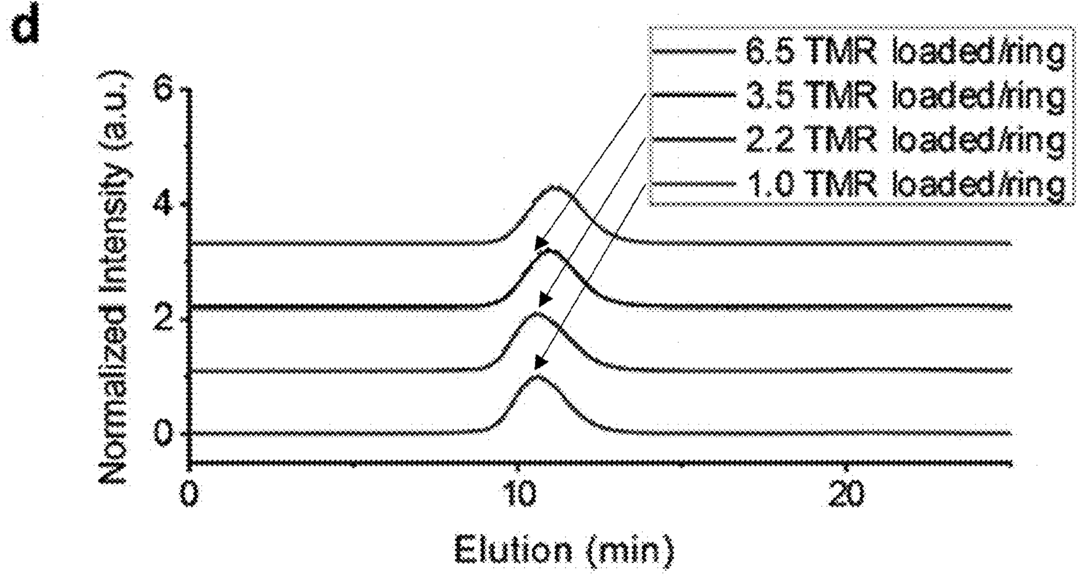
Figure 5:
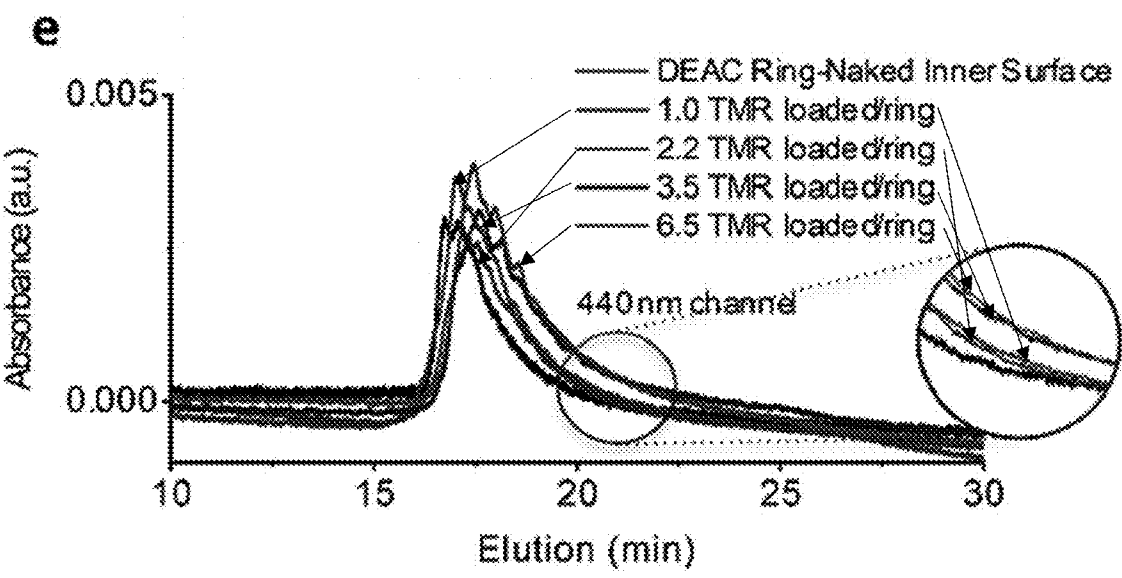
Figure 5:
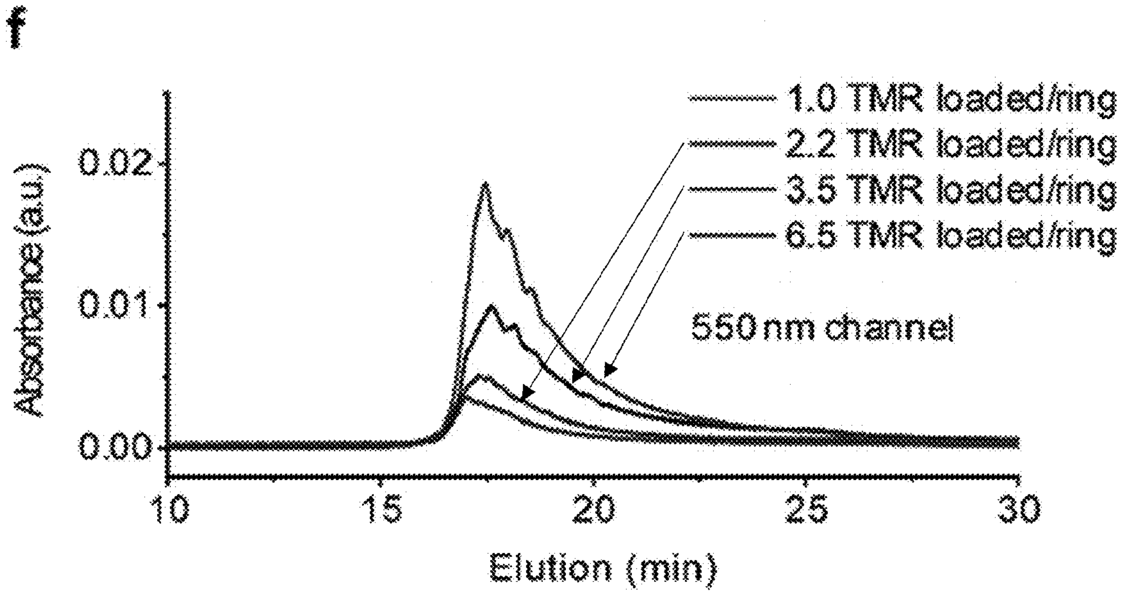
Figure 6:
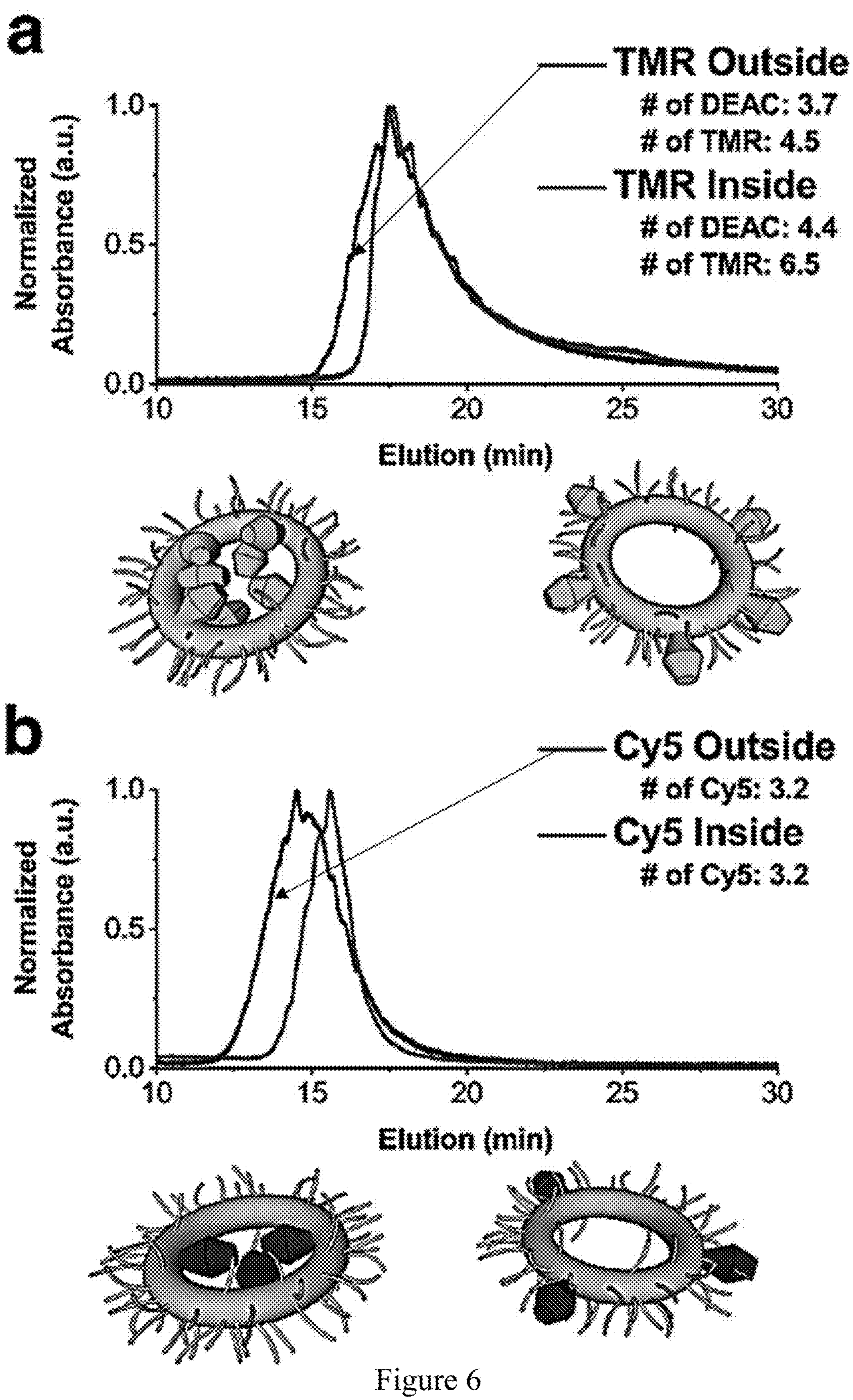
FIG. 6 shows HPLC chromatograms at (a) 550 nm (TMR dye absorption), and (b) 647 nm (Cy5 dye absorption) read out channels for inside/outside TMR dye loaded DEAC rings, and inside/outside Cy5 dye loaded blank silica rings, respectively.
Figure 8:
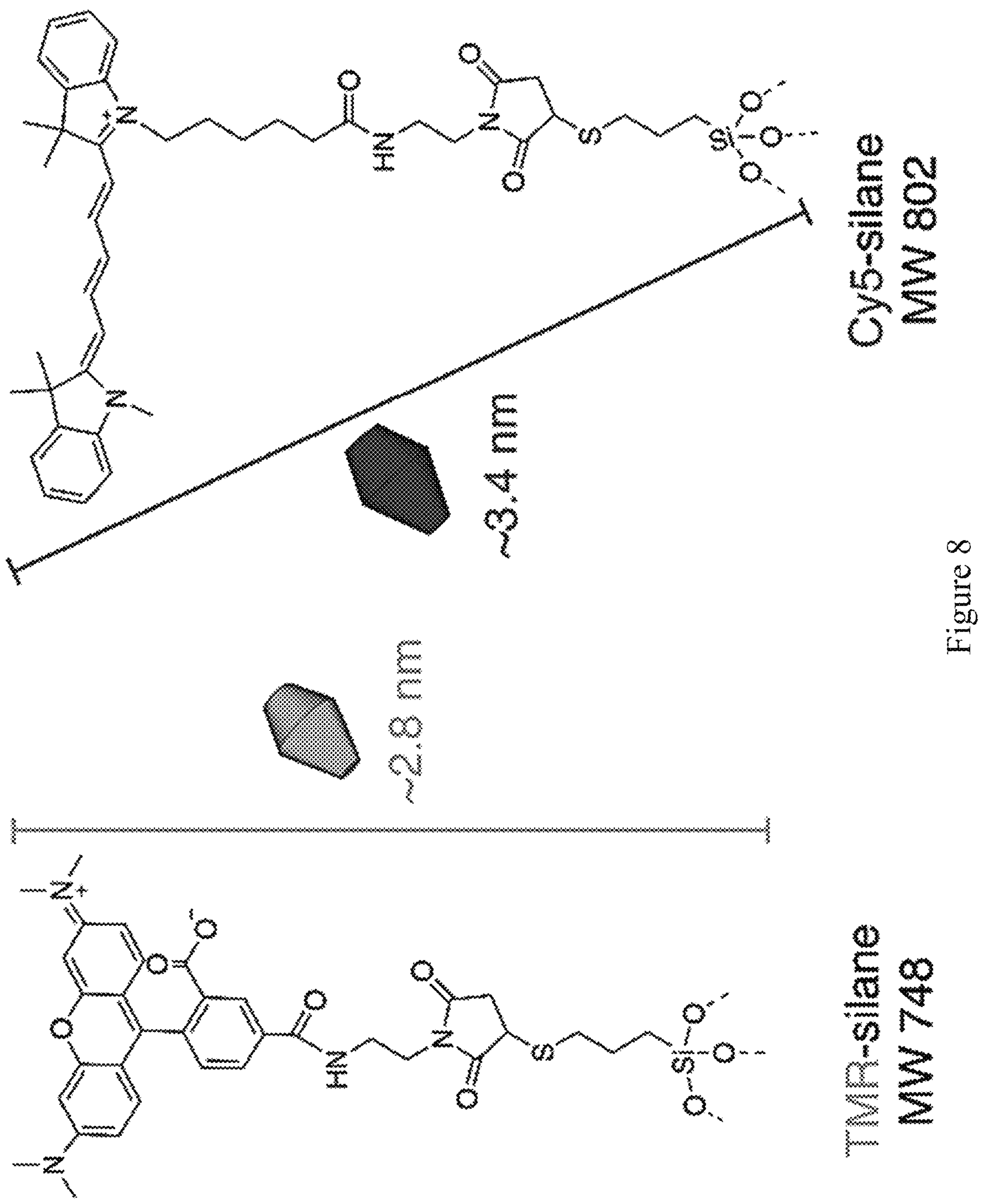
FIG. 8 shows molecular structures and dimensions of "stretched" TMR-silane (left) and Cy5-silane (right) dye conjugates.

Assessing "effective" inner ring surface loading capacity by HPLC. The ability to distinguish between inner and outer surface functionalization via HPLC allowed determination of an "effective" cargo loading capacity of the inner surface of C rings, i.e., the loading capacity for which a particular hydrophobic cargo can effectively be "hidden" in the pore. The loading capacity is a crucial parameter, e.g., in the context of the delivery of drugs and other pharmaceutically relevant molecules to sites of disease. Once the effective loading capacity of the inside surface of the nanorings is reached, further functionalization may still occur, but only on the outer surface of the nanorings exposing the cargo to interactions with the environment. In order to assess this quantity, the inner surface of C rings encapsulating DEAC dye in their silica matrix were functionalized employing increasing concentrations of TMR-silane (10 μM, 30 μM, 80 μM, and 120 μM) using the same approaches as described before (see Methods). With a silica wall thickness of only around 2 nm, nanoring pore size of around 6 nm, and TMR-silane conjugate size of somewhere between 2-3 nm (FIG. 8), i.e., roughly equal to pore radius, as illustrated in FIG. 5*a* it expected to see TMR dye being pushed towards the outside of the nanorings as the number of TMR dyes per nanoring increases beyond two (FIG. 5*a*). This is consistent with what was experimentally observed via HPLC. Analysis of FCS measurements (FIG. 5*b*) combined with that of absorption spectra (FIG. 5*c*) normalized to the 440 nm DEAC dye peak of the four C ring samples obtained from increasing TMR-silane precursor in the synthesis suggested increasing hydrodynamic sizes of 9.6 nm, 10.4 nm, 10.7 nm and 11.0 nm as well as 1.0, 2.2, 3.5 and 6.5 TMR dyes per nanoring, respectively. The associated GPC distributions got progressively more disperse as the number of TMR-silane per nanoring increased (FIG. 5*d*). In the corresponding HPLC chromatograms taken at 440 nm (DEAC dye) and 550 nm (TMR dye) read out, see FIGS. 5*e* and *f*, respectively, relative to the unfunctionalized rings (black curve in FIG. 5*e*), increasing shifts and tailing were seen towards longer elution times/more hydrophobic behavior, in particular for C rings with more than 2 dyes per particle. As schematically illustrated in FIG. 5*a*, this suggests a shift from well-hidden TMR dyes in the pore to more and more TMR dyes exposed to the outside leading to increasingly hydrophobic nanoring behavior. Once the ring pore is significantly overloaded, the cargo is exposed to the outside so much that these inner-functionalized rings become more hydrophobic than outside-functionalized rings. This is demonstrated in FIG. 6*a* where HPLC traces from a ring with 6-7 TMR molecules on the inside begin eluting at later retention times as compared to a ring with 4-5 TMR molecules on the outside (see schematic) suggesting more hydrophobic character for the inner functionalized ring. This result demonstrates the critical importance of elucidating the "effective" loading capacity of the ring pore, as overloading the ring pore renders the vehicle more hydrophobic than functionalization of the outside surface. It is important to note, that the rings overloaded on the inside are likely more hydrophobic than the outside functionalized rings because hydrophobic ligands on the outside may benefit from partial shielding by the hydrophilic PEG layer. The inside surface was left un-PEGylated so that hydrophilic versus hydrophobic behavior depended primarily on localization and "hiding" of the hydrophobic cargo within the pore, which it was desired to elucidate.

Figure 9:
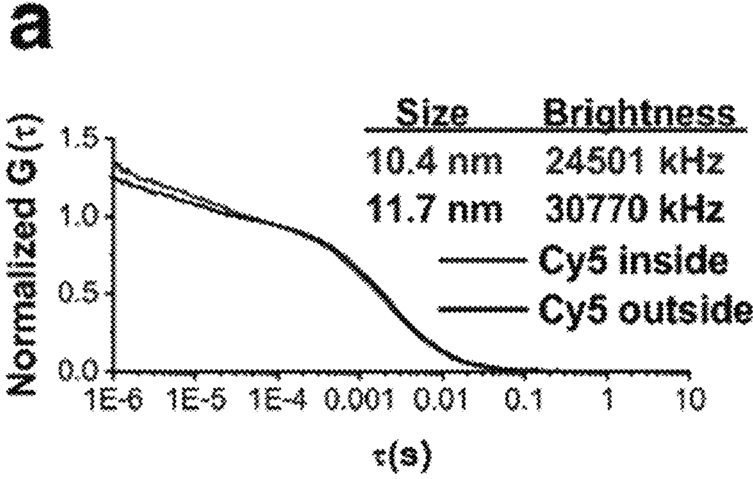
FIG. 9 shows characterization of plain rings (i.e. no DEAC in the silica ring matrix) with inner and outer surfaces functionalized with Cy5 dye. (a) FCS auto-correlation curves of inside and outside Cy5 functionalized silica nanorings suggesting 10.4 nm and 11.7 nm hydrodynamic sizes, and brightness as photon counts of 24501 kHz and 30770 kHz, respectively. (b) GPC chromatograms at 647 nm read out channel (Cy5 dye absorption) of batches in (a). (c) Absorption spectra of the same batches as in (a) normalized to the maximum Cy5 absorption. Combined with FCS results these features translate to the same Cy5 dye number per ring of 3.2 for both samples. The increase in absorption of the shoulder on the left of the main Cy5 absorption peak observed for the inside functionalized rings (red) suggests increased non-radiative energy transfer between dyes in close proximity, consistent with decreased brightness as measured by photon counts in FCS shown in (a). (d,e) TEM images of inside (d) and outside (e) Cy5 functionalized silica nanorings. Insets show illustrations of the Cy5 dye functionalized and PEGylated silica nanorings (no DEAC dye is covalently incorporated into the silica matrix of the rings).
Figure 9:
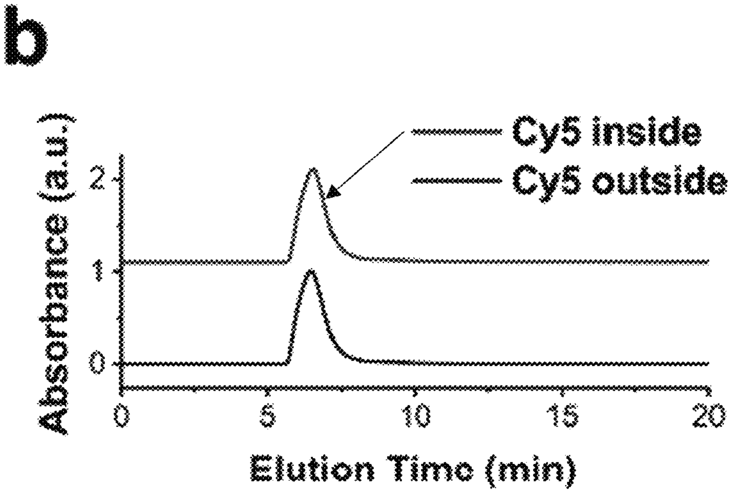
Figure 9:
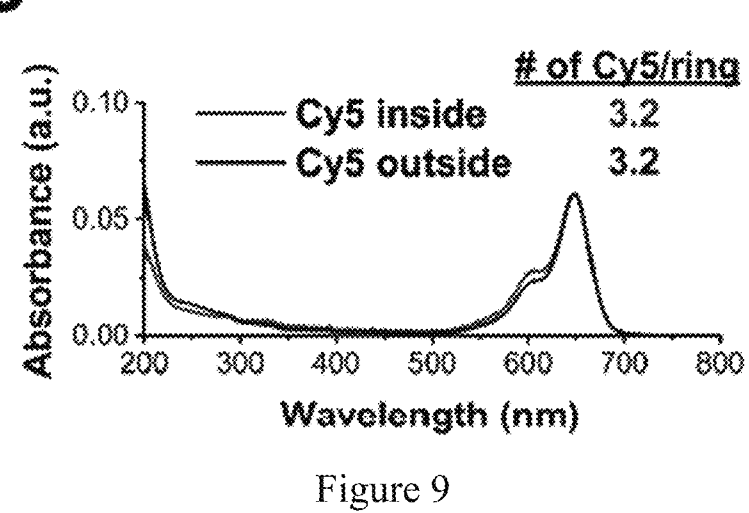
Figure 9:
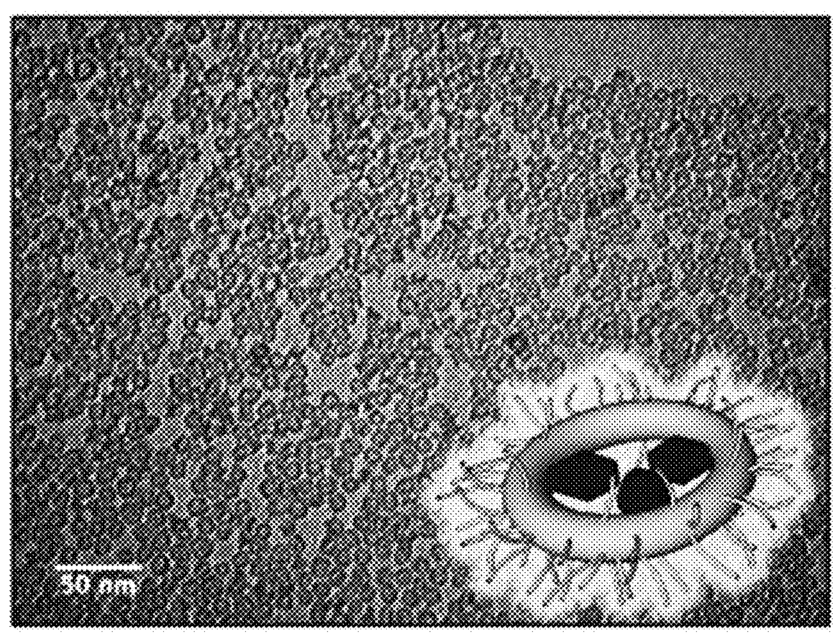
Figure 9:
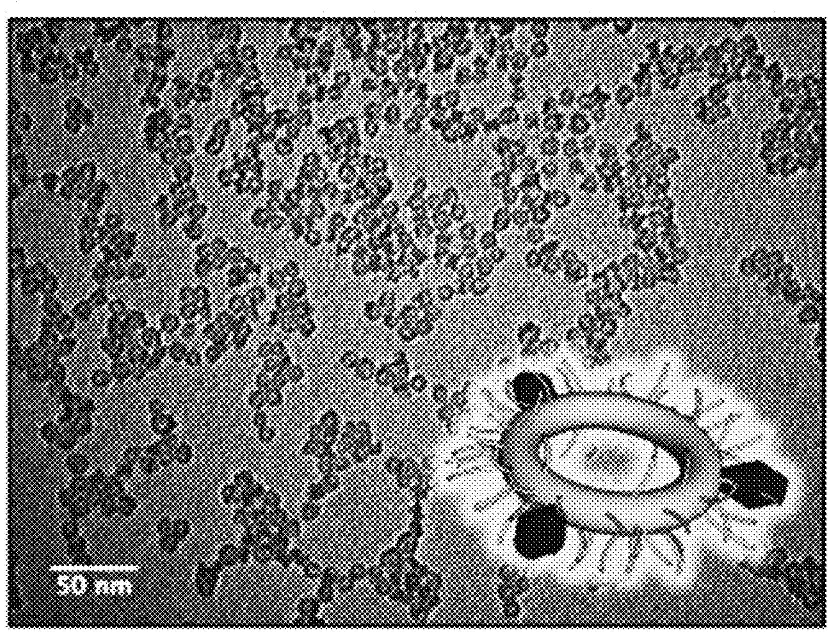

HPLC-derived effective inner ring loading capacity as a function of cargo size and charge. One would expect that the effective inner ring loading capacity is sensitive to the size of the hydrophobic cargo relative to the pore size. In other words, the larger the hydrophobic cargo the more difficult it is to hide it on the inside of the single pore of the ring. In order to test this hypothesis, inner and outer surfaces of blank C rings (i.e., no DEAC dye in the silica ring matrix) were functionalized with a Cy5 derivative of net positive charge (see Methods and FIG. 2*f*), a fluorescent dye belonging to the cyanine dye family that is larger than TMR (see FIG. 8). As a first indication, fully characterized rings with an equal number of Cy5 dyes (n=3.2 from FCS/UV-vis, see FIG. 9) either on the ring inside or outside showed an increase in the left absorption shoulder of Cy5 around 600 nm for the inner surface functionalized material (red data set). Since this shoulder is sensitive to dye aggregation, this result is consistent with dye crowding on the inside (FIG. 9*c*). When applying the qualitative HPLC screening method (Method 2 in FIG. 7) to these inside and outside surface functionalized rings, chromatograms for rings with 3.0 Cy5 dyes on the inside started to elute at later times than those with Cy5 on the outside, suggesting more hydrophobic behavior (FIG. 6*b*), consistent with dye overloading effects of the inner ring surface already becoming predominant for dye numbers as low as 3. Moreover, comparing this effect for Cy5 with the results for TMR (FIG. 6*a*) reveals larger onset shifts between the two chromatograms for Cy5 consistent with the expected size effect. It is interesting to note that overall the position of both Cy5 chromatograms is shifted to smaller retention times relative to the two TMR traces. It is believed this overall shift is due to the absence of DEAC in the Cy5 modified rings, supported by the fact that the HPLC peak structure and tailing to larger retention times observed in FIG. 3*d* is all due to DEAC only partially incorporated into the silica matrix of the C rings thereby rendering these rings more hydrophobic than their undyed counterparts (vide supra).

Functionalization the blank C rings using a Cy5 dye derivative with net negative charge was attempted. While this worked for the outer surface, it did not for the inner surface of the nanorings (data not shown). This is most likely due to repulsive electrostatic interactions between the negatively charged Cy5 dye and the negatively charged naked inner surface of C rings (from deprotonated silanol surface groups), an affect that is screened by the PEG chains on the outer surface. As shown above, neither zwitterionic TMR dye that is charge neutral nor positively charged Cy5 (FIG. 8) suffered from this problem further supporting this interpretation.

As described herein, a class of non-spherical ultrasmall fluorescent silica nanoparticles in the form of rings (C rings) were synthesized that were surface-functionalized on chemically and spatially distinct inner and outer surfaces, respectively. It was demonstrated that reverse phase HPLC is a sensitive tool able to distinguish between samples orthogonally functionalized on these surfaces with model dye-silane conjugates of different hydrophobicity, size, and charge. Results suggest that despite the small silica hydrodynamic ring size of ~10 nm and below it is possible to "hide" hydrophobic moieties on the inside of the rings, but that to accomplish this effectively their number must be carefully engineered. The class of ultrasmall nanorings described herein are expected to be of relevance for both diagnostic and drug delivery applications in nanomedicine. Furthermore, it is expected that the chromatographic methods described herein to characterize multiple spatially and chemically distinct surface chemistries on these nanoparticles will be applicable to a range of differently shaped porous nanoparticles within the ultrasmall size regime.

In addition to the conjugation of fluorescent dyes to the inside and outside surfaces of the nanorings described herein, it is expected that the results shown here will extend to other functional moieties that were previously conjugated to ultrasmall sub-10 nm NPs. These functional moieties include ligands such as targeting peptides (e.g., cRGDyC, α-MSH, PSMAi), pharmaceutical compounds, antibodies, antibody fragments, sensor dyes, DNA, RNA, and metal chelators along with metal radio labels. Work not shown here has been completed showing the successful functionalization of the C rings with metal chelators and subsequently radio labels.

Gel permeation chromatography (GPC). For the precise elution time comparison of reference samples in FIG. 3*b* and samples in FIG. 9, an automated GPC setup was also used to avoid the operator variations in the sample-loading step. Analytical scale gel permeation chromatography was performed on as made solutions prior to preparative scale GPC purification. Injection volumes were 30 μL 15 μM C rings diluted with 70 μL deionized water. The mobile phase used was the same as for the preparative scale GPC, prepared the same way directly prior to use. The column used was a 300 mm×7.8 mm Waters BioSuite High Resolution Size Exclusion Chromatography column. The separations were performed under isocratic conditions with a flow rate of 1 mL/min. Ring samples eluted within 30 minutes of injection.

High Performance Liquid Chromatography (HPLC). Two separation methods were used for analysis of inside and outside surfaces of C rings; they were as follows: For analysis using the 150 mm column: The sample was first injected onto the column in a flow of 90:10 water:acetonitrile at a flow rate of 0.75 mL/min. These conditions were maintained for 20 minutes to allow equilibration of the analyte with the stationary phase. After 20 minutes the mobile phase composition was changed to 45:55 water: acetonitrile in a step-like fashion and the baseline was allowed to equilibrate. Finally, a composition gradient of 45:55 to 5:95 water:acetonitrile was carried out for 20 minutes, during which the analyte elutes from the column. The analytical run above was followed by a short washing step and column equilibration period to ensure that all material from the previous run had eluted from the column and that the column conditions for the next sample analysis were identical to those for the previous sample analysis. The data was collected and analyzed in Empower 3. The ApexTrack integration algorithm native to the Empower 3 software was used to identify peaks and determine the area percentage associated with each eluting peak. For plotting purposes, data was exported after analysis and baseline subtracted with a blank taken before the chromatographic run using OriginLab.

For analysis using the 50 mm column: The sample was first injected onto the column in a flow of 70:30 water (with 0.1 vol % trifluoroacetic acid):acetonitrile at a flow rate of 1.2 mL/min. A linear 30-minute gradient to a final composition of 30 water (0.1 vol % TFA):70 acetonitrile was started immediately following injection of a C ring sample. The column was washed with a composition of 5 water (0.1 vol % TFA): 95 acetonitrile to ensure that all materials eluted. After the washing step, the column was equilibrated to the initial run conditions for 5 minutes before the next injection. The data was collected and analyzed in Empower 3. The ApexTrack integration algorithm native to the Empower 3 software was used to identify peaks and determine the area percentage associated with each eluting peak. For plotting purposes, data were exported after analysis and baseline subtracted with a blank taken before the chromatographic run using OriginLab.

Figure 7:
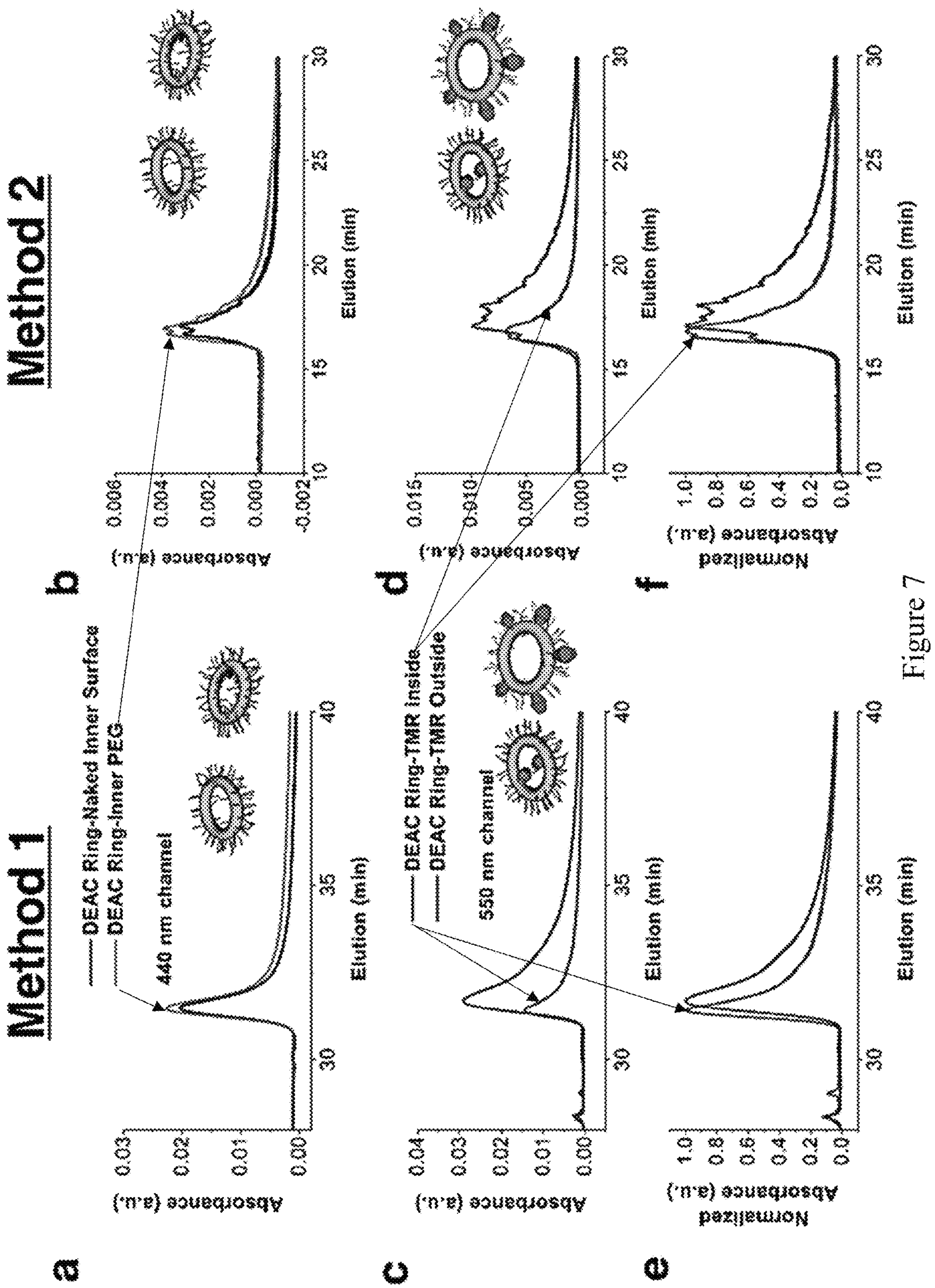
FIG. 7 shows a comparison of results from HPLC Method 1 (left) and Method 2 (right) applied to different ring batches. (a,b) Comparison of DEAC-rings with and without inner surface PEGylation, and (c,d) DEAC-rings with inside and outside TMR-functionalization, respectively. (e,f) Same data as in (c,d) but normalized to same maximum absorbance. (g) Comparison of parameter sets used for the two HPLC methods.

FIG. 7 shows the comparison of the methods on the analysis of the C ring samples from FIGS. 3 and 4, using 150 mm, and 50 mm columns, named Method 1, and Method 2, respectively. Unless otherwise stated, Method 2 is used as the primary HPLC protocol.

Fluorescence Correlation Spectroscopy (FCS). FCS experiments were performed on a home-built instrument inspired by a confocal microscope setup as described previously. A 635 nm solid-state diode laser was used as excitation source (excitation intensity 5 kW/cm') for the Cyanine5 dye and Alexa Fluor 647 was used to align and measure the size of the confocal volume due to its known diffusion coefficient.

Data was collected in sets of five consisting of five 30 s runs each then fit to a correlation function, G(τ), accounting for translational diffusion, as well as for fast photophysical processes, as shown in equation (1):

$$G(\tau)=1+\frac{1}{N}\cdot\left(\left(1+\frac{\tau}{\tau_D}\right)^{-1}\cdot\left(1+\frac{\tau}{\kappa^2\tau_D}\right)^{-\frac{1}{2}}\cdot\frac{1}{1-A}\cdot\left(1-A+A\cdot e^{-\frac{T}{\tau A}}\right)\right) \quad (1)$$

Here, N is the mean number of particles within the detection volume, and κ is the structure factor calculated from a known diffusion coefficient and given by κ=ωz/ωxy, where ωxy and ωz are the radial and axial radii, respectively, of the observation volume. τD is the characteristic diffusion time of a particle through the observation volume. τD is defined as τD=ωxy/4D, where D is the respective particle diffusion coefficient. A is the time- and space-averaged fraction of fluorophores undergoing fast photophysical processes such as photoisomerization that must be accounted for to achieve a good fit and τA is the characteristic relaxation time that is related to the fast photophysical process. The Stokes-Einstein relation was applied to determine particle diameters, equation (2):

$$d=2\frac{k_BT}{6\pi\eta D} \quad (2)$$

with kB being the Boltzmann's constant, T being the absolute temperature, and η being the dynamic viscosity. The average number of dyes per particle, n, was calculated according to equation (3):

$$n=\frac{C_{dye}}{C_{particle}} \quad (3)$$

Here $C_{dye}$ is the measured dye concentration derived from the dye extinction coefficient using the relative absorbance, and $C_{particle}$ is the particle concentration determined by FCS.

Example 2

This example provides a description of methods of making and uses of nanorings of the present disclosure.

Topology is a pervasive topic across a wide range of scientific disciplines. While effects of size, shape, or composition of nanomaterials on biological response have been widely studied, much less is known about how topology modulates biological properties. In this example, the biodistribution in mice of silica nanomaterials around 10 nm in size with four different topologies: spheres, hollow beads, cages, and rings was studied. In contrast to regular spherical particles, whose uptake in organs (e.g., liver, spleen) of the reticuloendothelial system (RES) increases with increasing diameter, for this sequence, record low RES uptake with increasing size was surprisingly observed. Rings get effectively cleared via the kidneys for diameters larger than 15 nm, i.e. well above the cut-off for renal clearance about 6 nm. Results suggest that topology is a hitherto neglected parameter in materials design for applications in nanomedicine, enabling low RES uptake and efficient renal clearance for object diameters well above 10 nm.

Figure 15:
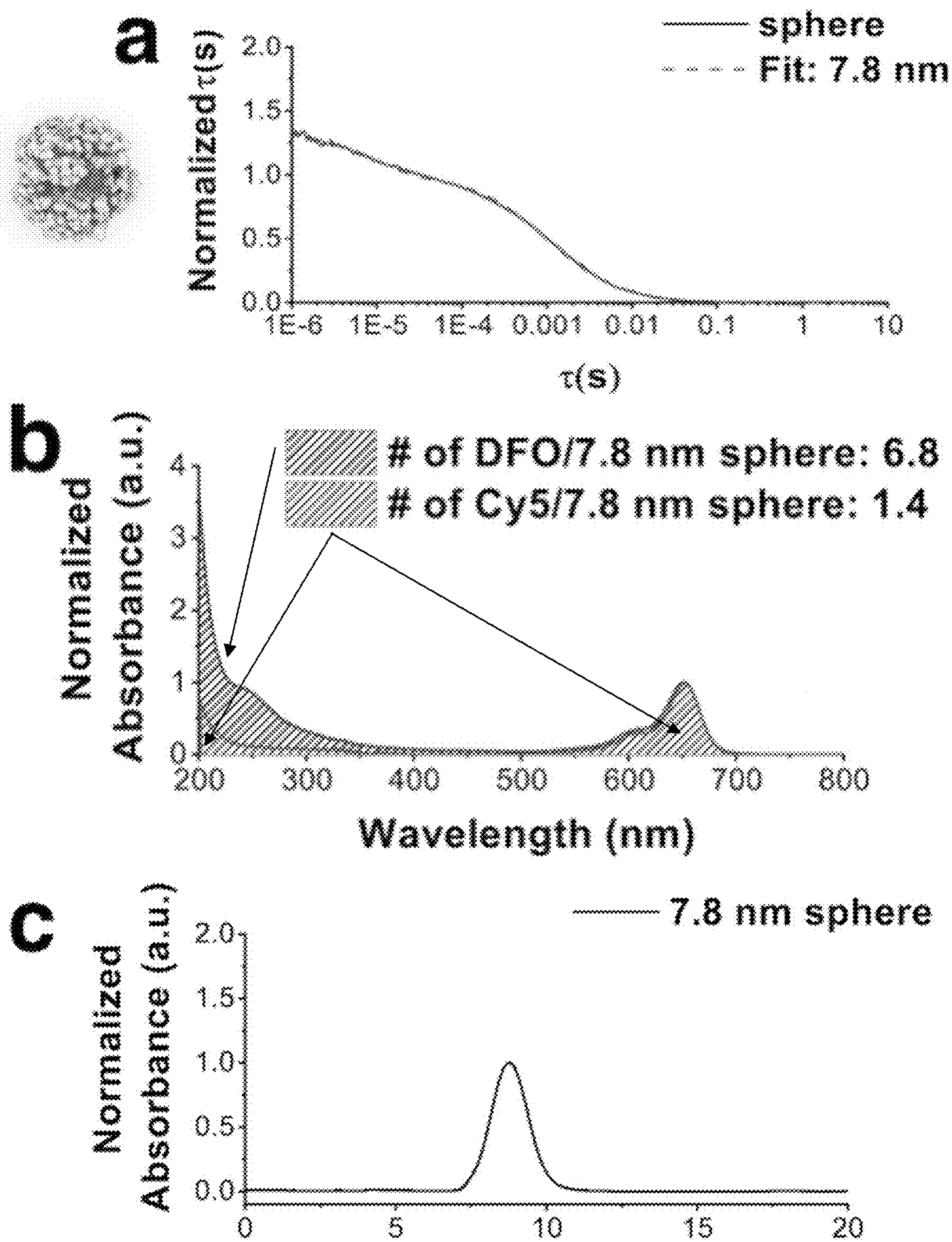
FIG. 15 shows comprehensive characterization of particles with different topologies. Characterization of spherical dot (a-c), hollow bead (d-f), cage (g-i), and ring (j-l) particles. (a,d,g,j) FCS correlation curves with their fits for hydrodynamic sizes. (b,e,h,k) Deconvolution of the UV-vis spectra for the calculation of numbers of dyes and radiolabel chelators per particle. (c,f,i,l) GPC chromatograms for purified nanoparticles showing single peaks in all cases. Please note that GPC peak position in time does not directly correlate with size as shifts may reflect GPC configuration changes (e.g., new columns or the like) over time (not all GPCs were taken on the same day). (m) Results of TEM size analyses (averaged over 100 particles) for spherical dot, hollow bead, cage, and ring samples.
Figure 15:
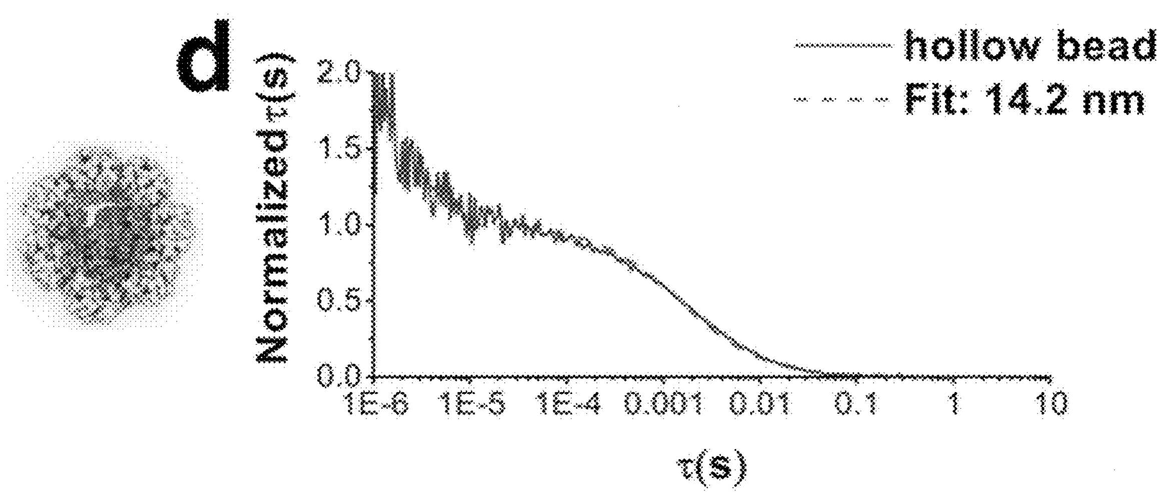
Figure 15:
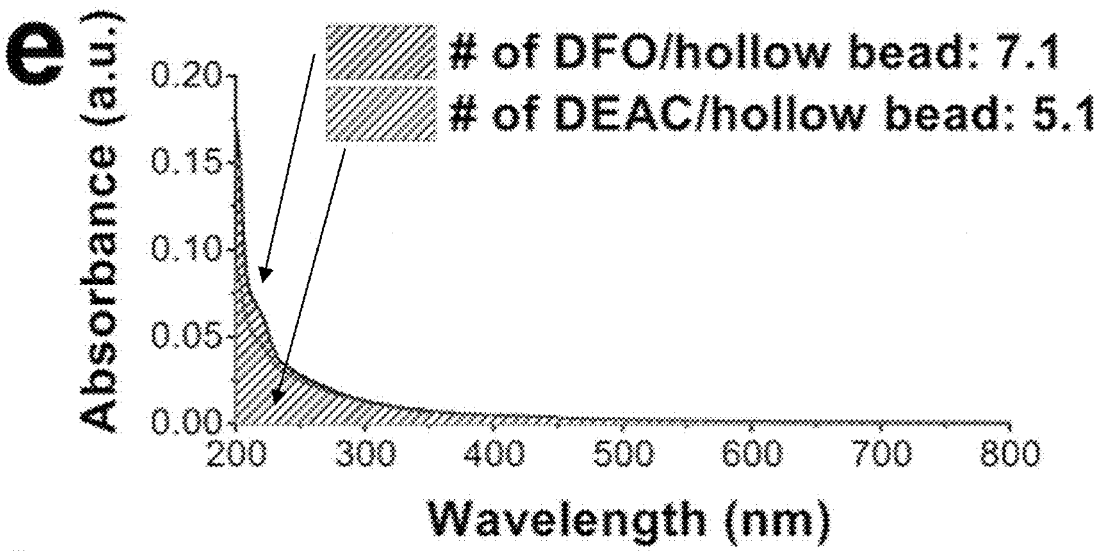
Figure 15:
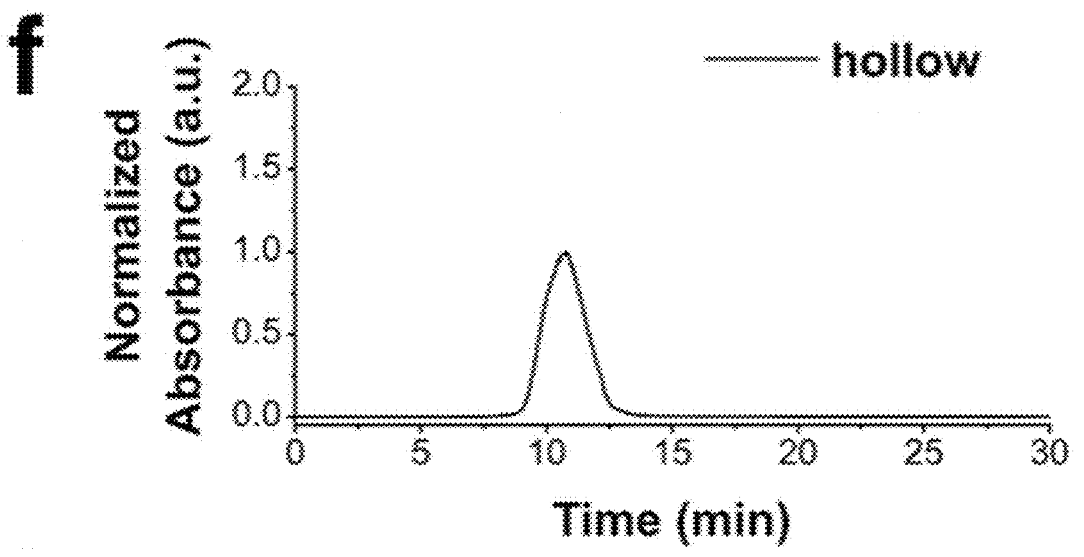
Figure 15:
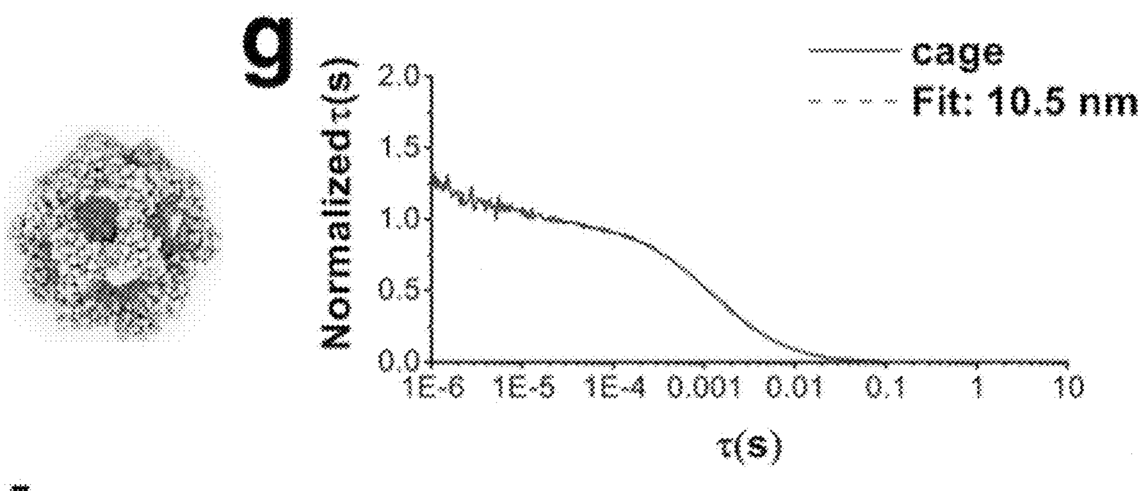
Figure 15:
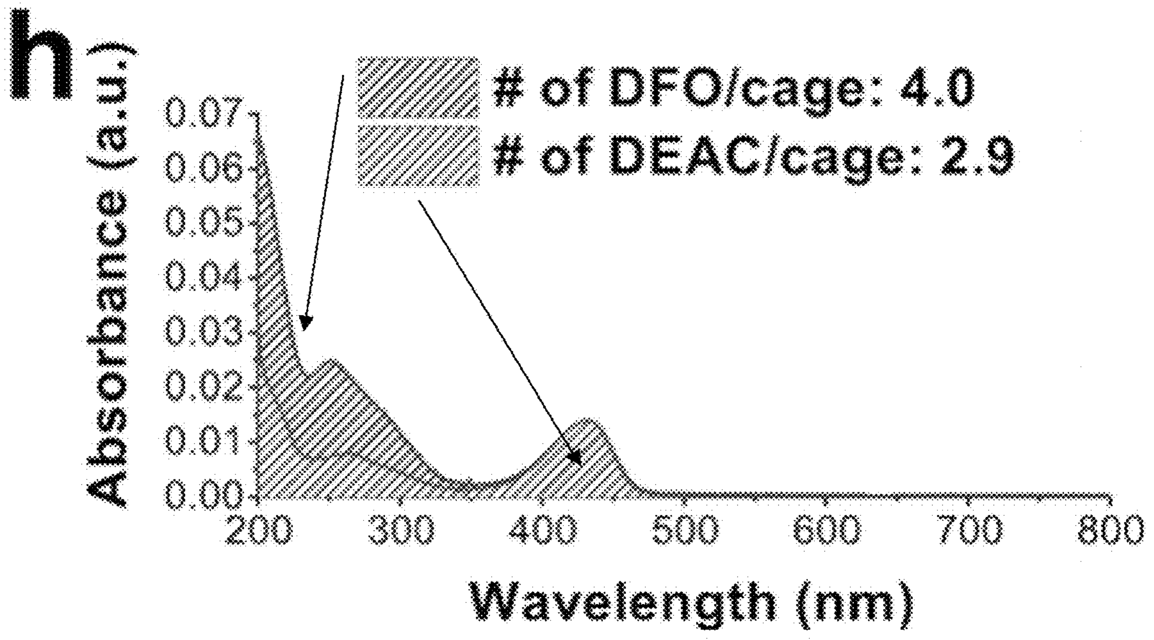
Figure 15:
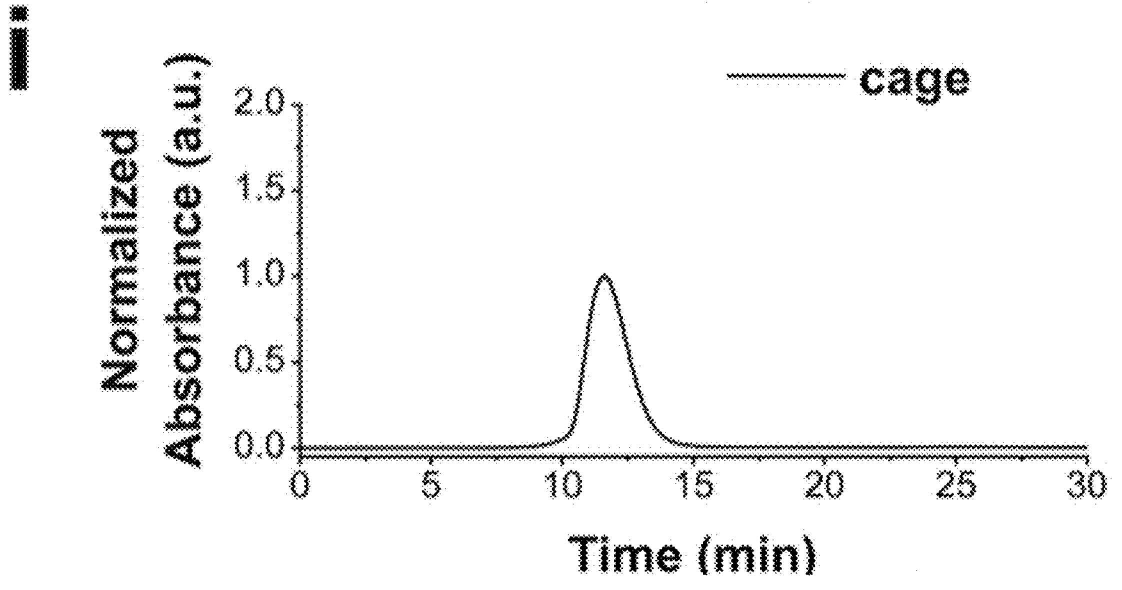

Silica nanoparticles (NPs) with ~10 nm diameter were synthesized as described herein and according to previously known methods from tetramethyl orthosilicate (TMOS), cetyl-trimethylammonium bromide (CTAB), and 1,3,5-trimethylbenzene (mesitylene, TMB) in aqueous solutions as a way to keep structural parameters, other than topology (e.g., size, shape, surface chemistry, surface charge), similar across all particles. NP topology was engineered by adjusting CTAB and TMB concentrations. In their absence, ~4 nm diameter spherically shaped silica cores were formed. When TMB swollen CTAB micelles were introduced, ~2 nm-sized primary silica clusters self-assembled on their surfaces, leading to the formation of silica rings, cages, or hollow beads depending on reagent ratios (Methods). Dyes endowed the particles with fluorescence (Methods), while poly(ethylene glycol) (PEG) coatings (Methods) provided for steric stability and improved biocompatibility. Deferoxamine (DFO) was attached onto all particle surfaces as a chelator for zirconium-89 ($^{89}Zr$, $t_{1/2}$=78.4 h), enabling quantitative serial positron emission tomography (PET) imaging and biodistribution analyses (Methods). Particles were purified by gel permeation chromatography (GPC) and compositions characterized before final use (FIG. 15).

Figure 11:
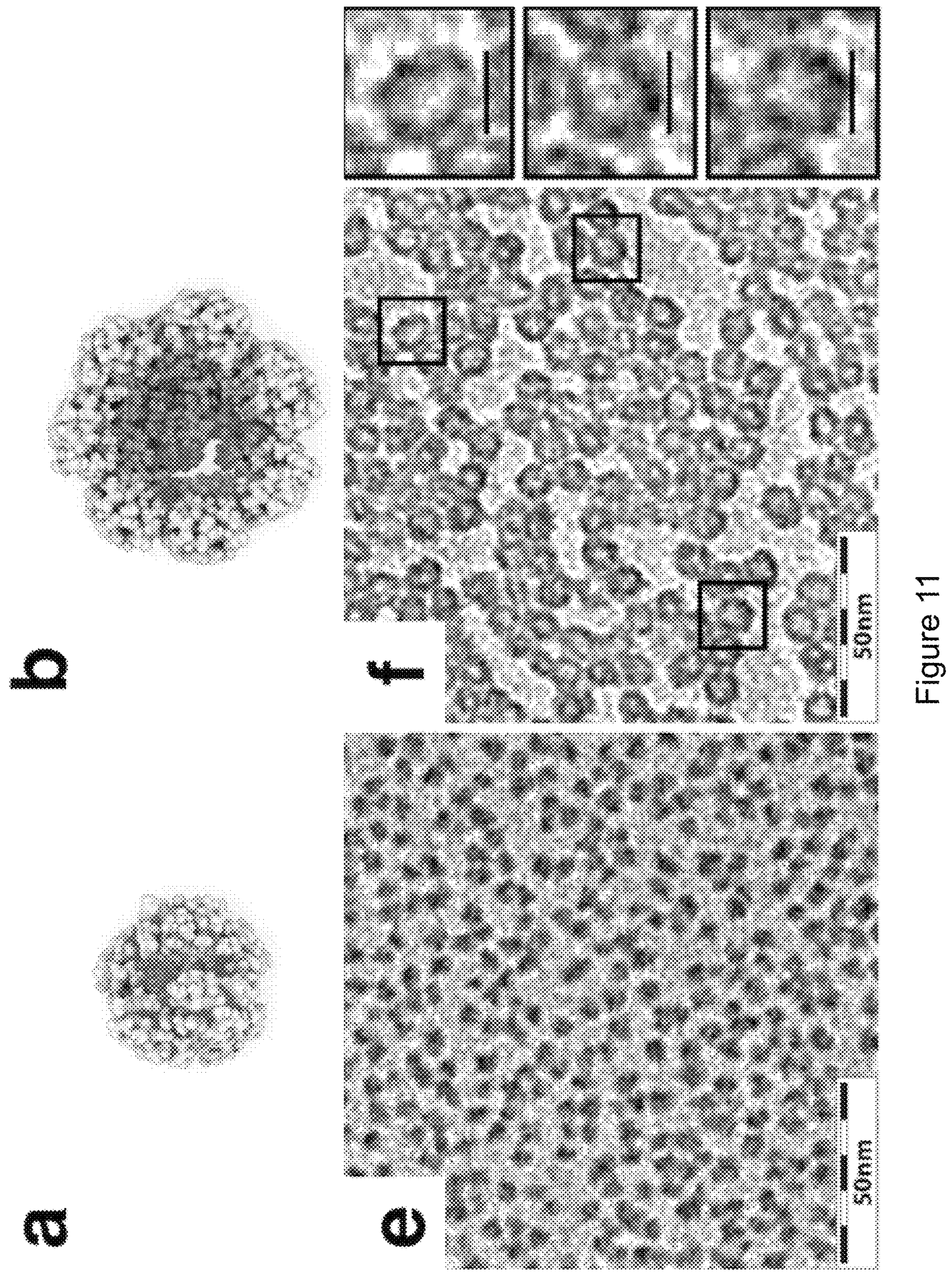
FIG. 11 shows the four inorganic (silica) nanoparticle topologies studied. Illustration of silica sphere (a), hollow bead (b), cage (c), and ring (d) topologies, together with representative EM images (e), (f), (g), and (h), respectively. Insets in (f), (g), and (h) show individual particles, including TEM (left), and cryo-EM (right) images in (g) of the two most common projections of the dodecahedral cage, i.e., the two-fold (top) and five-fold (bottom) projections, as well as in (h) of rings lying down, and edge-on from TEM (left), and cryo-EM (right), respectively (scale bars 10 nm).
Figure 11:
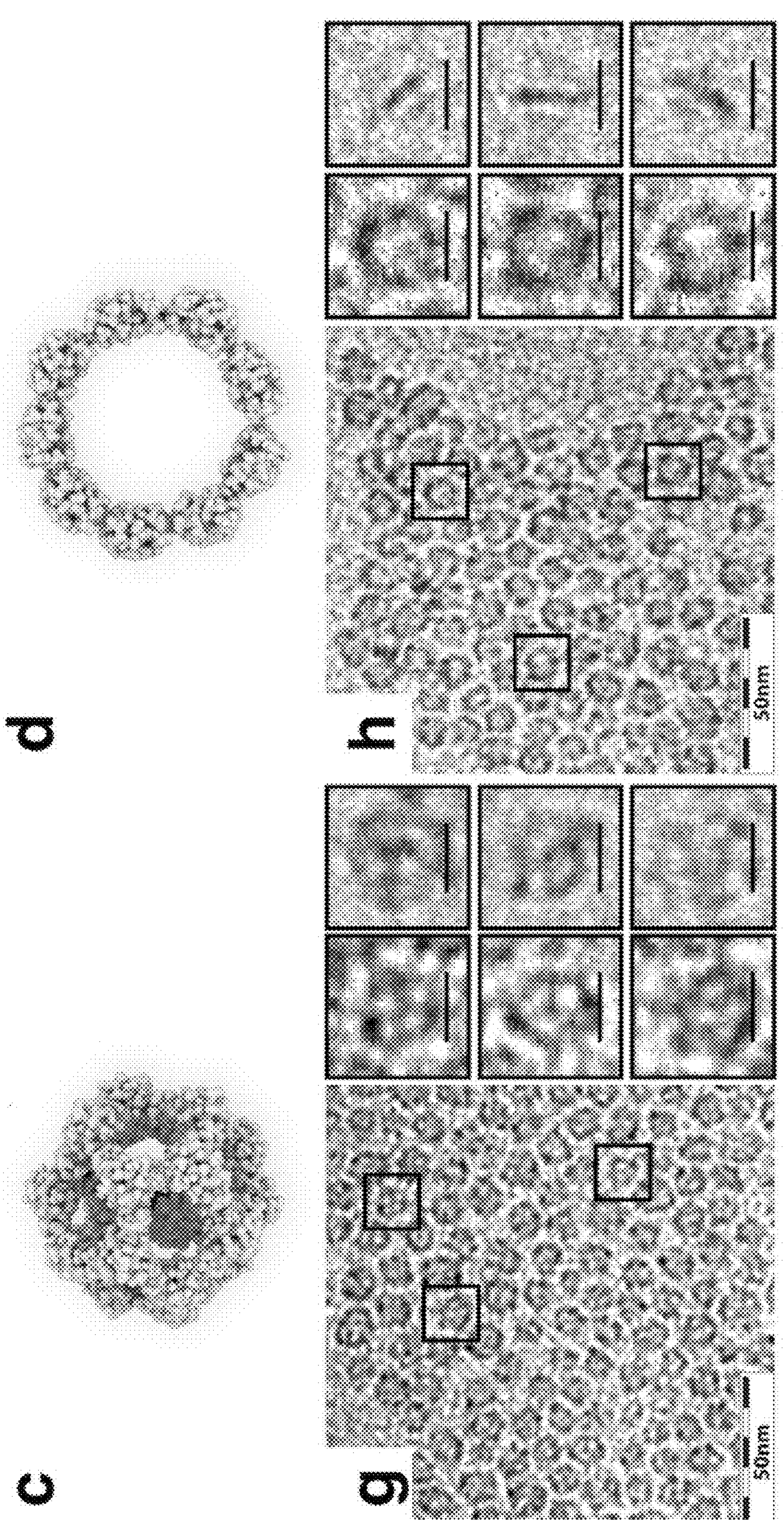
Figure 16:
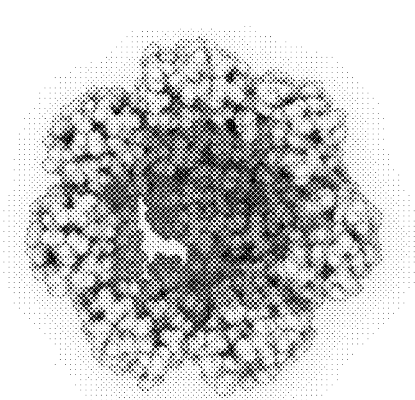
FIG. 16 shows TEM images and tilt series of hollow beads. (a) TEM image of a hollow bead sample, with illustrations of particle topology on the right. (b) TEM images of a tilt series taken for a hollow bead sample from 0° to 45° angles. (c) Zoom-in images of individual hollow beads taken from regions highlighted by red squares in the images shown in (b).
Figure 16:
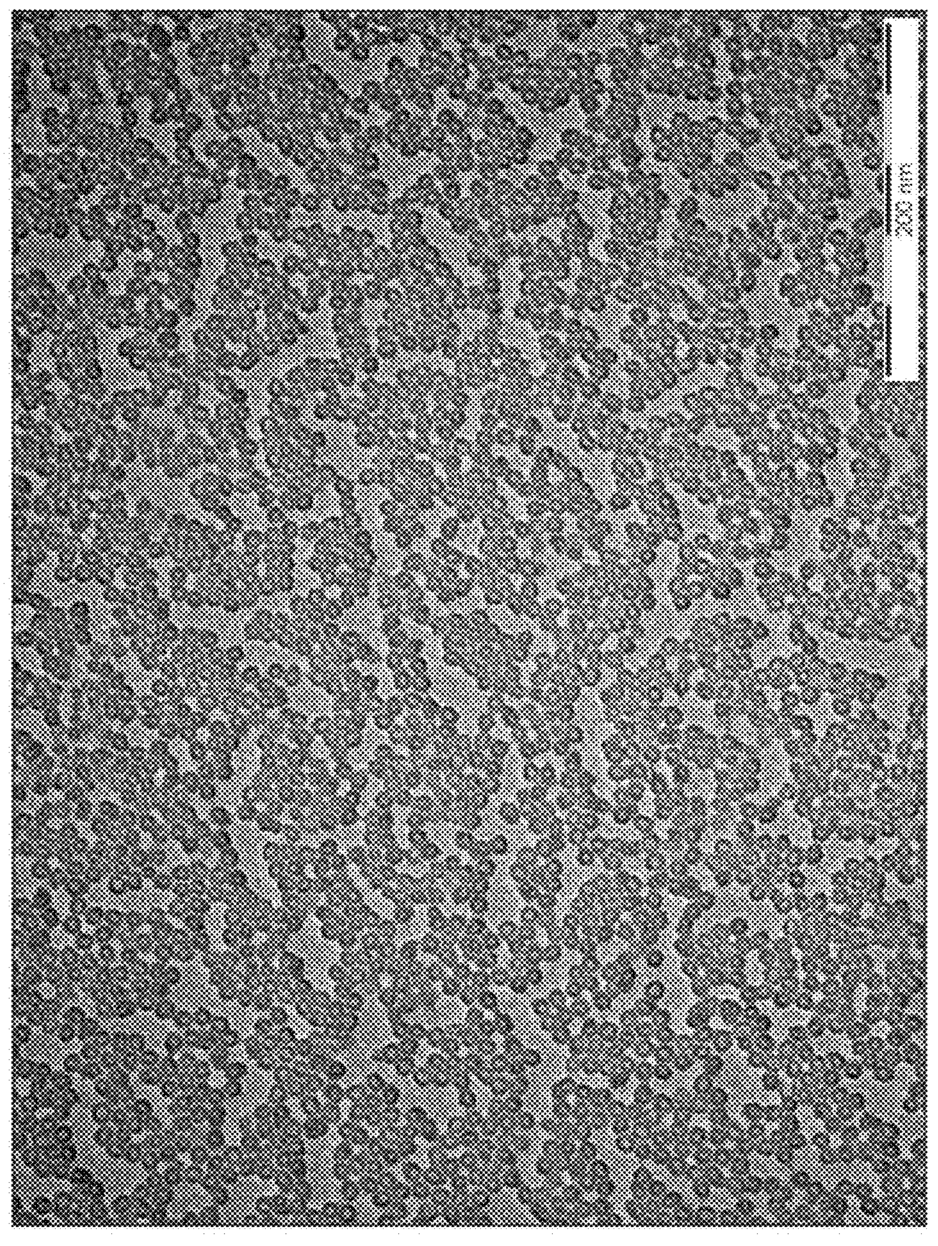
Figure 16:
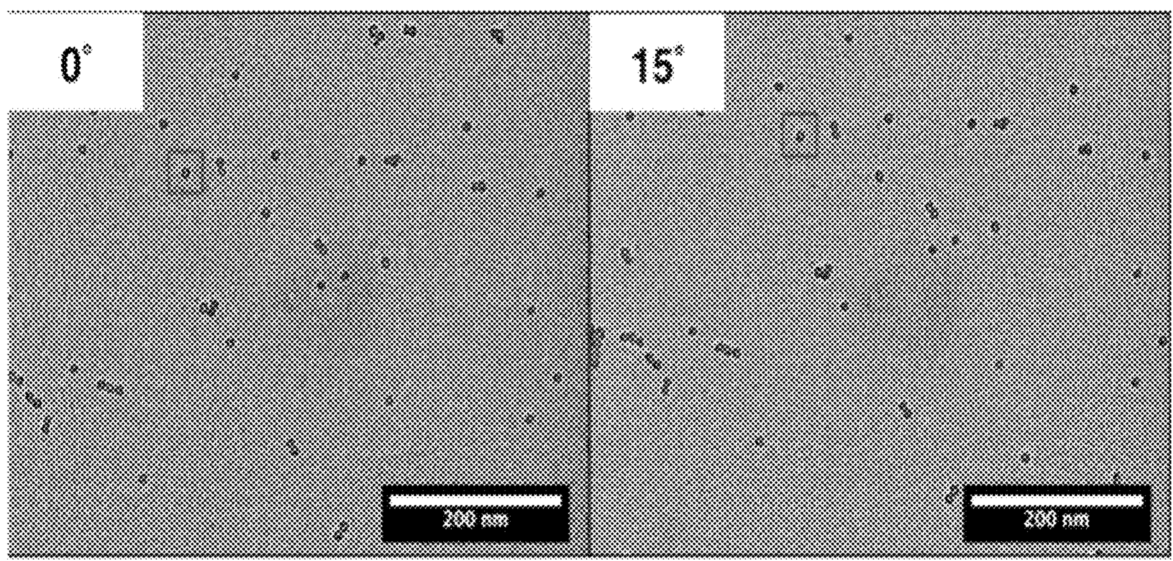
Figure 16:
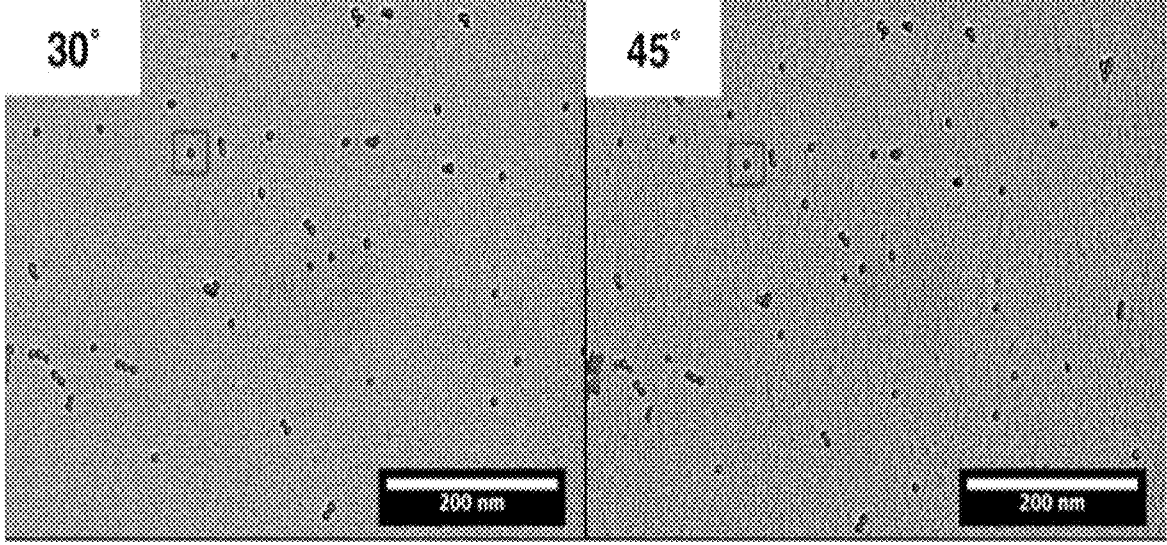
Figure 16:
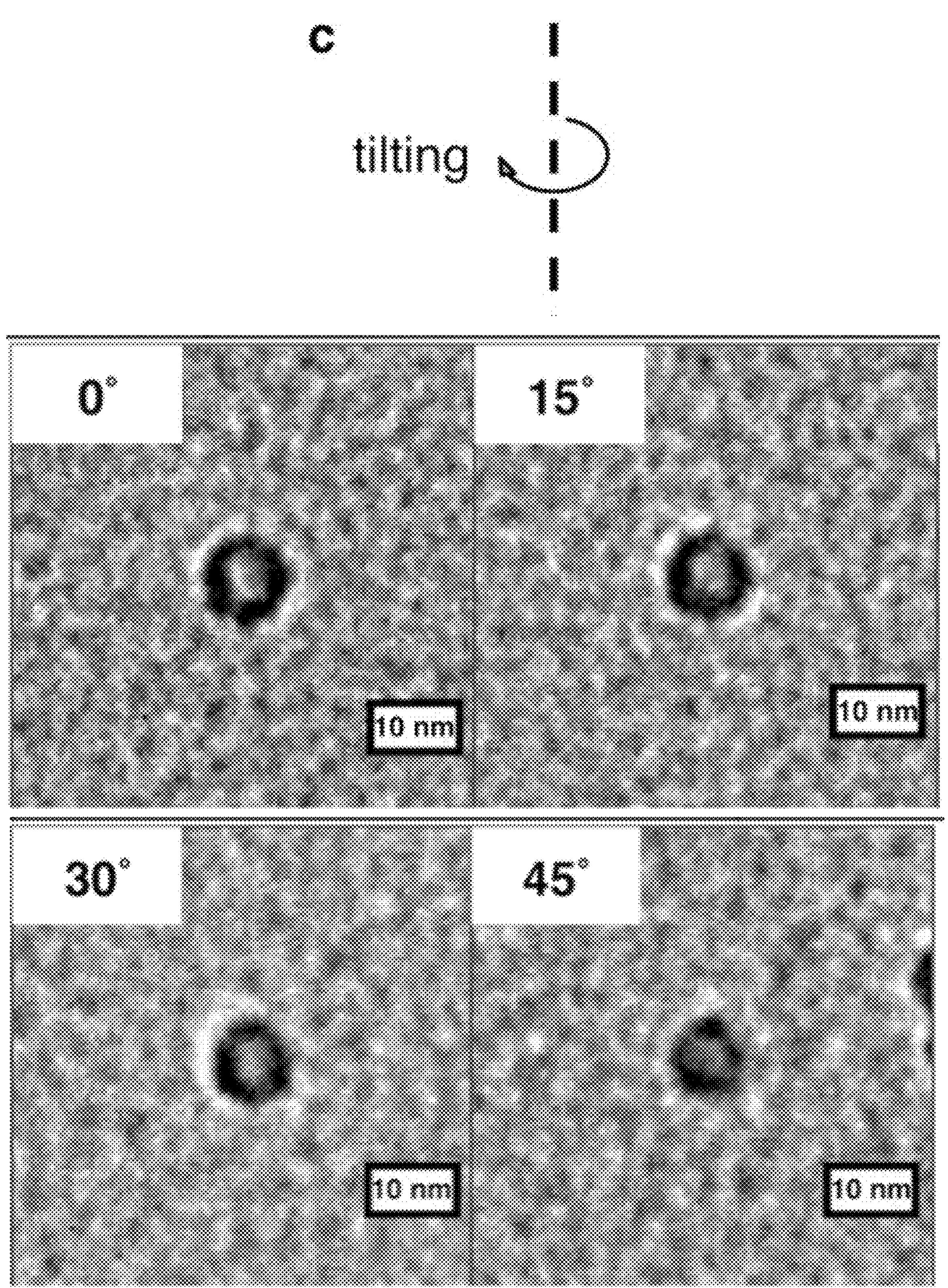
Figure 17:
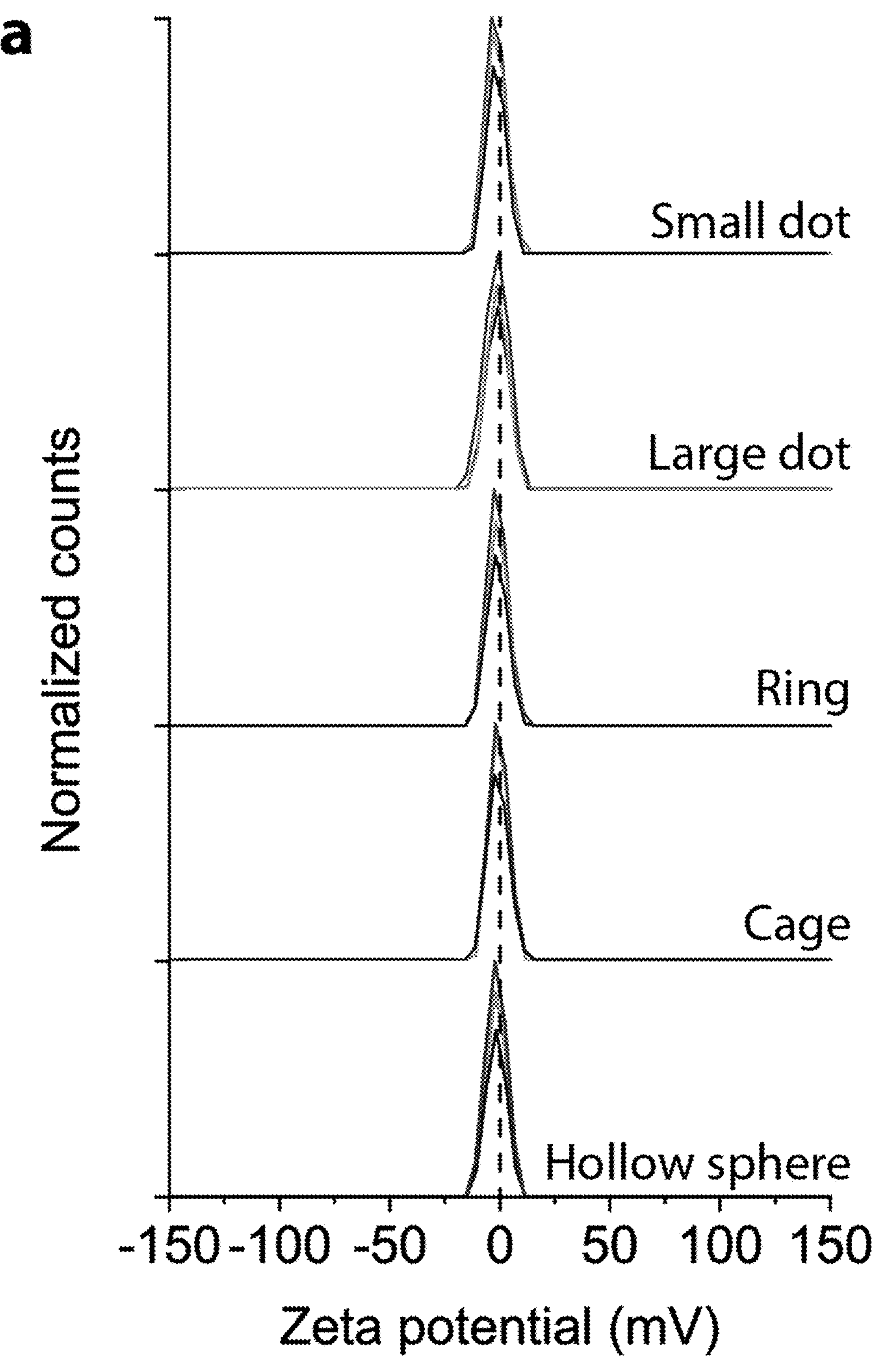
FIG. 17 shows zeta potential measurement of different topologies. Zeta potential distribution of different topologies (a), for which each sample was measured three times and the results were then averaged (b).
Figure 17:
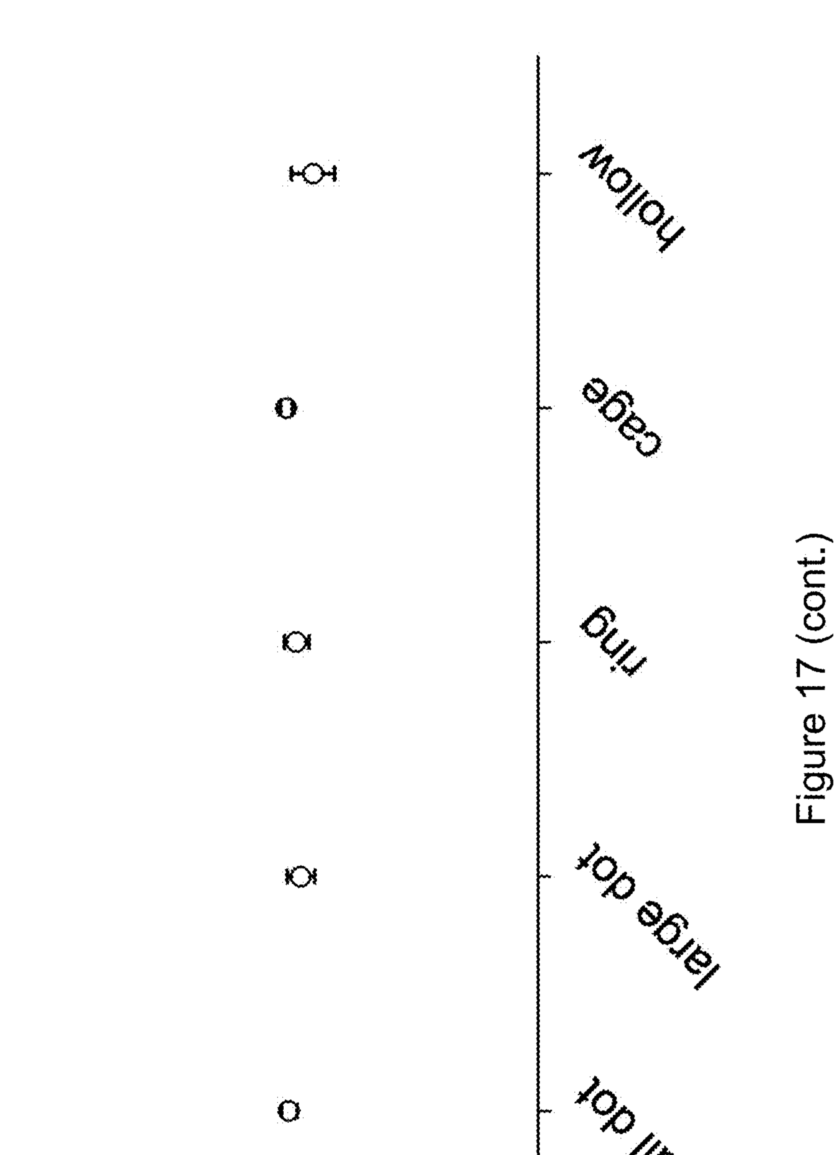

Hydrodynamic (or equivalent hydrodynamic) particle diameters (Methods) were determined using fluorescence correlation spectroscopy (FCS), while particle topology and silica core diameters were characterized by transmission and cryogenic electron microscopy (TEM, cryo-EM). The larger size of hollow beads, cages, and rings relative to spheres was easily discerned (FIG. 11), while detailed inspection (see insets FIG. 11) revealed established features and projections consistent with cage and ring topologies. The structure of hollow beads formed around CTAB micelles was confirmed with a TEM tilt series (FIG. 16). Diameters measured by TEM for spheres, beads, cages, and rings were 7.3 nm, 10.8 nm, 12.3 nm and 12.1 nm, while their (equivalent) hydrodynamic FCS sizes were 7.8 nm, 14.2 nm, 10.5 nm, and 8.2 nm, respectively (FIG. 15). While for spherical and hollow particles FCS provides a larger diameter than TEM owing to PEG and dragged water shells, it underestimates the diameters of cages and rings due to the assumption of a spherical shape in the model-based analysis (Methods). Zeta-potential measurements for all particles showed values close to zero, consistent with successful PEGylation (FIG. 17).

Figure 12:
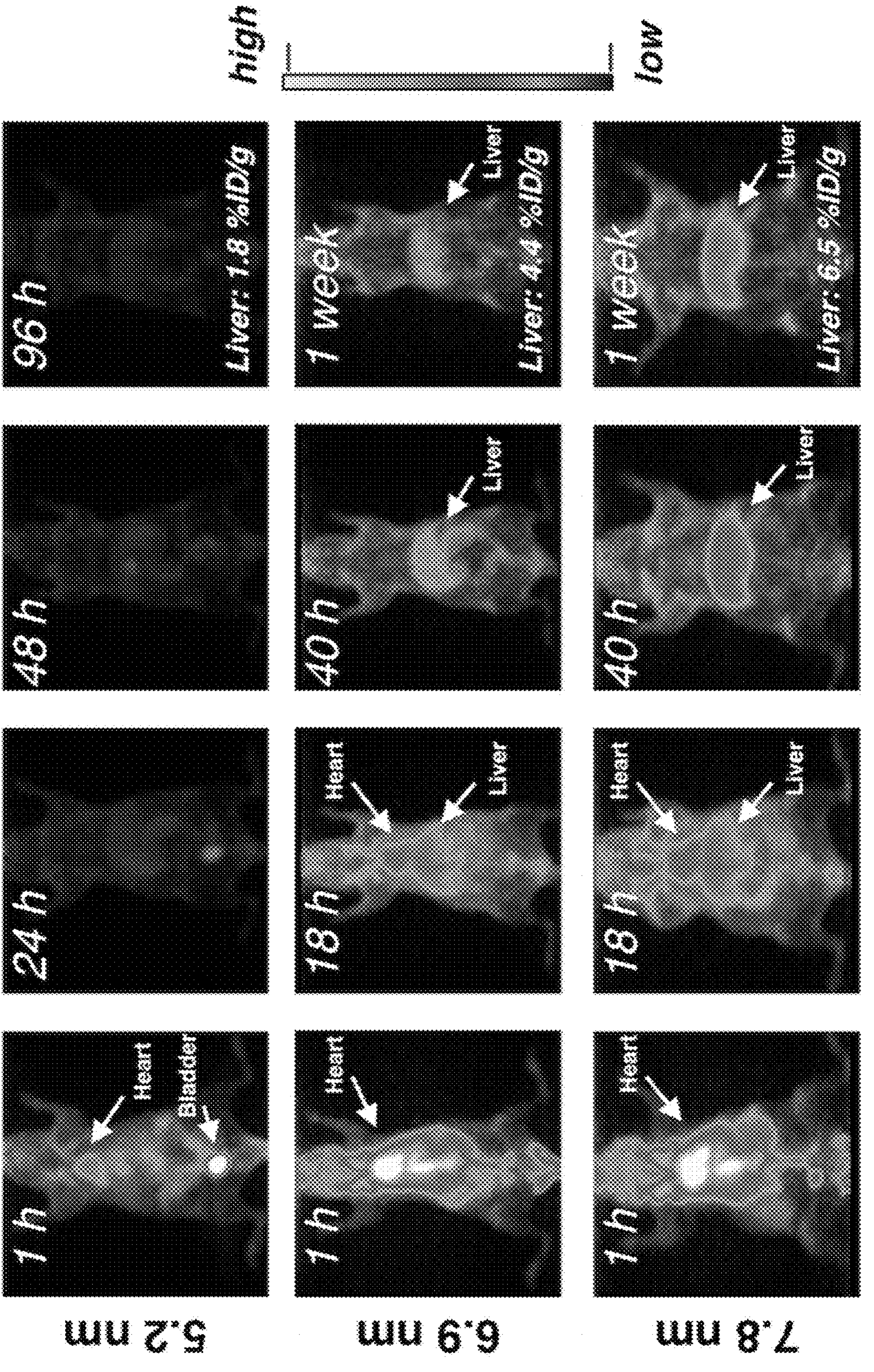
FIG. 12 shows in-vivo and ex-vivo studies of different sized spherical silica dots in mice. (a) MIP images of i.v.-injected 5.2, 6.9, and 7.8 nm FCS sized $^{89}$Zr-labeled spherical silica nanoparticles over a one-week period demonstrating hepatic uptake values of 1.8, 4.4, and 6.5% ID/g, respectively, (n=1 mouse/particle size). (b) Biodistribution studies for 5.2 (orange) and 7.8 nm (green) FCS sized spherical nanoparticles (n=3 mice/particle size, $p<0.001$) one week after i.v. injection. (c) Metabolic cage studies (n=3 mice/particle size) with 5.2 and 7.8 nm FCS sized spherical nanoparticles showing renal (yellow) and hepatic (brown) clearance, along with the remaining carcass (grey) activity, one week after i.v. injection ($p<0.001$). (d) Time-dependent renal/hepatic clearance levels for these same cohorts over a 6 to 168 hour period (7 days) as a function of spherical particle size (cumulative urinary clearance $p<0.001$, rate of accumulation $p=0.017$). Error bars are calculated from the standard deviation of n=3 mice for each experiment.
Figure 12:
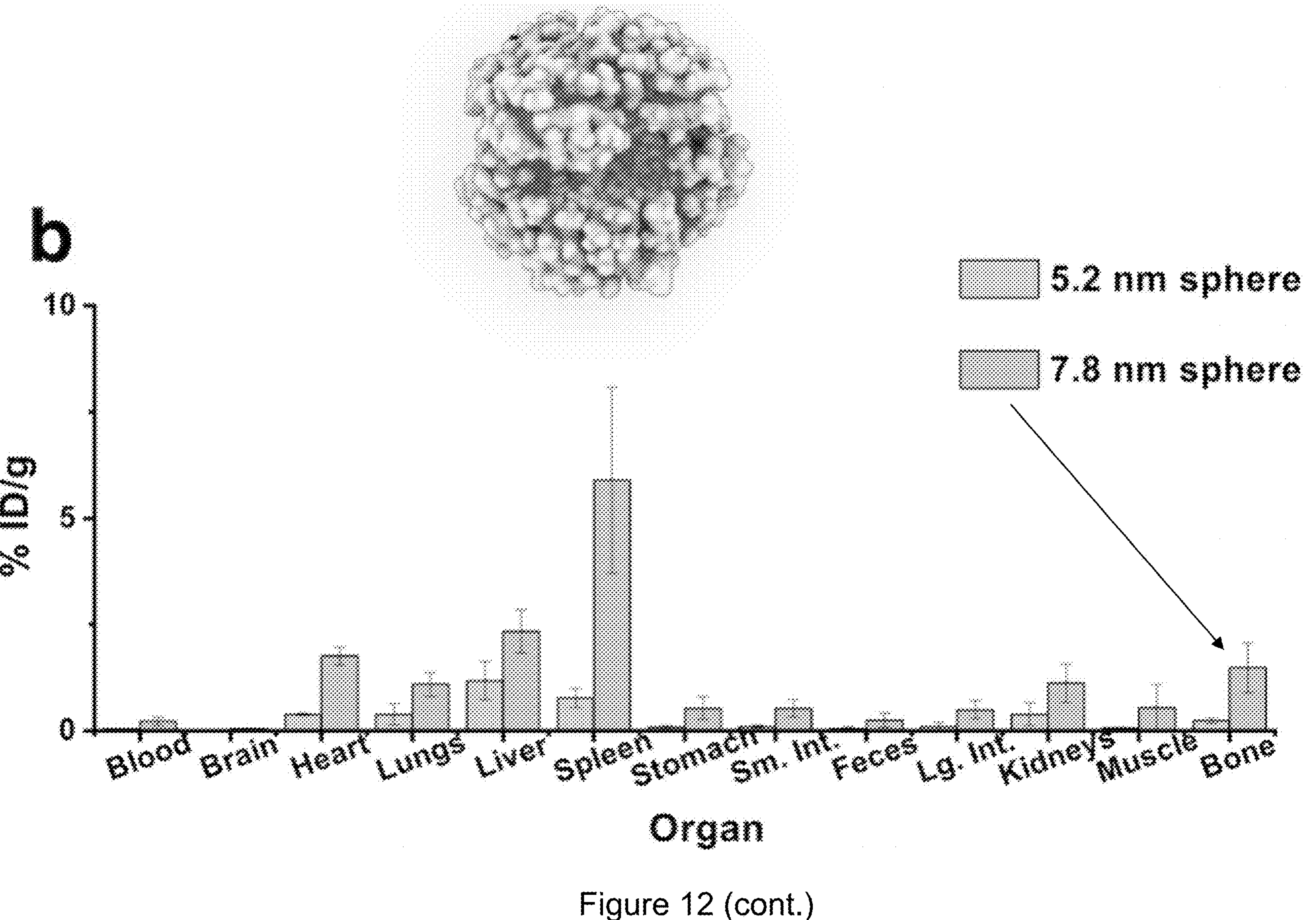
Figure 12:
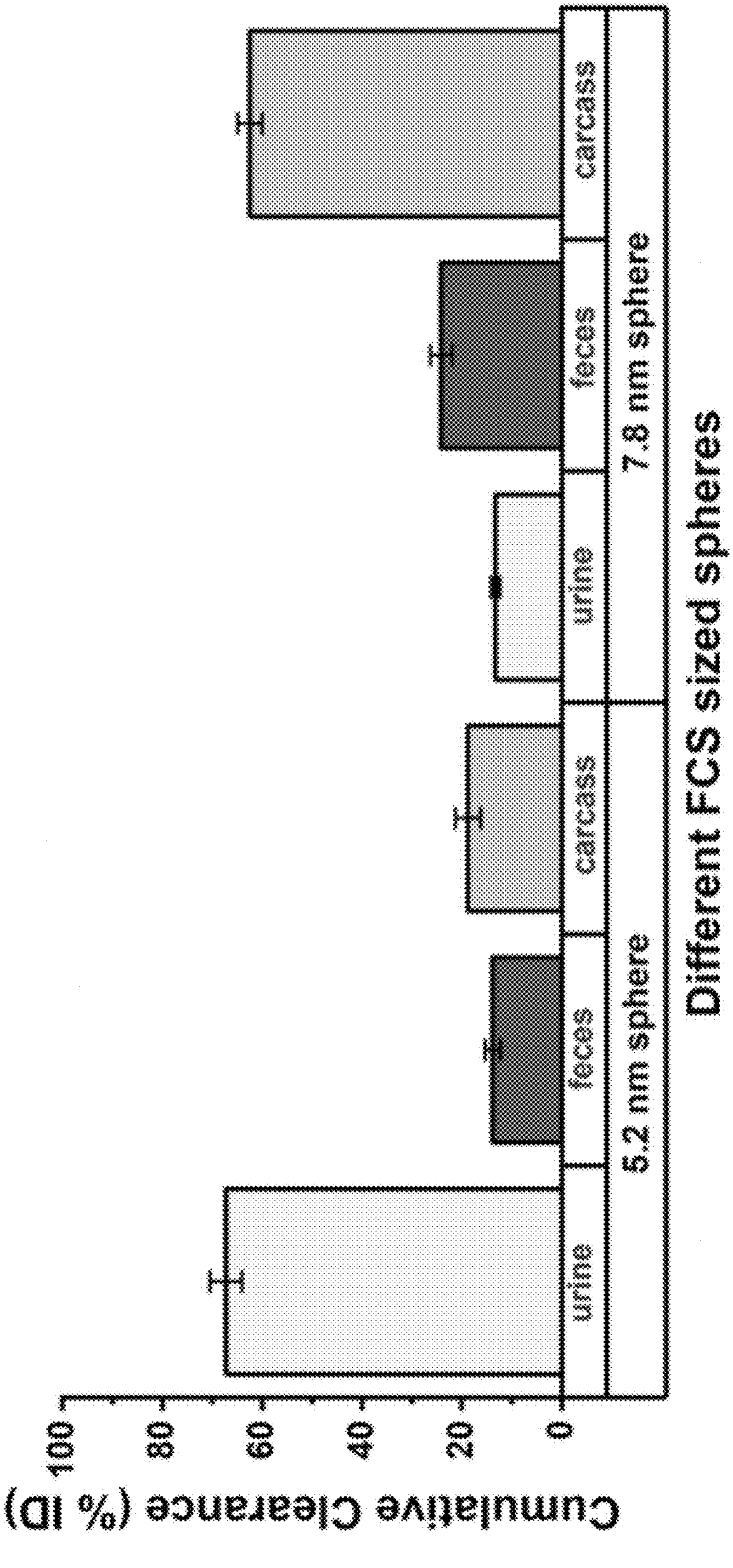
Figure 12:
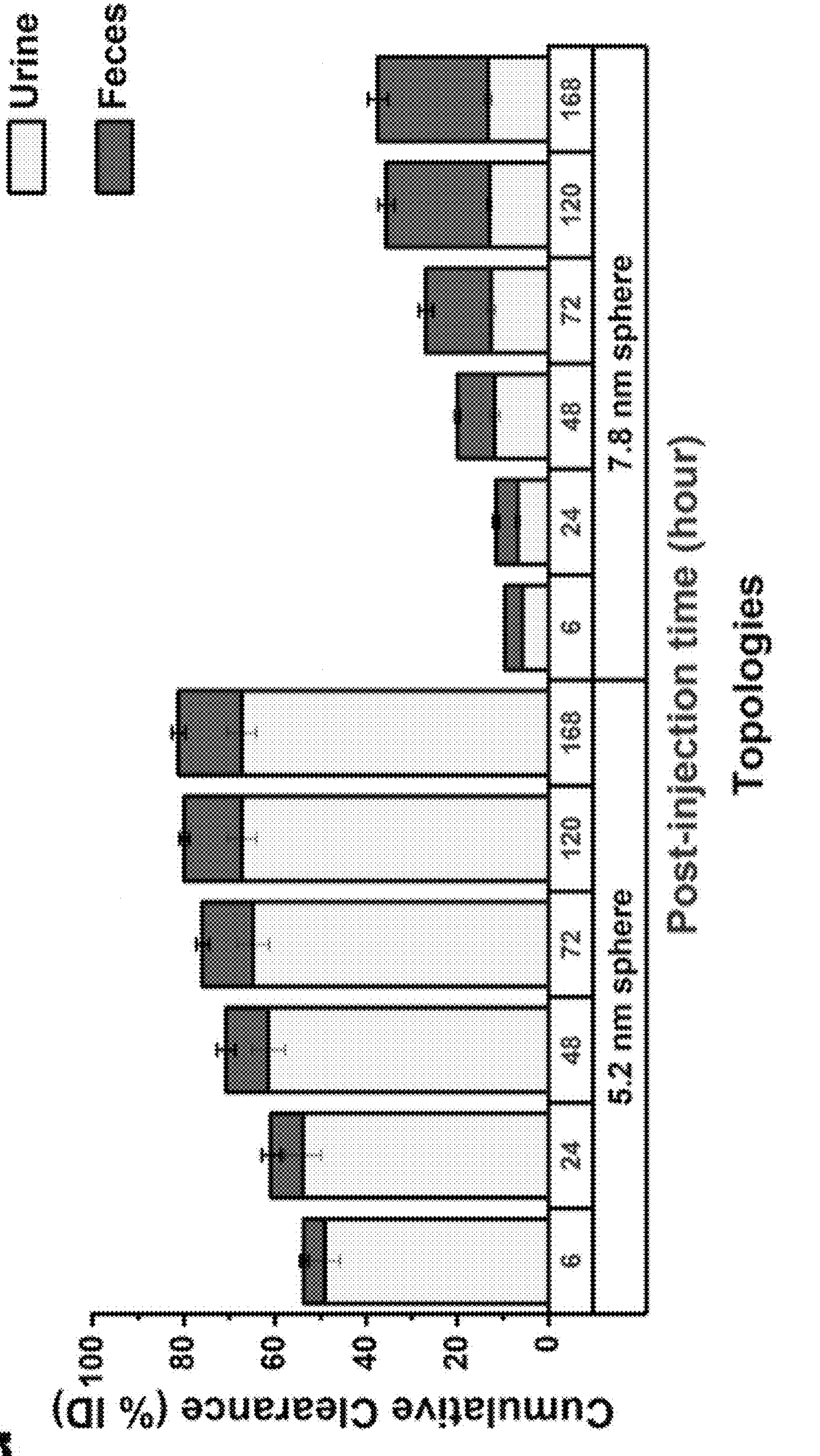
Figure 18:
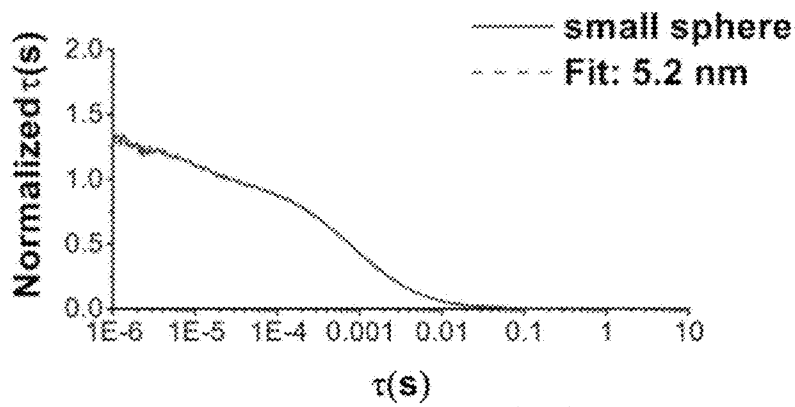
FIG. 18 shows comprehensive characterization of spherical dots with different sizes. Characterization of small-sized (a-c), medium-sized (d-f), and large-sized (g-i) spherical dots. (a,d,g) FCS correlation curves with their fits for hydrodynamic sizes. (b,e,h) Preparative scale GPC chromatograms for purified nanoparticles. (c,f,i) Deconvolution of the UV-vis spectra for the calculation of numbers of dyes and radiolabel chelators per particle.
Figure 18:
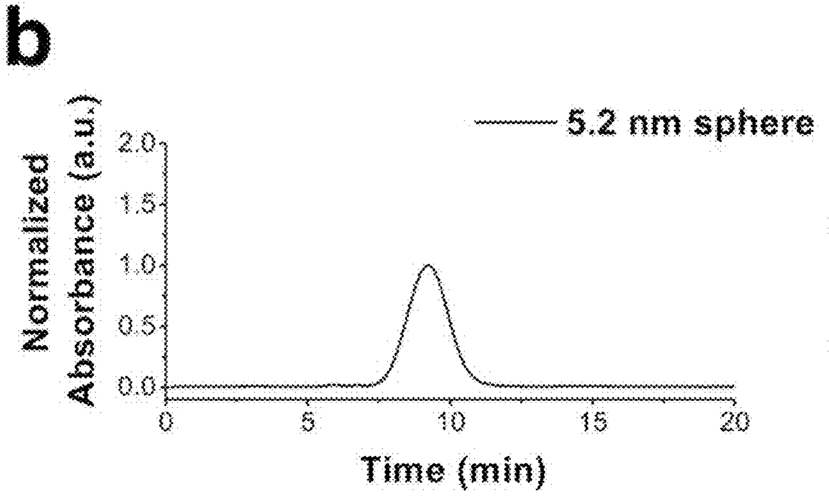
Figure 18:
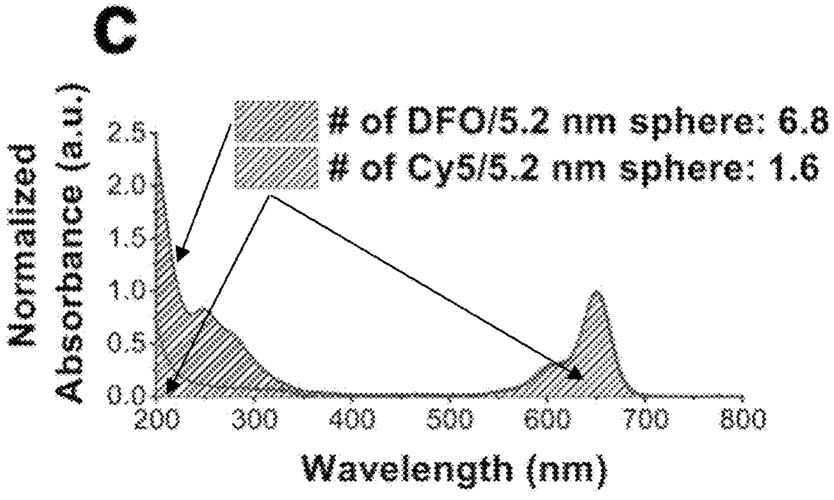
Figure 18:
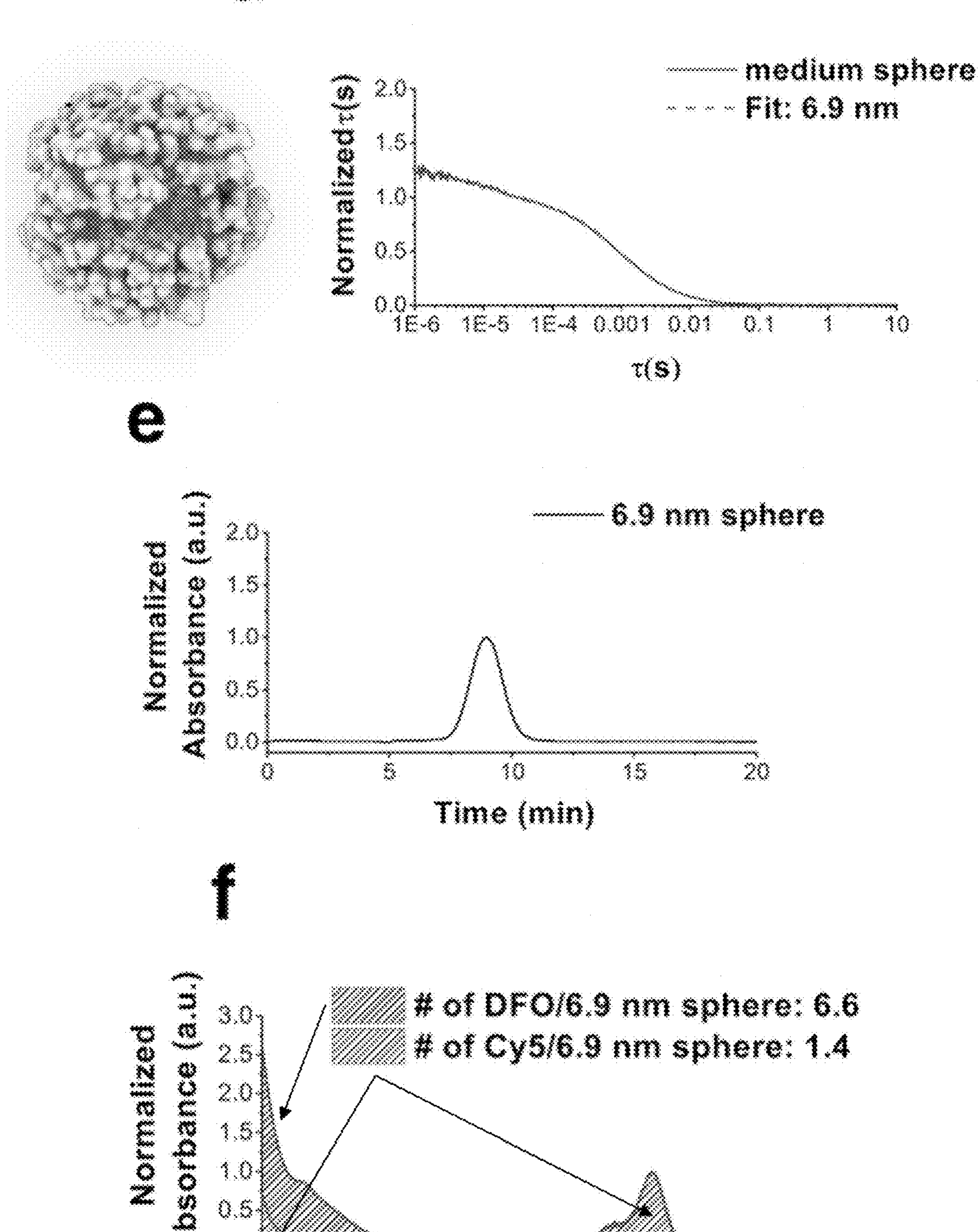
Figure 18:
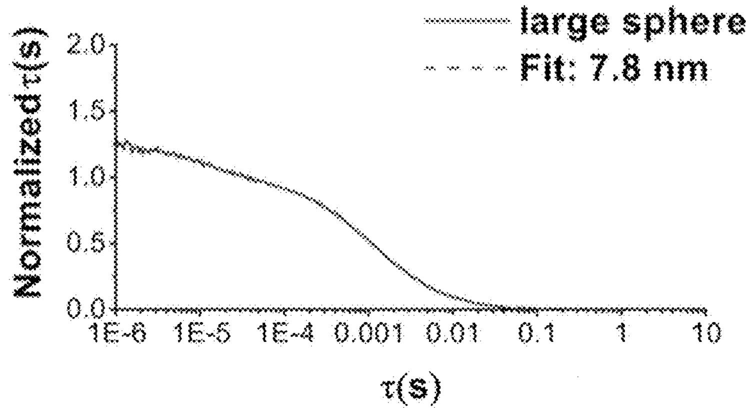
Figure 18:
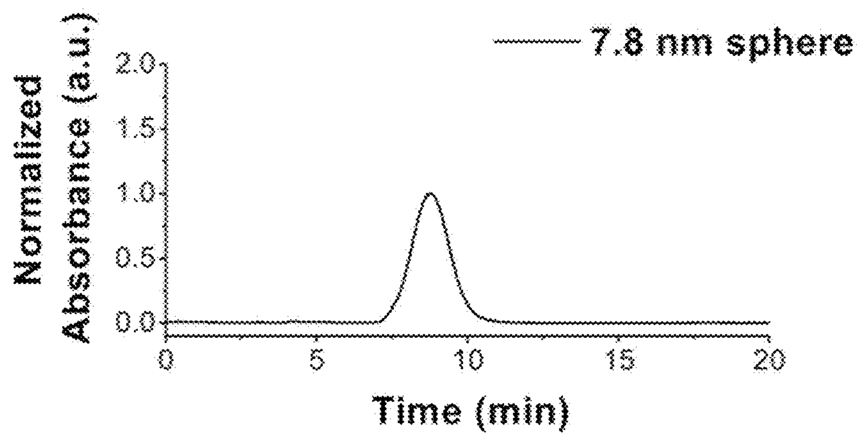
Figure 18:
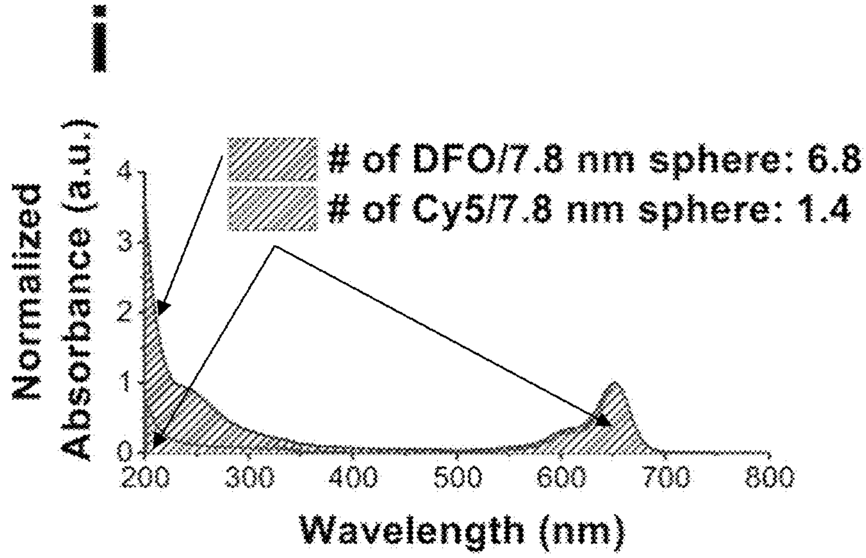

NP biodistribution is typically dependent on diameter below 10 nm; e.g., liver uptake substantially increases with increasing particle size, while the ability to clear via the kidneys diminishes. To illustrate this behavior, spherical dots were radiolabeled with 5.2 nm, 6.9 nm and 7.8 nm hydrodynamic (FCS) diameters (FIG. 18) with $^{89}Zr$. These particle tracers were intravenously (i.v.) injected into healthy nude mice. Serial PET scans were acquired over a one-week period (Methods) to study time-dependent particle pharmacokinetics (PK) and whole-body biodistribution. From selected coronal PET images (maximum intensity projections, MIPs, FIG. 12*a*), liver uptake was found to increase from 1.8 to 4.4 to 6.5% ID/g. Ex vivo biodistribution studies were performed one week after i.v. injection to quantitatively evaluate organ/tissue-specific uptake of small (5.2 nm) and larger-size (7.8 nm) particle tracers, respectively (Methods). Similar to findings on PET, as dot size increased, mean tissue-specific uptake values went up in the heart (blood pool) and kidneys, as well as in organs of the RES (FIG. 12*b*), namely the spleen (~0.8 to 6% ID/g), liver (~1.2 to 2.3% ID/g), bone marrow (~0.2 to 1.5% ID/g), and lungs (~0.4 to 1.1% ID/g). Organ-specific differences were statistically significant ($p<0.001$). Time-dependent particle tracer activities in urinary and fecal biological specimens were monitored using a metabolic cage set-up (Methods) following i.v.-injection of small and large spheres. At one week post-injection (p.i.), cumulative urinary clearance (% ID, FIG. 12*c*) exhibited a substantial drop from around 67 to 13% ID as particle size increased from 5.2 nm to 7.8 nm, whereas a rise in fecal clearance was observed (i.e., ~14 to 24% ID). Retained activity, i.e., dots remaining in the carcass, accounted for about 19 and 63% ID for 5.2 nm and 7.8 nm particles, respectively, suggesting ~3 times less total clearance for the larger dots. Adjusting for these different clearance routes, statistically significant differences ($p<0.001$) were found between particle sizes. In time-dependent clearance profiles from metabolic cage studies up to one-week p.i. (FIG. 12*d*), while the urinary clearance of 5.2 nm dots was nearly 50% ID at 6 hours p.i., order of magnitude lower urinary clearance was seen for 7.8 nm dots at a similar p.i. time. Statistical significance was achieved for both cumulative urinary clearance at 168 hours p.i. ($p<0.001$), as well as for the rate of accumulation ($p=0.017$) across particle sizes.

Observations of progressively higher RES uptake with concomitant decreases in renal excretion as particle size increases are consistent with prior studies. Surprisingly, however, these trends were inverted when moving to objects with even larger sizes, but different topologies in the form of hollow beads, cages, and rings measuring 10.8 nm, 12.3 nm, and 12.1 nm (TEM) in diameter, respectively. Results of serial PET imaging and biodistribution studies up to one-week p.i. in healthy mice after $^{89}Zr$ radiolabeling and i.v. particle injection are compared to the PK profile of the 7.3 nm (TEM) diameter dots in FIG. 13. At early p.i. time points (i.e., ~1 hour), high particle tracer activities were observed in the heart and liver for all topologies, as expected, consistent with higher vascular perfusion to these organs. By 40-48 hours, however, cardiac activities had substantially decreased from that seen at 18-24 hours across all topologies, except for cages. Regarding clearance properties, bladder activity was already detectable on MIP images for hollow beads and rings at early time-points (FIG. 13*a*, col 1), while hepatic activity became apparent at ~24 hours p.i. for hollow beads and spheres. At one-week p.i., analysis of hepatic activity for each topology was derived from the individual coronal tomographic images acquired. Hollow beads were noted to exhibit maximum hepatic uptake values of 15.7% ID/g, followed by values of 6.5% ID/g for spheres, 4.1% ID/g for cages, and 2.1% ID/g for rings (scale bar, FIG. 13*a*). The value of 2.1% ID/g for rings is the lowest reported to date for such silica NPs with diameters above 10 nm. Moreover, rings did not demonstrate any appreciable splenic uptake at one-week p.i., while splenic uptake (arrows) was observed for spheres, hollow beads, and cages. While increased hepatic and splenic activities were initially noted moving from a dot size of 7.3 nm to a hollow bead size of 11 nm, these results contrasted with a relative lack of observable activities in these organs for larger-sized (i.e., ~12 nm) cages and rings.

In ex vivo biodistribution studies, each of the four topologies was evaluated at one-week p.i. of radiolabeled particles (FIG. 13*b*). Results were consistent with those found at one week on serial PET imaging (FIG. 13*a*). As particles transitioned from 7.3 nm dots to 10.8 nm hollow beads, approximately 5-fold and 3-fold increases in hepatic and splenic uptake were observed, respectively (FIG. 13*b*). Intriguingly, at even larger particle sizes, substantial decreases in hepatic and splenic activity were noted for both 12.3 nm cages and 12.1 nm rings. Specifically, relative to hollow beads, cages exhibited approximately 3-fold and 1.7-fold drops in hepatic and renal activity, respectively, while rings exhibited even larger fold changes of 5.5 and 9 for these activities, respectively (FIG. 13*b*). Results were statistically significant across all topologies ($p<0.001$), adjusting for different organs.

Metabolic cage studies performed on the four topologies (FIG. 13*c*) showed at one-week p.i that 7.3 nm dots were associated with the lowest urinary and total clearances (i.e., ~13 and 38% ID, respectively), while rings exhibited the highest (i.e., ~38 and 64% ID, respectively). Results were statistically significant ($p<0.0001$) across the four topologies. Time-dependent clearance studies (FIG. 13*d*) provided a more differentiated picture. Cumulative (total) clearances (% ID) increased from 6 to 168 hours, but were surprisingly delayed for both cage and ring samples. In particular, for cages, total urinary and fecal clearance did not substantially increase until about day 5 p.i., noting a 13-fold increase relative to early time points (i.e., 6 hours). Statistical significance was established among topologies for total urinary clearance ($p<0.0001$) and rates of accumulation ($p=0.0001$). At later times p.i., relative contributions of both urinary and fecal excretion became fairly equivalent for both cages and spheres (FIG. 13*d*). Urinary excretion for both rings and beads looked fairly equivalent at later time points.

Spheres, hollow beads, cages, and rings have very different topologies, i.e., there are no simple continuous deformations that can transform these geometrical objects into each other without tearing holes (i.e., they are not homeomorphic). In nature, protein structures with ring or cage topologies are ubiquitous and play crucial roles, e.g., in cellular function. For the first time, a set of inorganic nanoobjects were synthesized with these varying topologies, but otherwise similar shapes and surface chemical properties, as well as sizes around 10 nm (see FIG. 15), in order to study the effects of topology on biological response. While increases in the diameter of spherical silica NPs led to significant, but expected, increases in RES uptake and decreases in cumulative urinary clearance, the opposite trend was observed for the largest diameter objects, in particular for rings (also see FIG. 19). It is proposed that topology dependent properties, i.e., deformability in case of urinary excretion and diffusivity in case of RES uptake, can rationalize these surprising observations.

Figure 14:
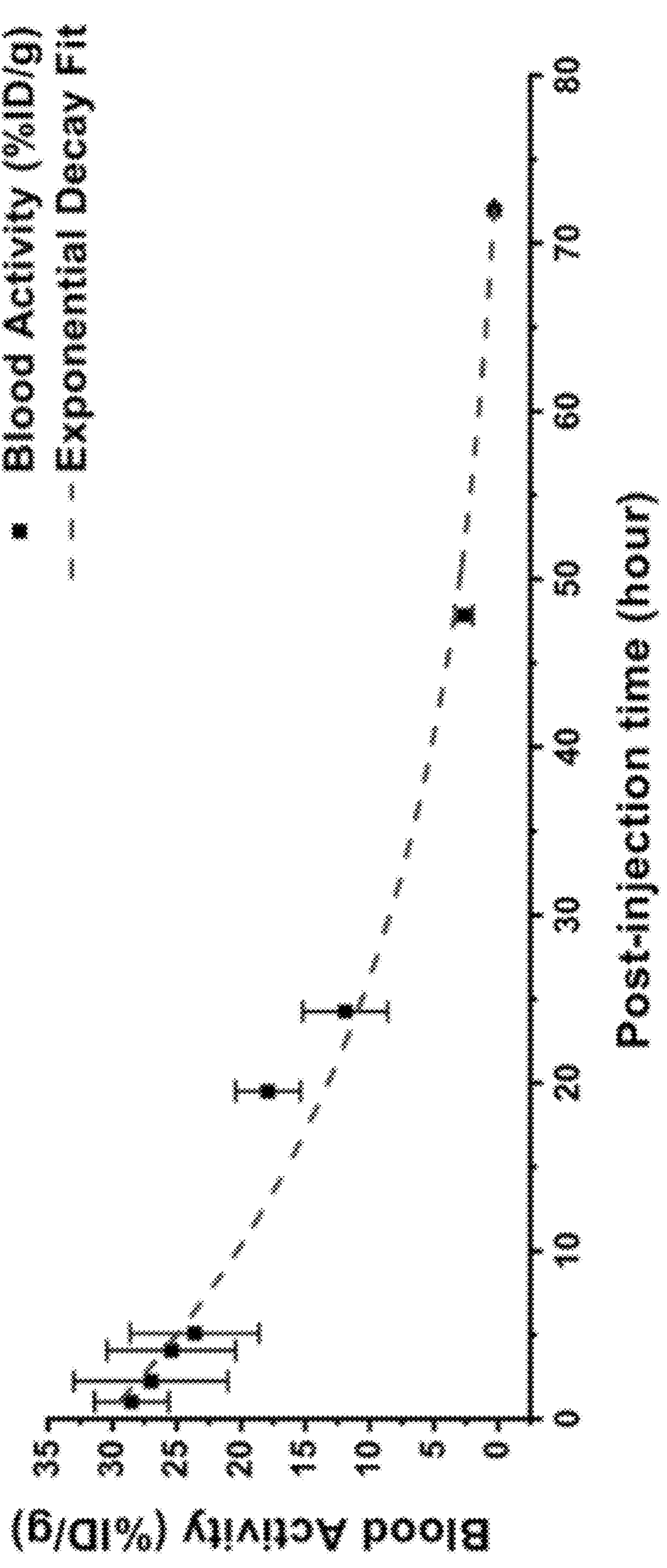
FIG. 14 shows biodistribution studies of 12.1 nm sized (TEM) rings and liver uptake analysis for all topologies studied. (a) Blood time-activity curve indicating a blood circulation half-life, $t_{1/2}$, of 17.8 hours for 12.1 nm rings (n=3). (b) Time-dependent biodistribution studies (n=3) of 12.1 nm silica rings up to one week after i.v. injection, inset is the illustration of the onset of ring deformation enabling renal clearance and low RES uptake. Error bars are calculated from the standard deviation of n=3 mice for each experiment. (c) Dependence of liver uptake one week after i.v. injection (from FIGS. 2*b* and 3*b*) on TEM diameter and (d) on diffusivity, of particles with different topologies, as indicated. Inset in (d) shows the linear relationship between liver uptake and equivalent hydrodynamic diameter (Methods), derived from the diffusion coefficients, independent of particle topology (linear fit is shown as black dashed line, $R^2=0.979$). The color code in (d) is the same as in (c).
Figure 14:
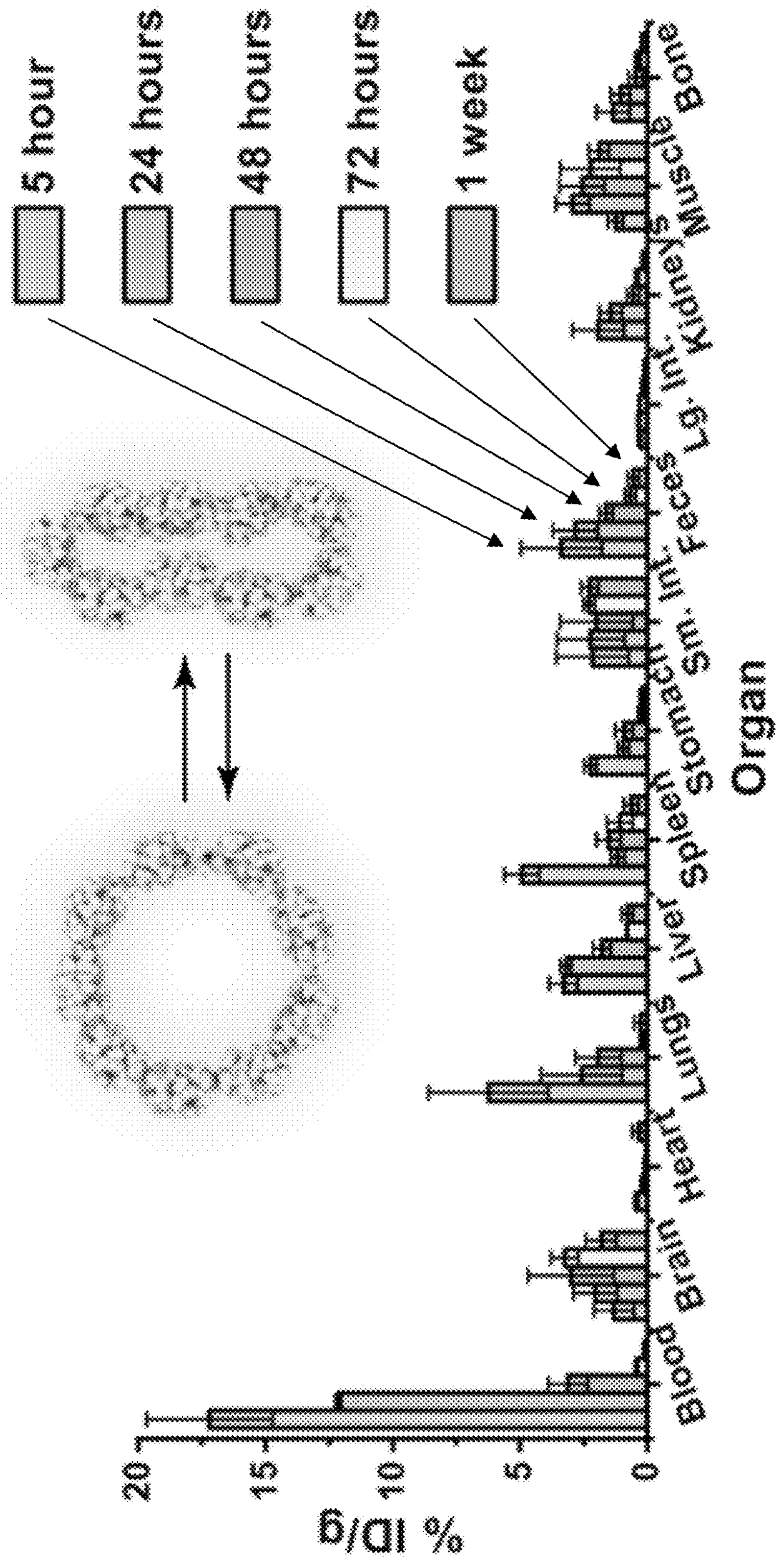
Figure 14:
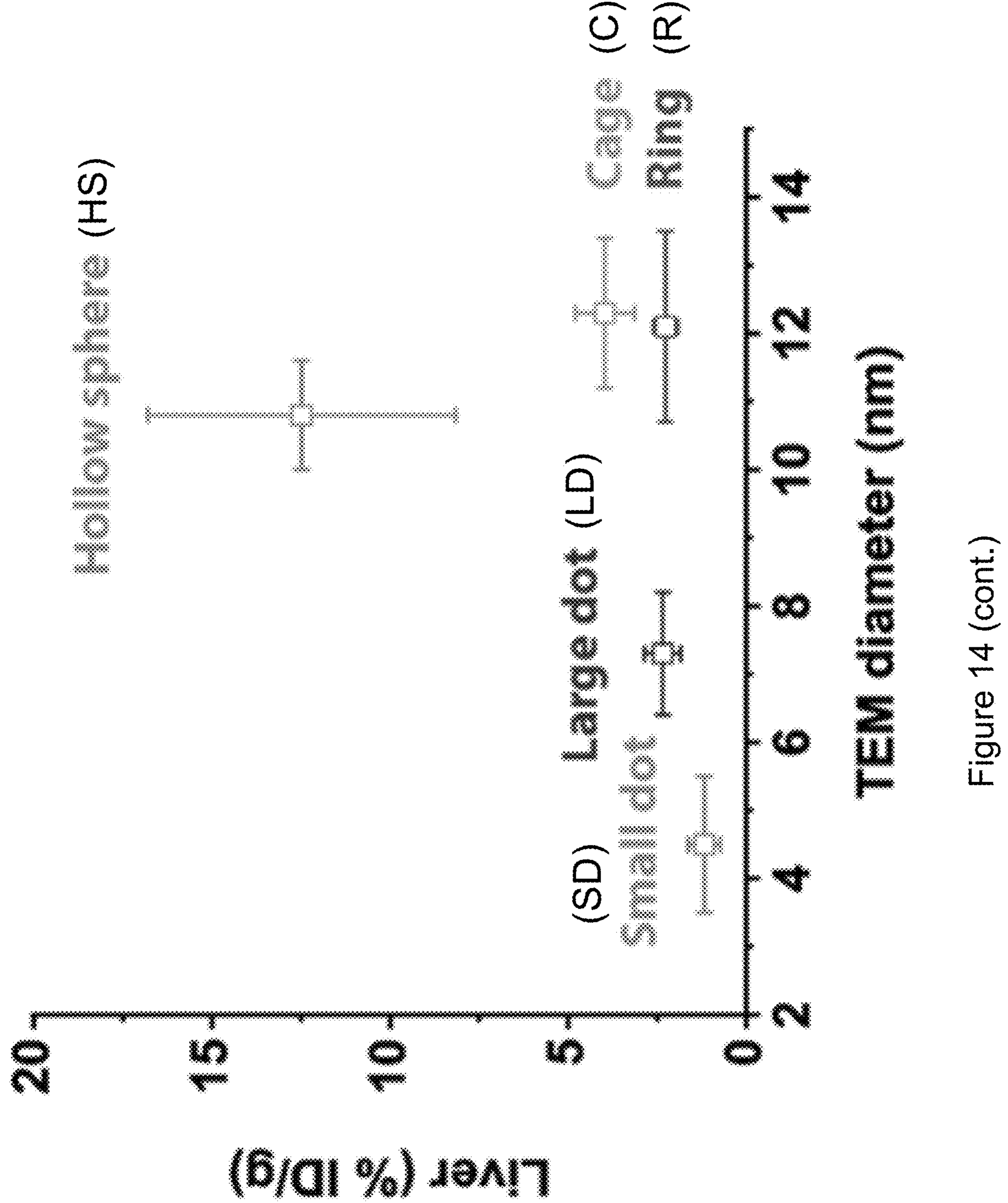
Figure 14:
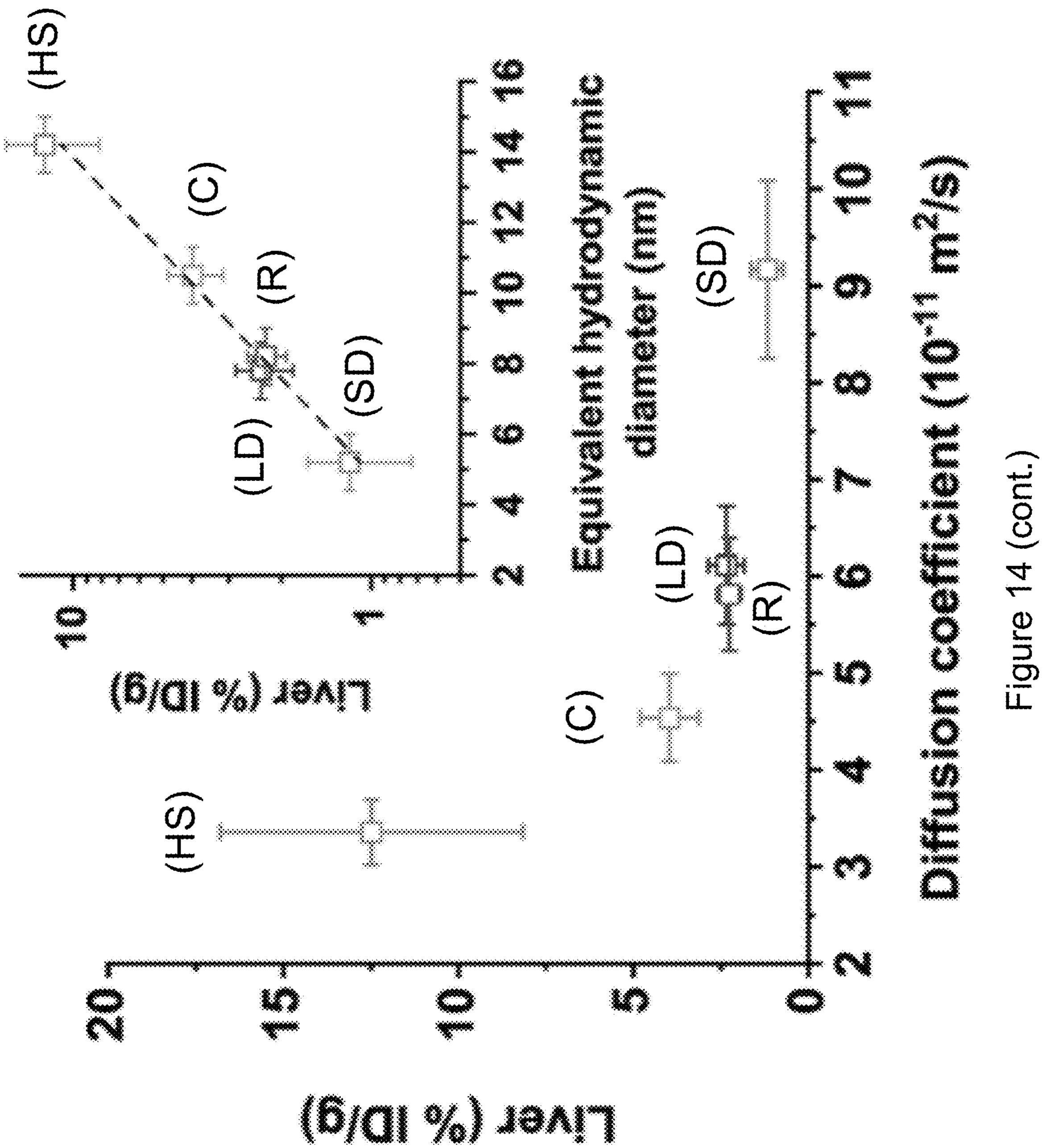

An explanation for the renal clearance of hollow beads, cages and rings with sizes well above the effective renal glomerular filtration size cut-off for inorganic NPs around 6 nm could be their degradation through, e.g., shear forces, with resulting smaller pieces clearing out. It was verified, however (FIG. 20), that these objects cleared without degradation, by collecting urine from mice at 2-hour p.i. and TEM analysis (Methods) for cage and ring topologies (expected to be particularly prone to this mechanism). Such amorphous silica NPs can deform as a result of their structural elements, i.e. ~2 nm diameter primary silica clusters, connected via thin bridges into shells of hollow beads, struts and vertices of cages, and the backbone of rings. At small length scales, even crystalline materials are flexible. Despite their size, indeed model calculations suggest (Methods, FIG. 21) that they can undergo glomerular filtration in the kidneys by being "squeezed" by the glomerular capillary pressure (FIG. 14*b*, inset). Deformations are facilitated by a "pearl-chain" type structure, where bending is localized to the thin and compliant bridges connecting the silica clusters. Fully squeezing rings together, the combined diameter of the two silica struts next to each other, is ~4 nm, i.e. below the cut-off for renal clearance.

Figure 13:
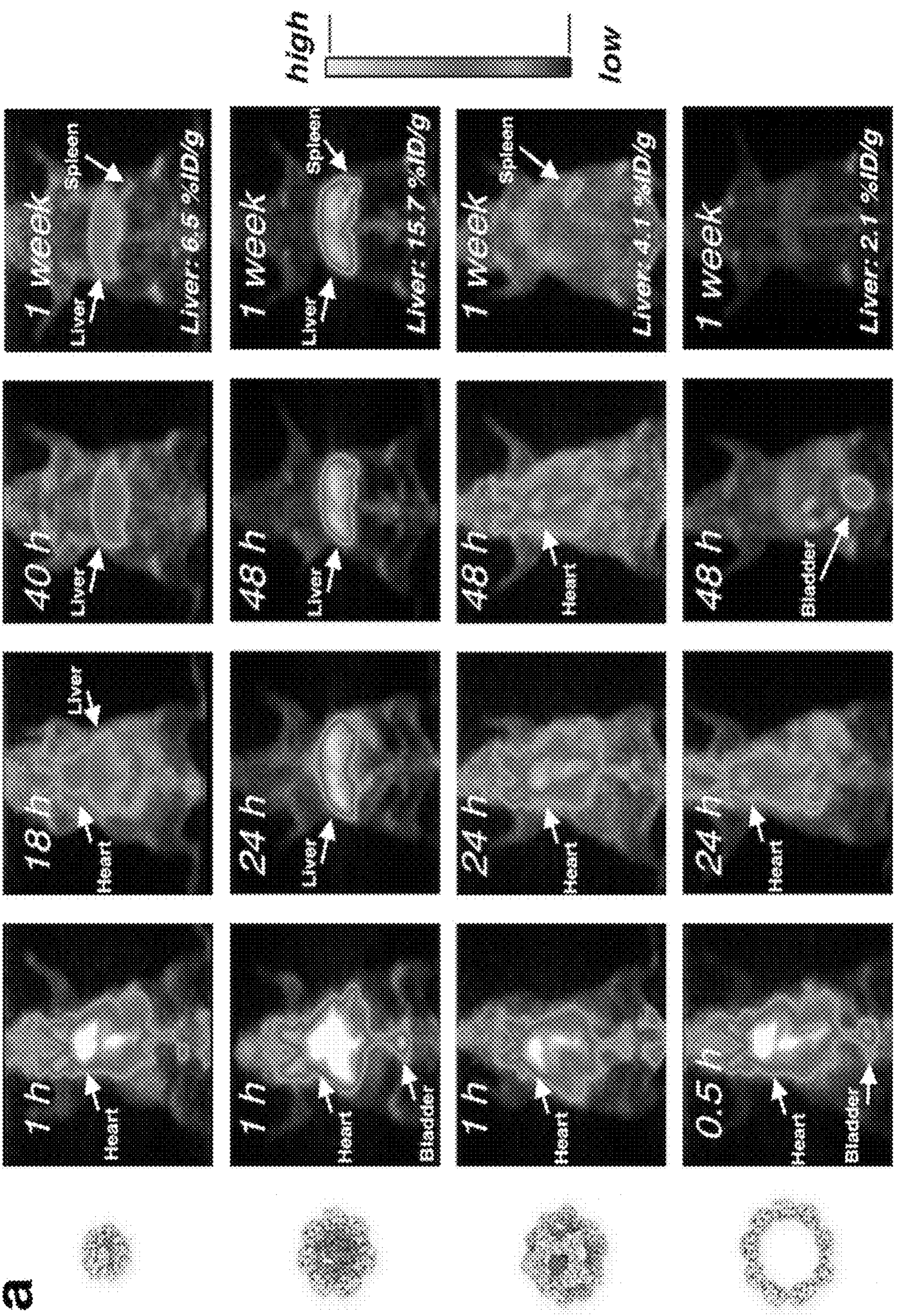
FIG. 13 shows in-vivo and ex-vivo murine studies of inorganic NPs with four different topologies. (a) MIP images of NPs with silica core diameters, as determined by TEM, of 7.3 nm (spheres), 10.8 nm (hollow beads), 12.3 nm (cages), and 12.1 nm (rings) at 1, ~24, ~48 hours, and one-week time points after i.v. injection showing liver uptake of 6.5, 15.7, 4.1, and 2.1% ID/g, respectively, at the final one-week time point (n=1 mouse/topology). (b) Biodistribution for spherical (orange), hollow bead (green), cage (purple), and ring (yellow) particles at one-week time point after i.v. injection (n=3 mice/topology, $p<0.001$). (c) Metabolic cage studies performed on mice for each of the four different inorganic NPs (n=3 mice/topology) showing urinary (yellow) and fecal (brown) clearance along with the remaining activity in the carcass (grey) at the one-week time point after i.v. injection ($p<0.0001$). (d) Time-dependent renal/hepatic clearance levels measured over a 6 to 168 hour p.i. time period (7 days) for the four topologies studied (cumulative urinary clearance $p<0.0001$, rate of accumulation $p=0.0001$). Error bars are calculated from the standard deviation of n=3 mice for each experiment.
Figure 13:
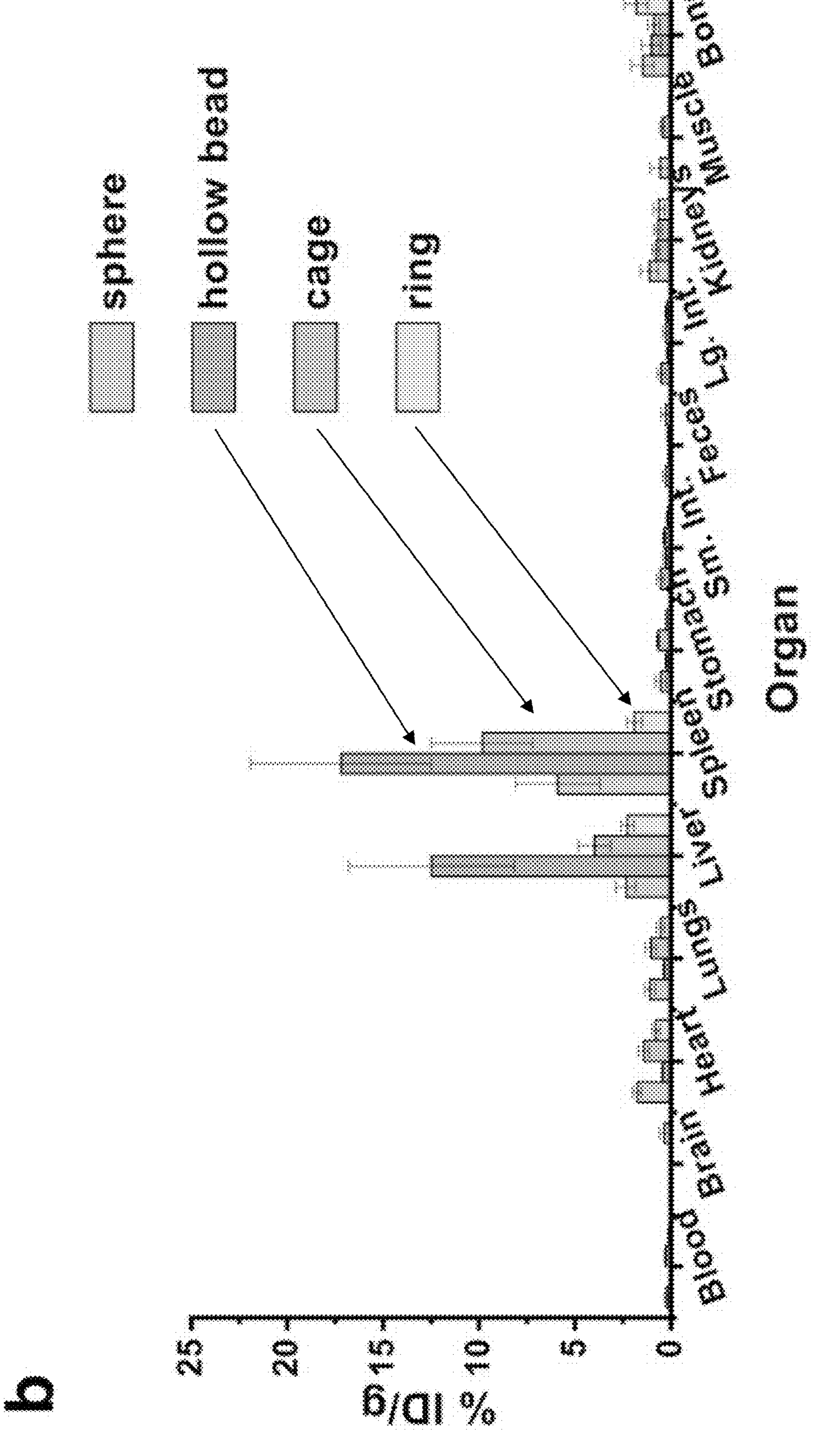
Figure 13:
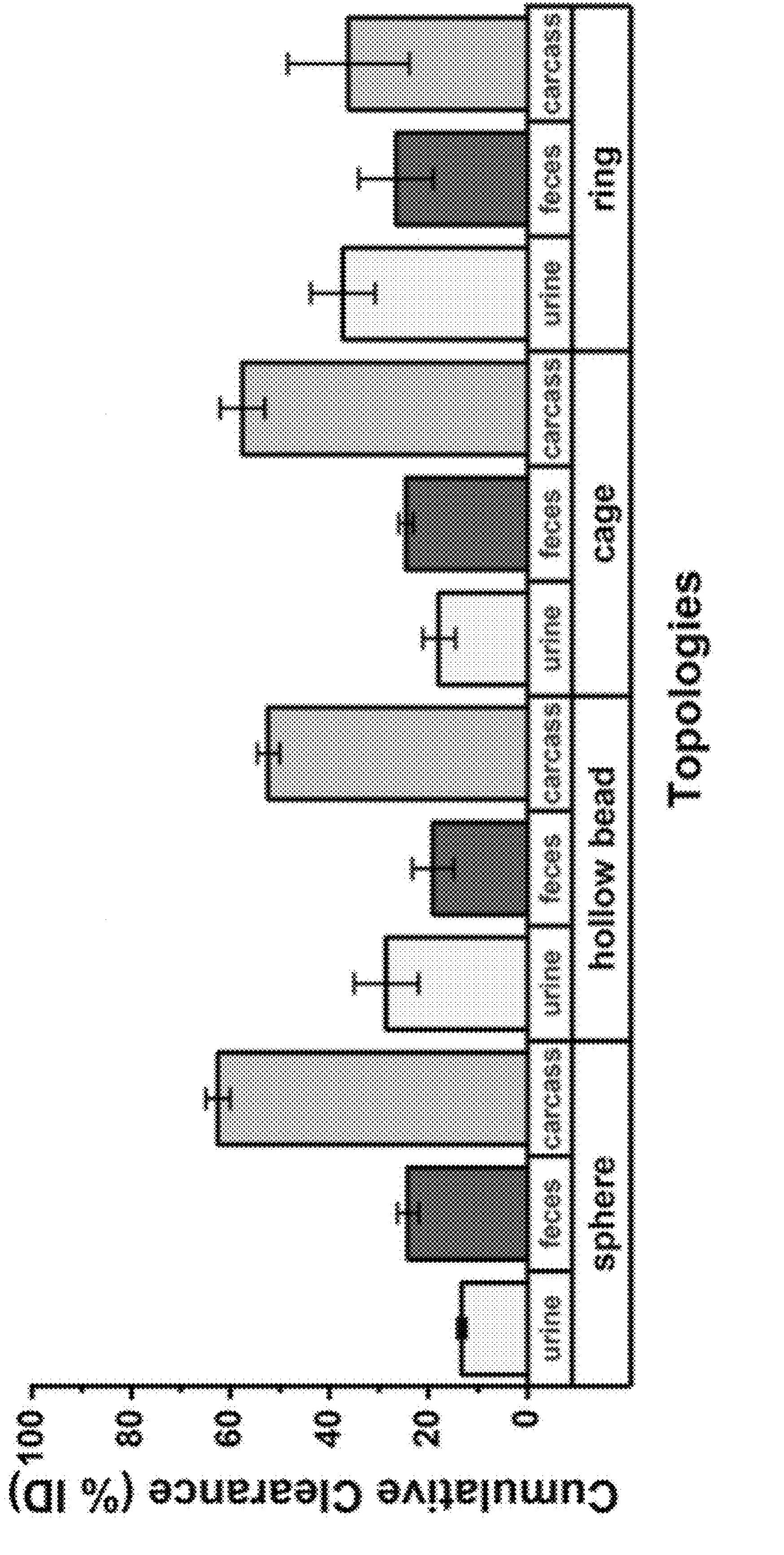
Figure 13:
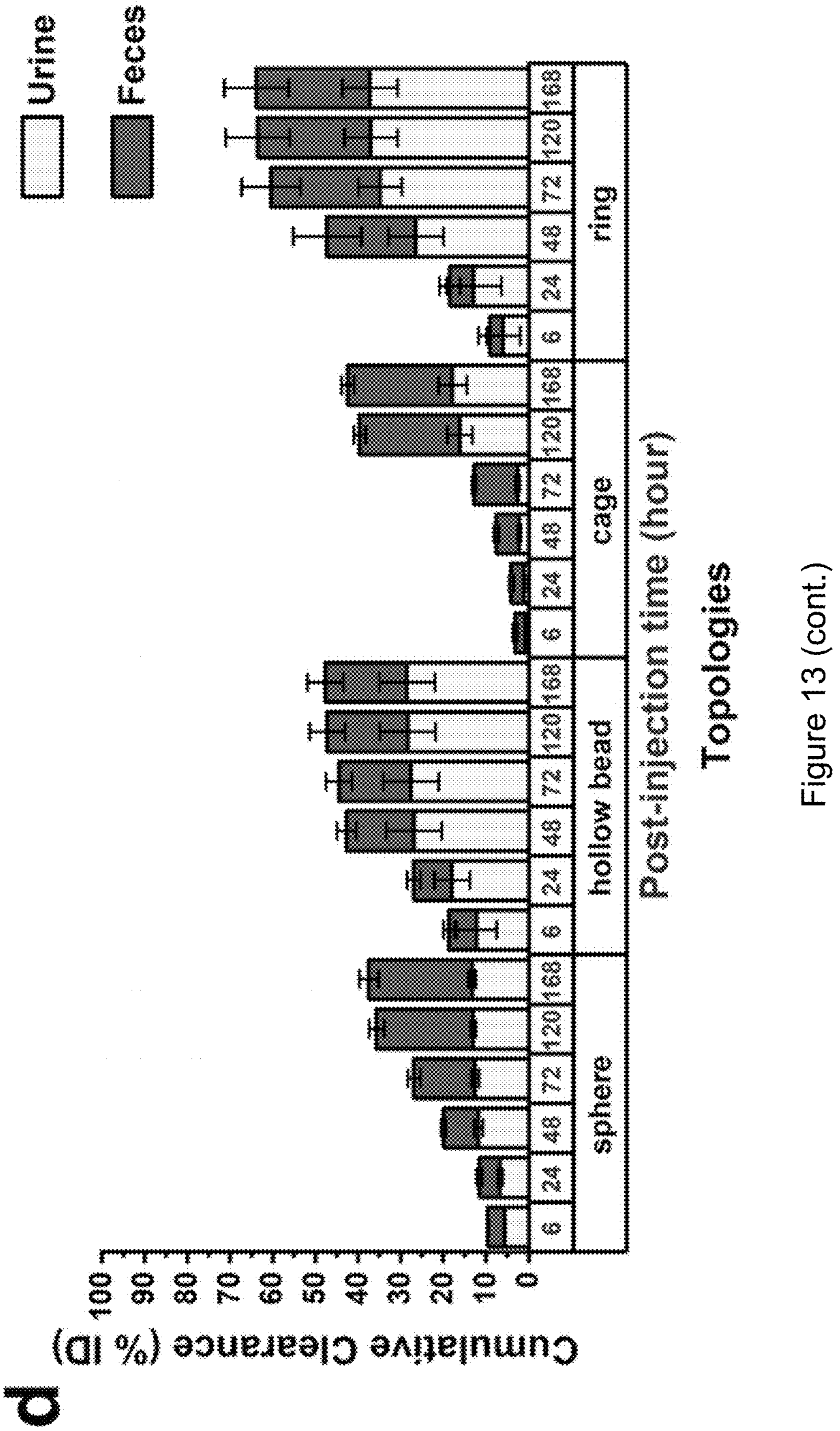

The concept of topology dependent inorganic NP deformation is further supported by the ring blood circulation half-life, $t_{1/2}$=17.8 h (h=hour(s)) (FIG. 14*a*), which is longer than that of smaller dots, 15.3 h for 6.5 nm dots, with similarly low liver uptake (<5% ID/g). Rings undergo glomerular filtration when they get squeezed, which takes longer. Rings also show higher clearance via feces as compared to smaller (5.2 nm) dots, 27% vs 14% (FIGS. 12*c*-13*c*), respectively. As hepatic clearance takes longer than renal clearance, this is consistent with the increased blood circulation half-life of rings. For example, a blood activity of 12% ID/g for rings at 24-hour p.i. (FIG. 14*a*) was measured, much higher than that of the dots (highest blood-activity of 6% ID/g at 24-hour p.i.). Results of time-dependent biodistribution studies performed for rings reveal no significant uptake by RES organs, even at early time points (FIG. 14*b*). Blood activity decreases significantly at 48-hour p.i., consistent with significant renal and hepatic clearance for this time-point in time-dependent metabolic cage studies (FIG. 13*d*).

Figure 22:
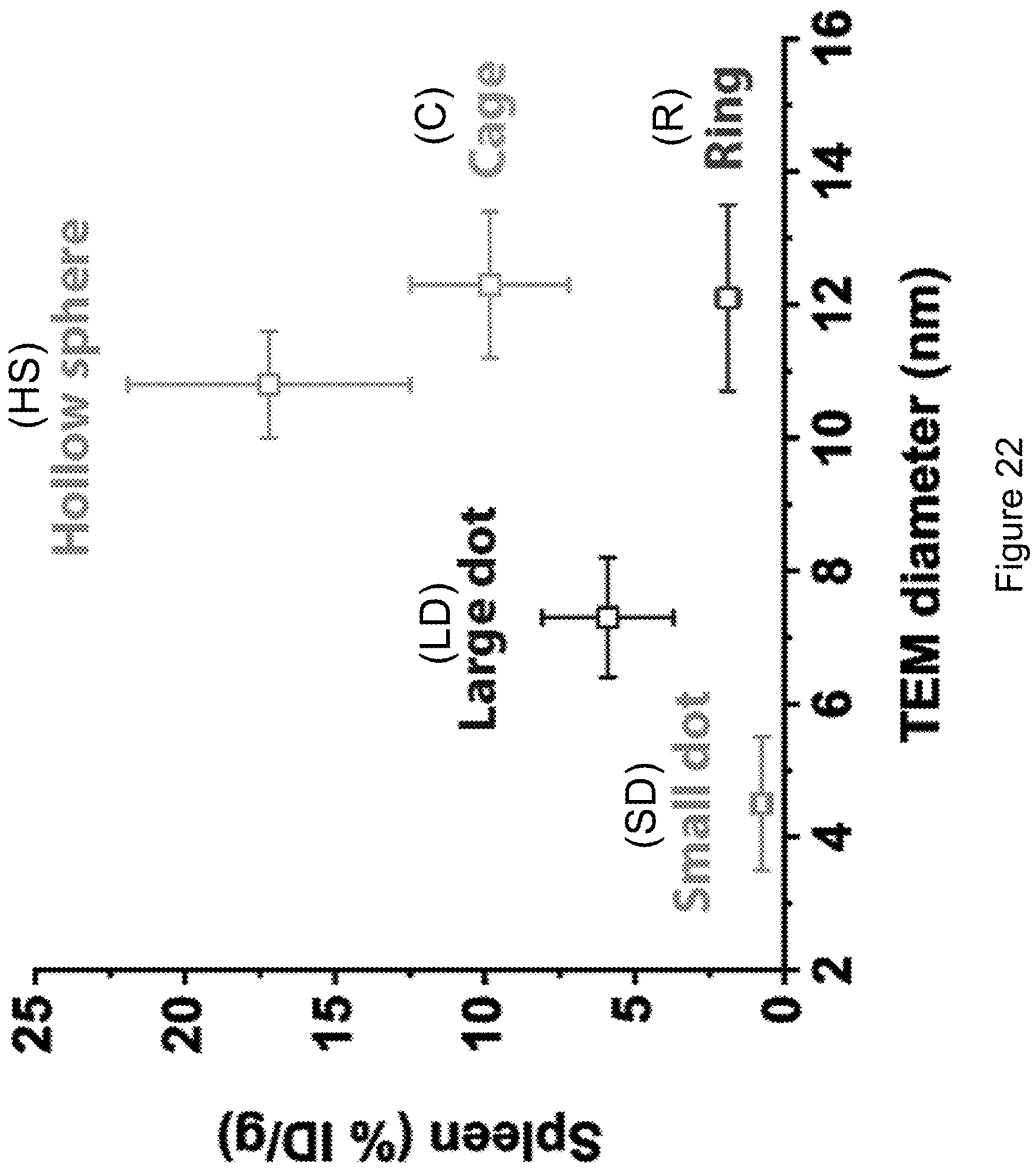
FIG. 22 shows dependence of spleen uptake on physical particle size and particle diffusivity. (a) Dependence of spleen uptake one week after i.v. injection (from FIGS. 2*b* and 3*b*) on TEM diameter and (b) on diffusivity, of particles with different topologies, as indicated in (a). Inset in (b) shows the linear relationship between spleen uptake and equivalent hydrodynamic diameter (Methods), derived from the diffusion coefficients, independent of particle topology (linear fit is shown as black dashed line, R2=0.849). The color code in (b) is the same as in (a).
Figure 22:
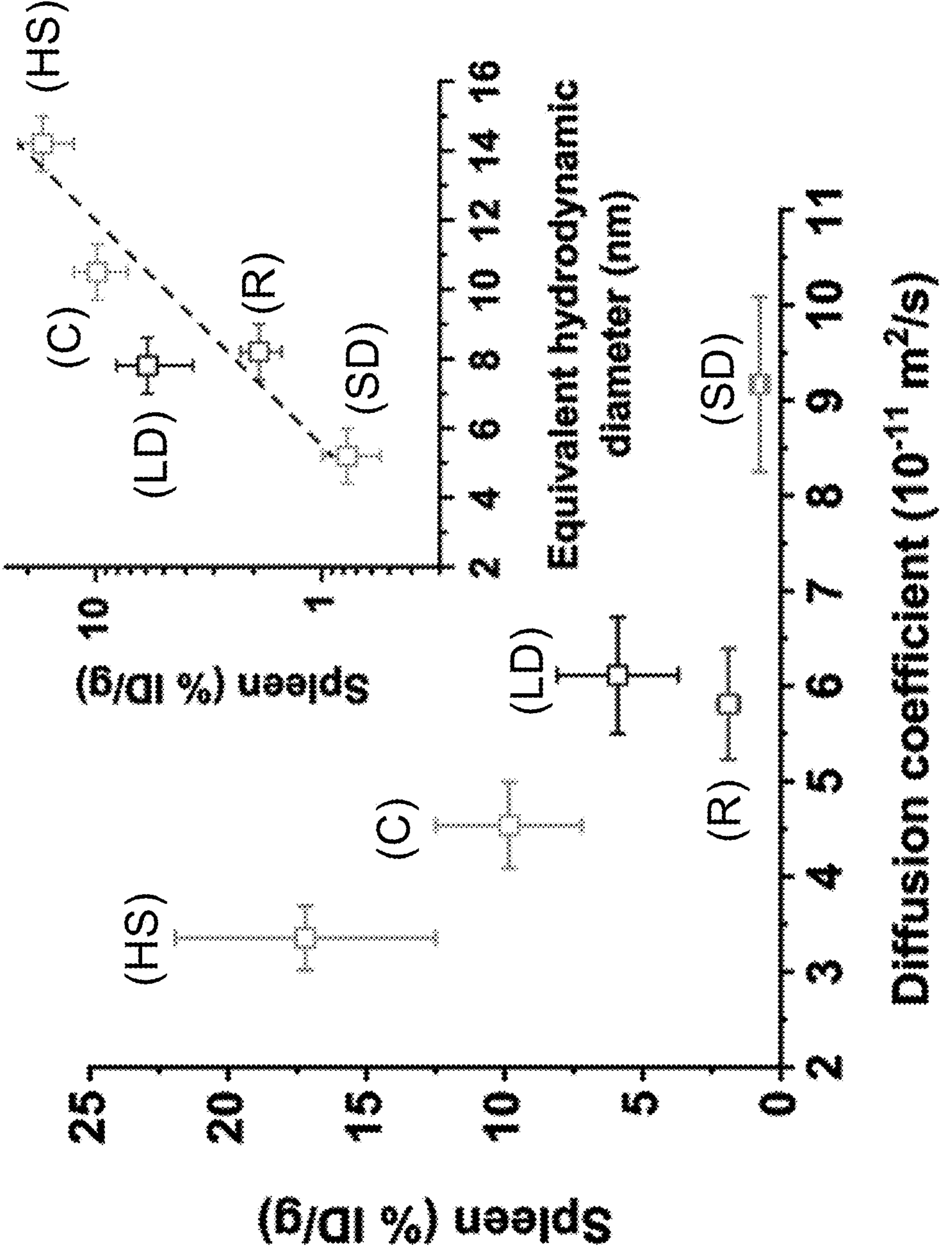
Figure 23:
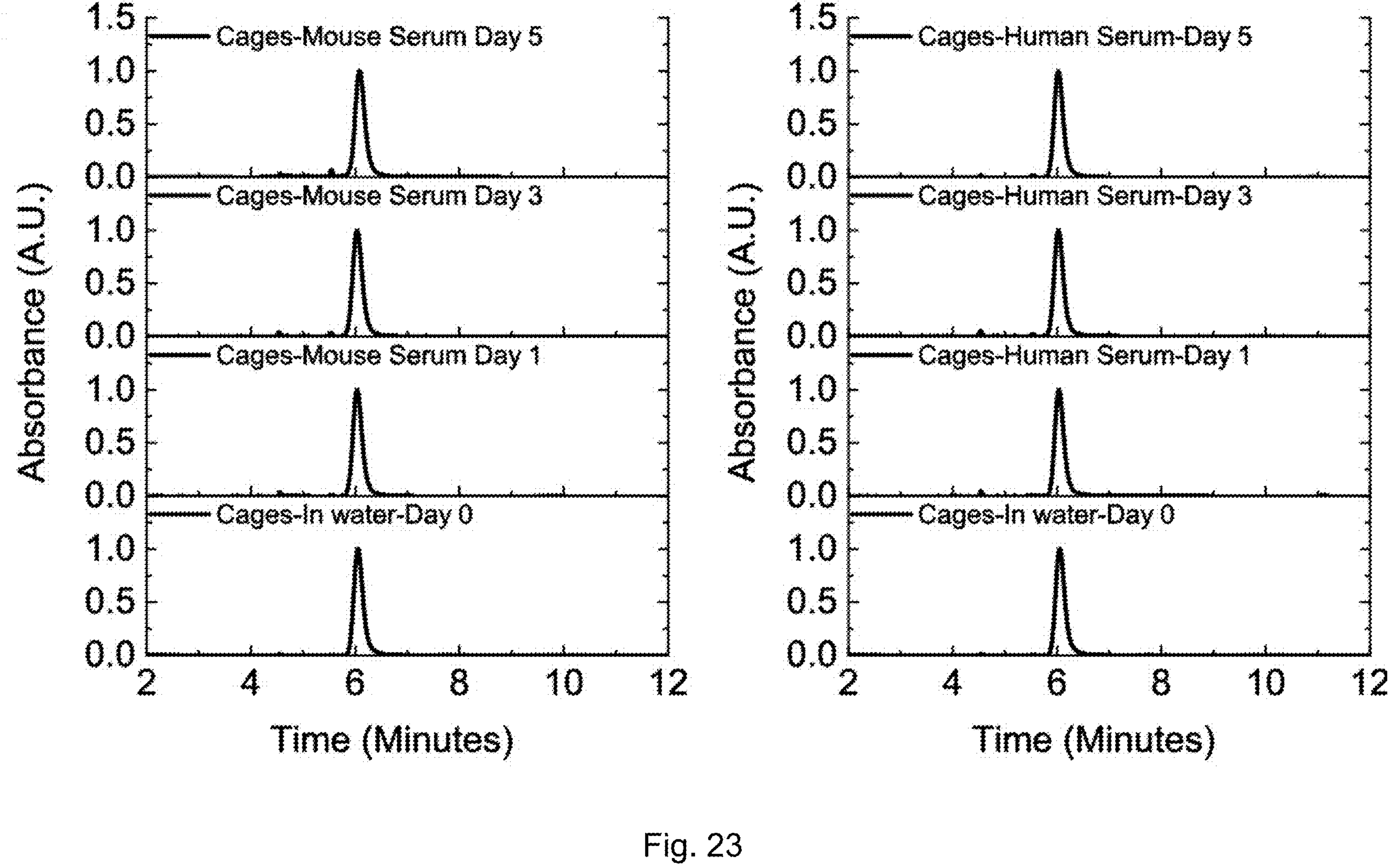
FIG. 23 shows HPLC stability study of cages and rings in mouse and human serum. HPLC chromatograms of rings (a) and cages (b) after incubation in mouse (left panel) and human (right panel) serum for up to 5 days. Peak shapes and positions in HPLC elugrams remained unchanged, indicating the high stability of both topologies in serum and corroborating the notion that the elevated sizes measured for these topologies in FCS may result from smaller serum proteins hovering on the inside of these particles rather than from their physical adsorption. Experiments were performed on materials after storage in a refrigerator at 4° C. for about a year.
Figure 23:
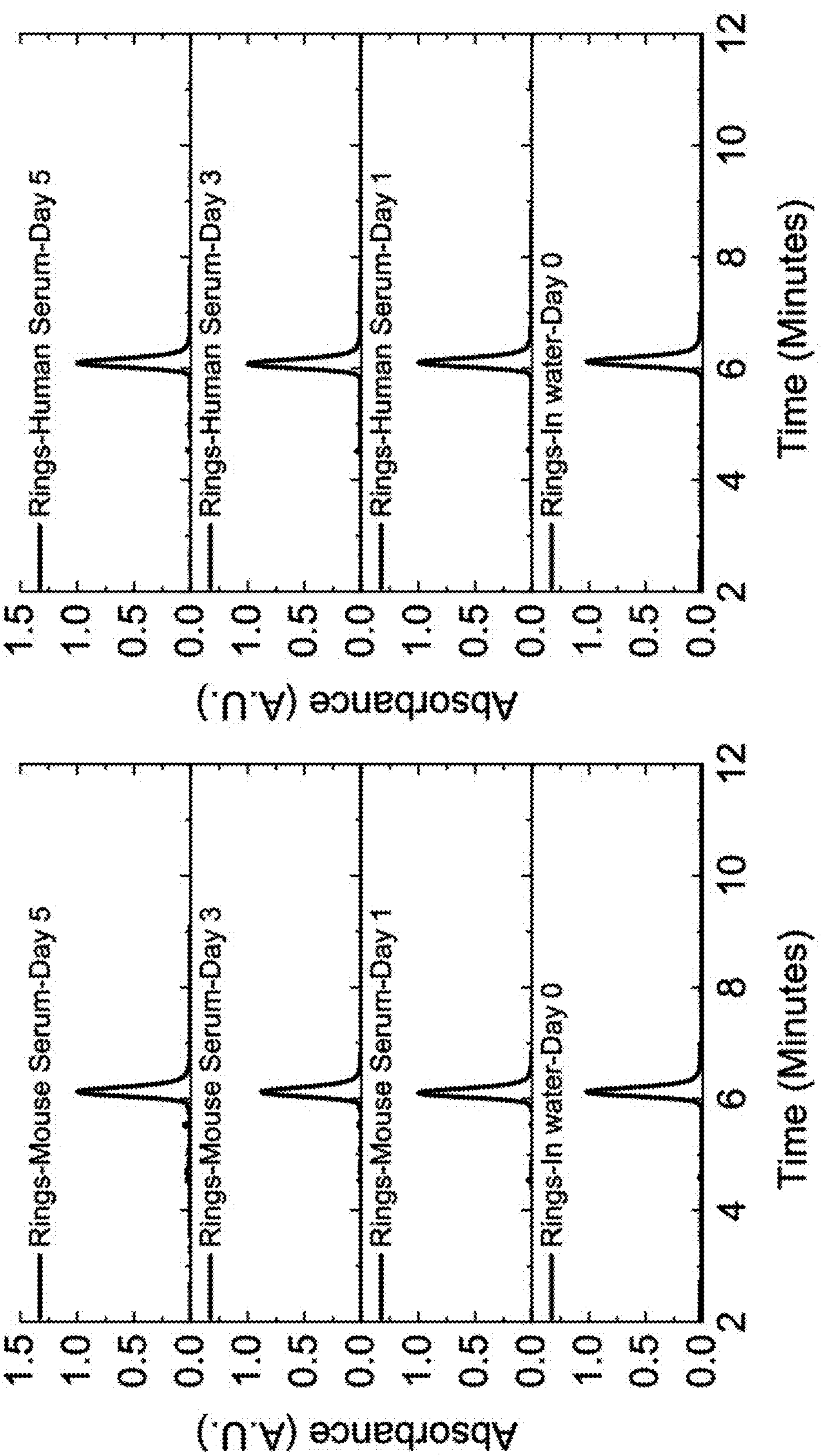

While no systematic dependence of liver (or spleen) uptake was found at one-week p.i. on physical particle size, uptake strongly correlated with FCS measured diffusion coefficients and (equivalent) hydrodynamic sizes derived therefrom (FIGS. 14*c*, 14*d*; FIG. 22). Diffusivity of spherical particles decreases with diameter, which is correlated with higher RES uptake (compare small and large dots with hollow spheres). Holes in nanoobjects change standard size-diffusivity relations. Silica cages have very similar shape, but larger (TEM) sizes than hollow spheres. Multiple holes in their surface lead to faster diffusion, however, which correlates with substantially lower liver (and spleen) uptake. Rings, while amongst the largest (TEM) diameter objects tested, because of their large hole and flat shape, have comparatively high diffusivity, correlating to low RES uptake. Extensive stability tests (Methods) in salt and protein solutions showed that particle aggregation or protein adsorption is minimal and cannot account for our observations (Tables 1 & 2, FIG. 23). The uptake-diffusivity correlation is not consistent with earlier models predicting higher particle sequestration probability in the liver with increasing diffusivity. Such simple models, in which diffusion competes with flow to transport particles to the liver sinusoid walls, while physically intuitive do not explicitly relate higher diffusivity to reduced particle residence time on wall surfaces, likely lowering cellular uptake by Kupffer and other cells.

TABLE 1

Stability of particles with different topologies in salt solution over 7 days as measured by changes in hydrodynamic size via FCS.

| Excitation Wavelength | Particle Type | Original Size (nm) | Size on Day 0 (nm) | Size on Day 7 (nm) |
|---|---|---|---|---|
| 445 nm | DEAC-Ring | 8.3 ± 0.2 | 7.6 ± 0.1 | 7.6 ± 0.1 |
| | DEAC-Cage | 11.3 ± 0.4 | 11.5 ± 0.5 | 10.9 ± 0.2 |
| | DEAC-Hollow | 14.2 ± .05 | 16.3 ± 1.3 | 14.9 ± 2.5 |
| 647 nm | Cy5-C'dot | 5.2 ± 0.1 | 5.2 ± 0.1 | 5.3 ± 0.2 |

Entries in column "Original Size" are from FCS measurements right after synthesis, while entries in columns "Size on Day 0" and "Size on Day 7" refer to FCS measurements on the identical materials after storage in a refrigerator at 4° C. for about a year. Within the error bars, particles sizes for different topologies are essentially unchanged, both between original and one year old particles, as well as on days 0 and 7 of the salt solution treatment, confirming the high stability of the materials.

TABLE 2

Protein adsorption tests in mouse serum over 7 days for particles with different topologies as measured by FCS particle size.

| Excitation Wavelength | Particle Type | Original Size (nm) | Day 0 (nm) | Day 1 (nm) | Day 3 (nm) | Day 7 (nm) |
|---|---|---|---|---|---|---|
| 445 nm | DEAC-Ring | 8.3 ± 0.2 | 7.6 ± 0.1 | 8.8 ± 1.5 | 9.2 ± 1.2 | 10.9 ± 1.9 |
| | DEAC-Cage | 11.3 ± 0.4 | 11.5 ± 0.5 | 13.1 ± .06 | 12.3 ± 0.3 | 14.6 ± 0.5 |
| | DEAC-Hollow | 14.2 ± 0.5 | 16.3 ± 1.3 | 14.4 ± 1.2 | 14.7 ± 0.5 | 14.8 ± 1.8 |
| 647 nm | Cy5-C'dot | 5.2 ± 0.1 | 5.2 ± 0.1 | 5.0 ± 0.1 | 5.3 ± 0.1 | 5.4 ± 0.1 |

Similar to Table 1, entries in column "Original Size" are from FCS measurements right after synthesis, while entries in subsequent columns "Day 0" to "Day 7" refer to FCS measurements on the identical materials after storage in a refrigerator at 4° C. for about a year. Please note that elevated diameters exclusively for rings and cages may reflect smaller serum proteins hovering on the inside of these particles thereby lowering their diffusivity rather than their physical adsorption, consistent with subsequent HPLC-based stability tests on these materials to verify this hypothesis (see FIG. 23).

Figure 19:
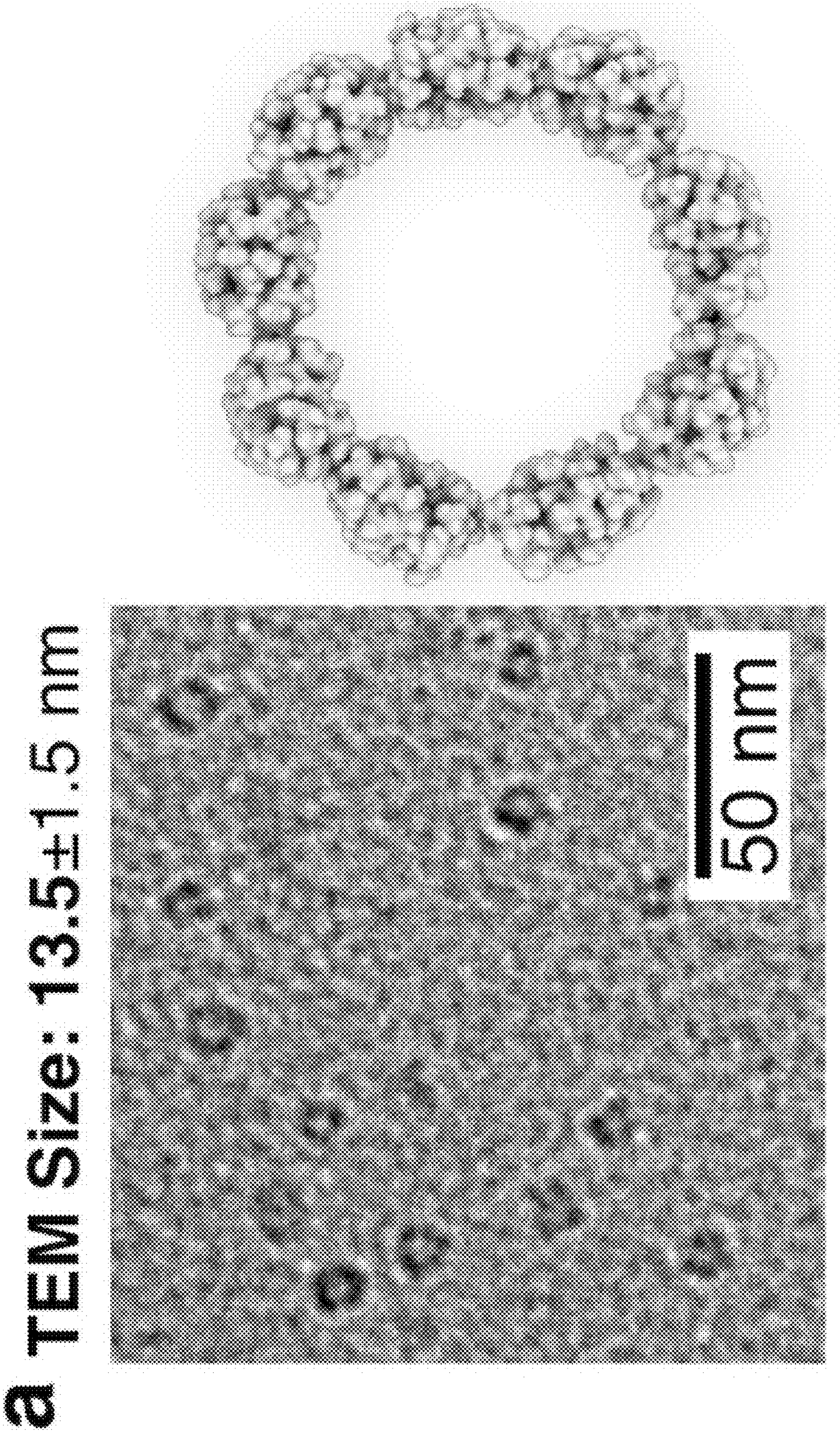
FIG. 19 shows in-vivo and ex-vivo studies with 13.5 nm diameter silica rings. (a) TEM image (left) and illustration (right) of silica nanorings with 13.5±1.5 nm average TEM diameter (from 150 particles). (b) Biodistribution study (n=1) for the same rings as in (a) at one-week time point after i.v. injection. (c) MIP images of the same rings as in (a) at 0.5, 24, 48, 72 hours, and one-week time points after i.v. injection showing 2.6% ID/g liver uptake at the final time point of one week.
Figure 19:
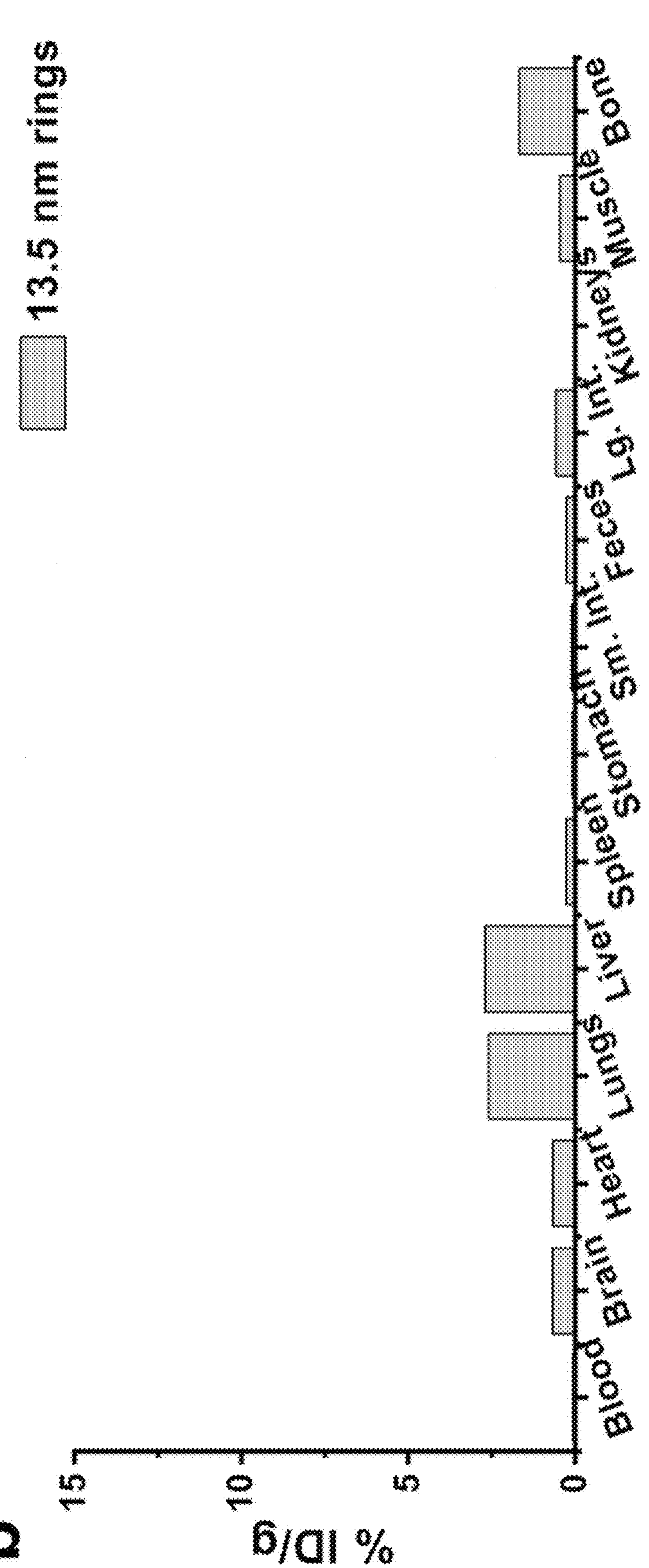
Figure 19:
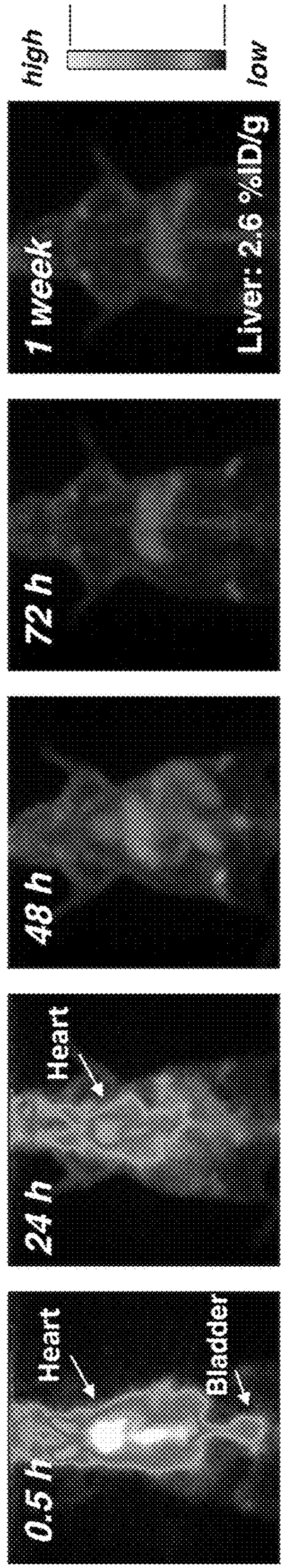

The largest rings tested in mice had a diameter (TEM) of 13.5 nm (FIG. 19). A ~1 nm thick PEG layer brings their size above 15 nm. They still showed favorable biodistribution with liver uptake at one-week p.i. of only 2.6% ID/g. The 5.2 nm (FCS) dots with roughly 3-4 nm silica core diameter with similarly low liver uptake (i.e., 1.8% ID/g, FIG. 12*a*) have an estimated outer surface area of ~40 $nm^2$. The large rings with a roughly 2 nm thick silica torus have a theoretical outer silica surface area of ~230 $nm^2$, which increases to ~440 $nm^2$ for a 12 nm cage, suggesting substantially improved loading capacities. Relative to ultrasmall spherical NPs, the combination of renal clearance, higher loading capacity, lower RES uptake, higher blood circulation times, and the ability to effectively "hide", e.g., hydrophobic molecules on their inside, makes cage and ring topologies expected subjects for advanced applications in nanomedicine. Most notably, they allow inorganic nanomaterial designs to escape the ultrasmall NP size regime, i.e., the stringent limitations imposed by size requirements below 6 nm, in order to observe effective renal clearance and yield favorable biodistribution profiles.

Methods. Chemicals and Materials. All materials were used as received. The succinimidyl ester of 7-diethylaminocoumarin-3-carboxylic acid (DEAC) was purchased from Anaspec. Cyanine5.0 maleimide (Cy5) was purchased from GE Healthcare. Hexadecyltrimethyl ammonium bromide (CTAB, ≥99%), tetramethyl orthosilicate (TMOS, ≥99%), 2.0 M ammonium hydroxide in ethanol, (3-aminopropyl) trimethoxysilane (APTMS, 97%), Hank's Balanced Salt Solution (HBBS) and anhydrous dimethyl sulfoxide (DMSO, ≥99%) were purchased from Sigma, Aldrich. (3-Aminopropyl) trimethoxysilane (APTES), 2-[methoxy (polyethyleneoxy)6-9 propyl] trimethoxysilane (PEG-Silane, 6-9 ethylene glycol units, PEG-silane (6EO)), (3-mercaptopropyl) trimethoxysilane (MPTMS, 95%), and methoxy triethyleneoxy propyl trimethoxysilane (PEG-silane, 3 ethylene glycol units, PEG-silane (3EO)) were obtained from Gelest. 1,3,5-trimethylbenzene (mesitylene/TMB, 99% extra pure) was purchased from Acros Organics. Deferoxamine-Bn-NCS-p (DFO-NCS, 94%) was purchased from Macrocyclics. Absolute anhydrous ethanol (200 proof) was purchased from Koptec. Glacial acetic acid was purchased from Macron Fine Chemicals. 5.0 M sodium chloride irrigation USP solution was purchased from Santa Cruz Biotechnology. Syringe filters (0.22 μm, PVDF membrane) were purchased from MilliporeSigma. Vivaspin sample concentrators (MWCO 30K) and Superdex 200 prep grade were obtained from GE Health Care. Snakeskin dialysis membranes (MWCO 10K) were purchased from Life Technologies. Deionized (DI) water was generated using Millipore Milli-Q system (18.2 MΩ·cm). Glass bottom microwell dishes for FCS were obtained from MatTek Corporation. Carbon film coated copper grids for TEM were purchased from Electron Microscopy Sciences. Xbridge Peptide BEH C18 Column (300 Å, 5 μm, 4.6 mm×50 mm, 10K-500K) was purchased from Waters Technologies Corporation. Human serum and mouse serum were purchased from BioIVT. UHPLC grade acetonitrile was purchased from BDH.

Synthesis of Silica Nanoparticles with Spherical Shape. Fluorescent core-shell silica nanoparticles with spherical shape were synthesized in aqueous solution as described previously. Briefly, Cy5 maleimide was conjugated to MPTMS via thiol-maleimide click-chemistry (1:23 ratio) a day prior to synthesis in a glove box. On the first day of particle synthesis for a 10 mL reaction batch, 68 μL TMOS and 0.367 μmol Cy5 dye-conjugate were added dropwise into 0.002 M ammonium hydroxide solution under stirring at 600 r.p.m. at room temperature resulting in the smallest (~5 nm diameter) nanoparticles. For larger particle sizes, synthesis temperature was increased up to 80° C. as described previously. The following day, 100 μL PEG-silane (6EO) was added into the reaction solution, which was left stirring overnight at room temperature. The next day, in order to achieve full covalent attachment of PEG-silane molecules onto the silica core surface, the reaction solution was heated at 80° C. overnight without stirring. The solution was then cooled down to room temperature, and 2 μL APTMS was added at 600 r.p.m., while stirring at room temperature enabling post-PEGylation surface modification by insertion (PPSMI). The following day, 0.42 mmol of DFO-NCS chelator was added to the solution to react with primary amines on the silica surface via amine-NCS conjugation.

Synthesis of Inorganic Nanoparticles with Ring, Cage and Hollow Bead Topologies. Fluorescent silica cages and rings were synthesized in aqueous solution via micelle templating as described previously, whereas the synthesis of hollow beads, described herein, has not been reported. Briefly, succinimidyl ester derivative of DEAC dye was conjugated with APTES via amine-ester conjugation-chemistry (1:25 ratio) a day prior to synthesis in a glove box. On the first day of particle synthesis for a 10 mL reaction batch, CTAB (125 mg for cages, 50 mg for hollow beads, and 83 mg for rings) was dissolved into 10 mL of 0.002 M ammonium hydroxide solution under stirring at 600 r.p.m. at 30° C. for 1 hour before the addition of 100 μL TMB to swell the micelles, which was followed by stirring for another hour. TMOS (100 μL for cages, 800 μL for hollow beads, and 68 μL for rings) and 0.2 μmol DEAC-dye conjugate were then added dropwise to the reactions, except for hollow beads, which required a post-PEGylation fluorescent dye functionalization on the particle surface due to the high concentration of silica precursor used in the bead synthesis causing aggregation and making it hard to successfully functionalize the hollow beads with fluorescent dyes using ester chemistry. The following day, 6EO PEG-silane (150 μL for cages, 1200 μL for hollow beads, and 100 μL for rings) was added into the reaction solutions, which were left stirring overnight at 30° C. The next day, in order to achieve full covalent attachment of PEG-silane molecules onto the silica surface, the solutions were heated at 80° C. overnight without stirring. The reaction solutions were then cooled down to room temperature. The hollow bead particle sample, specifically at this step, was centrifuged at 4300 r.p.m. three times to remove larger aggregates. Subsequently, samples were syringe-filtered (MWCO 0.2 μm, PTFE), and transferred into a dialysis membrane (MWCO 10K). The samples were dialyzed in 200 mL of ethanol/deionized water/glacial acetic acid solution (500:500:7 volume ratio), and the acid solution was changed once a day for three days to remove CTAB micelles from the inner pores of the silica NPs, as well as to remove unreacted reagents. Following acid dialysis, the samples were transferred into 5 L deionized water, and the deionized water was refreshed once a day for three days to remove ethanol and acetic acid solvents.

Following these dialysis treatments, the reaction batches were transferred back into a round-bottom flask, and 100 μL of PEG-silane (3EO) was added into the reactions under stirring overnight in order to further PEGylate the inside silica surfaces, which had been covered by micelles during the first PEGylation step. This secondary PEGylation was also followed by heating at 80° C. overnight. The day following the heating step, 2 μL APTMS was added into the reactions at 600 r.p.m. at room temperature for PPSMI. For the hollow beads following the PPSMI step, 0.697 μmol free DEAC dye with ester chemistry was added into the solution on the next day in order to click dye to the surface amines, while this additional step was skipped for cages and rings since they were already functionalized with DEAC dye on day one of the particle synthesis. Following the PPSMI step, 0.42 mmol of DFO-NCS chelator was added to the solutions to react with primary amines on the nanoparticle surface via amine-NCS conjugation. After the functionalization with DFO, samples were heated at 80° C. overnight and subsequently purified as described below.

Sample Purification. After syntheses of all inorganic NPs, reaction batches were transferred into dialysis membranes (MWCO 10K) for dialysis in deionized water overnight prior to syringe-filtration (MWCO 0.2 μm, PTFE), after which they were concentrated using spin filters (Vivaspin 20 MWCO 30K) via centrifugation (Eppendorf 5810R) at 4300 r.p.m. for 45 min. Gel permeation chromatography (GPC) was performed on the concentrated samples on a GPC column packed with Superdex 200 prep grade resin using 0.9 wt. % sodium chloride saline as buffer solution, as described previously. NPs were separated from the aggregation products and un-reacted reagents via GPC fractionation, and collected samples were run by GPC again to check for sample purity via the occurrence of a single-peak chromatogram. This resulted in the GPC control runs reported in the data sets comparing different topologies (FIG. 15).

Characterization of Inorganic Nanoparticles. Fluorescence correlation spectroscopy (FCS) measurements were performed to determine size and concentration of different NPs using a home-built setup as described previously. Diffusion coefficients, D, were obtained from measured correlation times, $\tau_D$, using the geometrical factor, $\omega_{xy}$, representing the radius of the FCS focal spot, according to equation (1):

$$D = \frac{\omega_{xy}^2}{4\tau_D}$$

In turn, D was used to determine the (equivalent) hydrodynamic diameter, d, of the particles, i.e. the diameter of a(n) (equivalent) spherical particle derived from the " " Stokes-Einstein relation, equation (2):

$$d = 2\frac{k_B T}{6\pi\eta D}$$

where $k_B$ is Boltzmann constant, T is temperature, and η is the solution viscosity.

A Varian Cary 5000 spectrophotometer was used to measure UV-vis absorption spectra of the samples in order to calculate, together with concentration information from FCS data analysis, the number of dyes and DFO chelators per particle by deconvolution as described previously[14]. Transmission and cryo-electron microscopy (TEM/cryo-EM) were performed on particle samples using a FEI Tecnai T12 Spirit microscope operated at 120 kV. Cryo-EM was performed on cage and ring samples as described previously.

Figure 20:
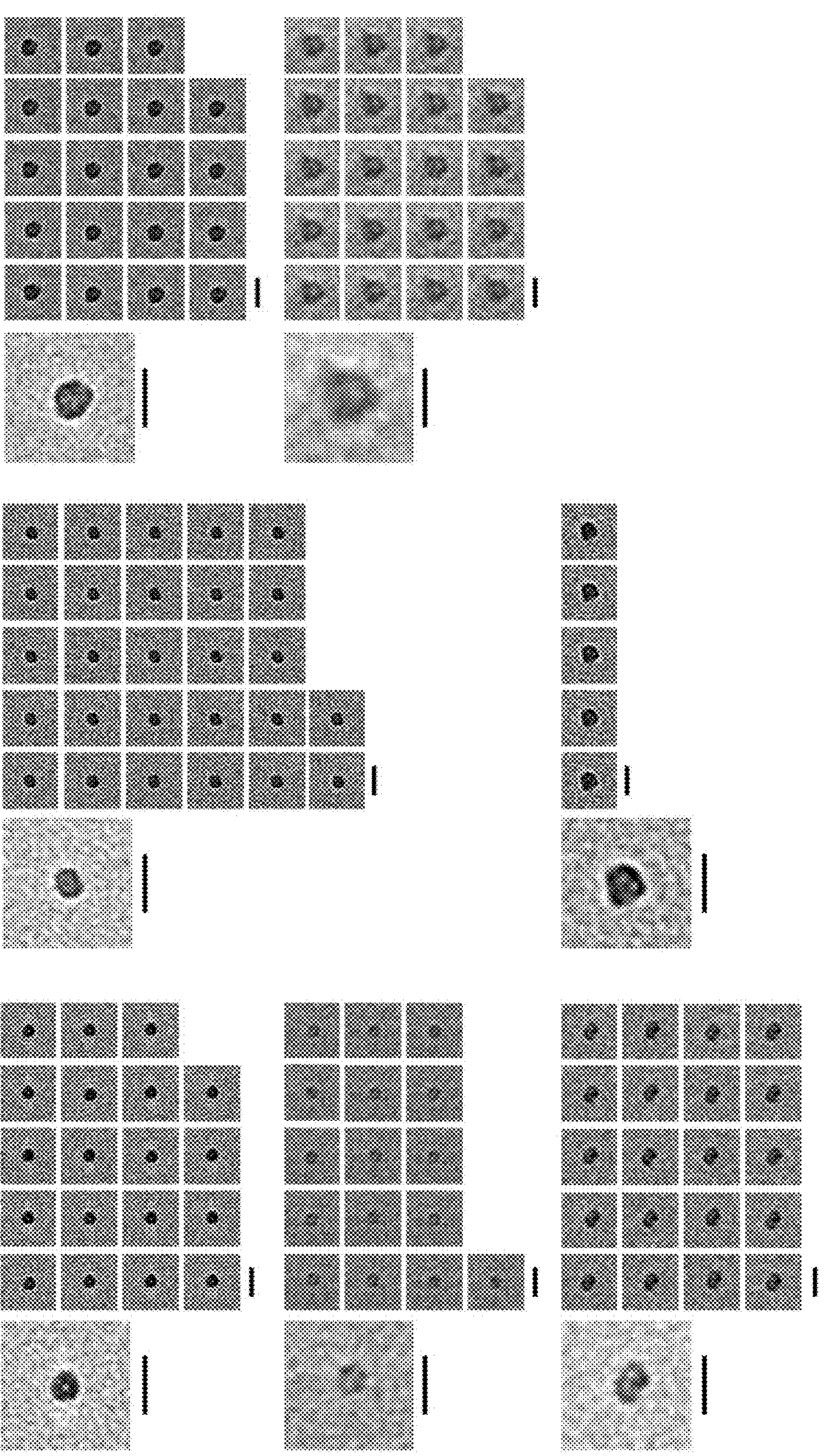
FIG. 20 shows TEM images of intact inorganic NPs in murine biological specimens, i.e., after urinary excretion. (a,b) Averaged and original TEM images (n=7) (Methods) of cages (a) and rings (b) in the urinary samples collected from murine bladders (n=2) at 2 hour post i.v. injection. For each particle, a series of TEM pictures were acquired (insets), and the results were averaged using maximum intensity (left) to improve signal-to-noise ratios. Scale bar is 20 nm.
Figure 20:
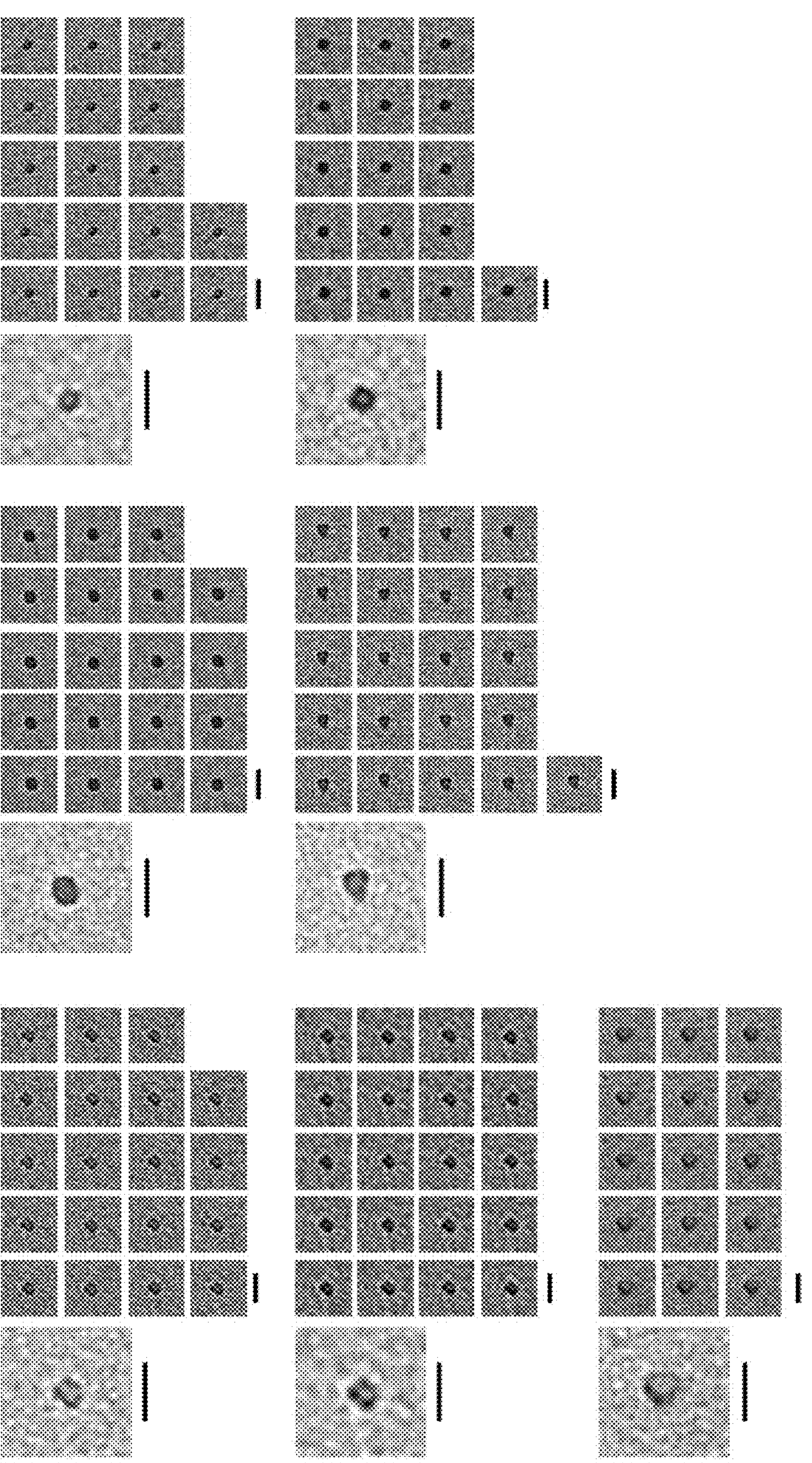
Figure 21:
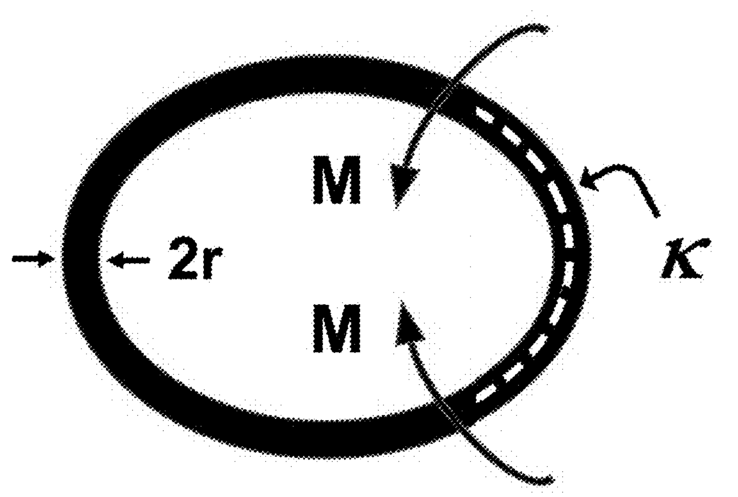
FIG. 21 shows a model calculation showing how ring stiffness depends on the radius, r, of the torus cross section. The left side shows a ring that has been flattened by applying bending moments, M, at one end. The moments, M, lead to a curvature, κ, at the ends of the ring. Approximating this curvature as constant, the relation between M and κ is as shown on the right for simple bending for the case that the ring cross section (i.e., not the radius, R, of the overall ring) is circular with radius r. Since the relation scales linearly with Young's modulus, E, one finds the difference in r that would be needed to reduce the moment, M, by an order of magnitude, i.e. $M_2/M_1=0.1$, at the same curvature, κ, is only a factor of 0.56. That is, the stiffness of the ring can be dramatically reduced by making it thinner without changing its modulus, E. Please note that the relation between moment, M, and curvature, κ, goes as the fourth power of the radius, r. That means, the bending moment is exquisitely sensitive to the thickness of the ring.

To study the integrity of cages and rings after circulation and excretion from mice injected with 250 μL of 15 μM NPs, urine specimens were collected at 2-hour post i.v. injection time point from the mouse bladder while the animal was under anesthesia. After extraction, the urine sample was immediately diluted with deionized water for TEM sample preparation. For samples prepared from urinary specimens, typically more than 15 TEM images were taken per nanoparticle. These images were then averaged to increase the signal-to-noise ratio, as shown in FIG. 20 and described elsewhere.

The zeta-potential of particles with different topologies was measured with a Malvern Zetasizer Nano-ZS operated at neutral pH in deionized water at 20° C. after up-concentrating particle solutions via spin-filters to obtain the desired signal-to-noise ratios as described elsewhere. Each sample was measured three times and results were averaged.

Stability Tests of Inorganic Nanoparticles via FCS. For salt solution stability experiments, 10 μL of a 15 μM nanoparticle suspension was mixed with 1 mL of Hanks'

Balanced Salt Solution (HBSS) in a 10 mL centrifuge tube. The tube was placed in a humidity-controlled cell incubator set to 37° C. with 5% $CO_2$. After 7 days of incubation, 1 μL of nanoparticle-salt solution was diluted into 180 μL of DI water on a 35 mm MatTek No. 1.5 coverslip dish with a 10 mm well (P35G-1.5-10-C). The dish was placed on a 63× water immersion microscope objective and solutions characterized using FCS.

For protein adsorption experiments, a 10 vol. % mouse serum solution was used. To that end, 20 μL of nanoparticle sample at 15 μM concentration was first transferred to a 2 mL screw top centrifuge tube and then diluted with 250 μL of DI water. After adding 30 μL of mouse serum, the centrifuge tube was kept rotating at 37° C. in a cell incubator. For each protein adsorption test, a 40 μL aliquot of the nanoparticle-serum mixture was transferred to a 1.5 mL centrifuge tube followed by the addition of 40 μL chilled acetonitrile (−30° C.) to precipitate the serum proteins. The resulting cloudy mixture was then centrifuged for 20 minutes at 10,000 RCF and 20 μL of the separated supernatant was transferred into a new 1.5 mL centrifuge tube. Using a 35 mm MatTek No. 1.5 coverslip dish with a 10 mm well (P35G-1.5-10-C), 1 μL of nanoparticle-acetonitrile solution was diluted into 180 μL of DI water. The dish was then placed on a 63× water immersion microscope objective and solutions characterized using FCS.

Stability Tests of Inorganic Nanoparticles via HPLC. HPLC Method: All injections were performed with a standardized 60 μL injection volume. The columns used were 50 mm Waters Xbridge Peptide separation columns with 300 Å pore size and 5 μm particle size. Samples were injected onto the column that had been equilibrated with a solvent composition of 95% deionized water with 0.01 volume percent trifluoroacetic acid (TFA) and 5% acetonitrile. After sample injection, a gradient elution profile from the 95:5 composition to a composition of 15% deionized water with 0.01% TFA and 85% acetonitrile was carried out over 8 minutes. The composition was then changed to 95% acetonitrile over 2 minutes. This process was followed by a cleaning and equilibration step before injection of a new sample.

Stability Test: 7.5 μM solutions of inorganic NPs were incubated with 10% by volume serum prepared as follows: First, 150 μL of 15 μM particle solution was aliquoted into a 1.5 mL microcentrifuge tube and diluted with 120 μL of deionized water to bring the total volume of the solution to 270 μL. Finally, 30 μL of either mouse or human serum was added. The tube was closed, para-filmed, and shaken at 300 rpm at 37° C., with 40 μL aliquots taken out at each time point of interest for analysis. For HPLC analysis, 40 μL of cold acetonitrile was added to each aliquot to precipitate serums proteins. Then the aliquots were centrifuged at 10000 rpm for 30 minutes to pellet the precipitated proteins. A 40 μL aliquot of the supernatant was taken and deposited into a Waters Total Recovery HPLC vial. In order to dilute the acetonitrile in the sample vial, an additional 40 μL of deionized water was added to each vial and mixed prior to HPLC injection.

$^{89}Zr$ Radiolabeling of DFO-functionalized Inorganic Nanoparticles. For chelator-based $^{89}Zr$ labeling, 1.5 nmol of DFO-functionalized samples were mixed with 1 mCi of $^{89}Zr$-oxalate in HEPES buffer (pH 8) at 37° C. for 60 min; final labeling pH was kept around 7-7.5. The labeling yield was monitored by radio ITLC. An EDTA challenge process was then introduced to remove any non-specifically bound $^{89}Zr$ to the silica NP surface[16]. As synthesized $^{89}Zr$-DFO-NP samples were then purified by using a PD-10 column with the final radiochemical purity quantified as 100% using ITLC.

Quantitative Renal and Hepatic Clearance Studies of Inorganic Nanoparticles. To study the renal and hepatic clearance of $^{89}Zr$-DFO-functionalized silica nanoparticles with varying topologies, each healthy mouse (6-8 week-old female nude mouse) was injected with about 50 μCi (1.85 MBq) of $^{89}Zr$-DFO-NP, and housed individually in metabolic cages. At varied post i.v. injection time points (i.e., at 4, 24, 48, 72, 120 and 168 h), the cumulative radioactivity in mouse urine and feces were measured separately using a CRC®-55tR Dose Calibrator and presented as % ID (mean±SD). All animal experiments were performed in accordance with protocols approved by the Institutional Animal Care and Use Committee of the Memorial Sloan Kettering Cancer Center (MSKCC) and followed National Institutes of Health (NIH) guidelines for animal welfare.

In-Vivo PET Imaging and Ex-Vivo Biodistribution Studies for Inorganic Nanoparticles. For PET imaging, mice were i.v. injected with ~300 μCi (11.1 MBq) $^{89}Zr$-DFO-NP. PET imaging was performed in a small-animal PET scanner (Focus 120 microPET; Concorde Microsystems) at 1, 24, 48, 72 h and 168 h (one week) post i.v. injection. Image reconstruction and region-of-interest (ROI) analysis of the PET data were performed using IRW software, with results presented as the percentage of the injected dose per gram of tissue (% ID/g). On day 7, post i.v. injection, accumulated activity in major organs was assayed by an Automatic Wizard$^2$ γ-Counter (PerkinElmer), and presented as % ID/g (mean±SD).

Biostatistics. Biodistribution and clearance profiles were compared across sizes, topologies, and organs using a linear model with interactions. Significance was evaluated using a Wald test and maximum likelihood estimates.

Mechanical model for particle deformation. The glomerular capillary pressure, $P_{gc}$, has been measured in rodents (rats) and is 88 mm Hg=11,732 Pa, i.e., around 10 kPa[30]. Arguments supporting the hypothesis that this is enough to deform the nanoparticles, in particular those with ring and cage topologies, follow the subsequent analysis: the silica structure of rings and cages (and, it is suspected, even of hollow spheres), overall, is not homogeneous, but rather consists of silica clusters of around 2 nm in diameter, that are subsequently connected via additional Si—O—Si bond formation (vide supra). Careful TEM studies, e.g., of the rings, suggest that this results in what could be described as a "pearl-chain" type structure, as opposed to a homogeneous torus shape (see also TEM images in FIG. 11).

Within the thin links or bridges between individual silica clusters, the condensation degree of silica is expected to be even lower than that of regular C dots, most likely characterized predominantly by Q2 groups rather than Q3 groups (i.e., each silicon atom only has two rather than three bridging oxygens to other Si atoms, reflecting linear chain behavior). This suggests that the thin bridges have more the character of a cross-linked polysiloxane rather than that of highly cross-linked silica characterized predominantly by Q4 groups, i.e., they are compliant links. A typical representative of a polysiloxane is poly(dimethyl-siloxane) (PDMS). Crosslinked PDMS rubber has Young's modulus somewhere between 360-870 kPa; significantly more compliant than Q4-dominated silica, for which E≈72 GPa. The modulus of PDMS would still be one to two orders of magnitude too high, however, to explain particle deformation during renal excretion, if the rings were considered to have a uniform cross section of 2 nm. In contrast, in a pearl-chain, bending deformation is concentrated in the thin links rather than the pearls. As demonstrated by a model calculation (FIG. 21), the bending moment, M, is exquisitely sensitive to the diameter of these links ($M \propto r^4$). Reducing the diameter of the links to about 50%, 30%, or 20% of the regular diameter of the ring torus decreases the bending modulus by 1, 2, or 3 orders of magnitude, respectively. Such diameters would still allow multiple linear chains to connect two neighboring clusters, enough to provide stability and elastic compliance. In summary, in the "pearl-chain" picture, the bending modulus of the rings is substantially reduced by having thin and compliant links. Since the formation mechanism of rings and cages (as well as hollow spheres) is similar, it is expected that such thin and compliant links between silica clusters facilitate their deformation during the glomerular filtration process responsible for the observed renal clearance of these particles.

Although the present disclosure has been described with respect to one or more particular example(s), it will be understood that other examples of the present disclosure may be made without departing from the scope of the present disclosure.

The invention claimed is:

1. A silica nanoring comprising a silica matrix, defining a single aperture and comprising an outer surface and an inner surface, wherein at least a portion of or substantially all of the outer surface, and optionally, at least a portion of or substantially all of the inner surface, or all of the surfaces of the silica nanoring are functionalized with polyethylene glycol (PEG) groups, functionalized PEG groups, or a combination thereof, and at least a portion of or all the silica matrix of the silica nanoring is microporous, wherein the silica nanoring has an outer diameter or 5 nm to 20 nm and/or the single aperture of the silica nanoring has an inside diameter of 3 nm to 13 nm.

2. The silica nanoring of claim 1, wherein the at least a portion or substantially all or all of the outer surface and/or at least a portion or substantially all or all of the inner surface is functionalized with one or more display group(s) chosen from peptide groups, nucleic acid groups, antibody groups, antibody fragment groups, dye groups, metal chelating groups, radiolabel groups, radiotherapeutics, drug groups, drug-linker groups, sensor groups, functional groups, and combinations thereof.

3. A composition comprising a plurality of silica nanorings of claim 1.

4. The composition of claim 3, the composition further comprising one or more pharmaceutical carrier(s).

5. A method of making silica nanorings of claim 1 comprising:

forming a reaction mixture comprising:

one or more silica precursor(s);

one or more surfactant(s); and one or more pore expander(s);

holding the reaction mixture at a time and temperature, whereby the silica nanorings are formed; and adding a PEG-silane, a PEG-silane conjugate comprising a display group, or a combination thereof to the reaction mixture, wherein the silica nanorings of claim 1 are formed.

6. The method of claim 5, further comprising functionalization of at least a portion of an outer surface and/or at least a portion of an inner surface of the silica nanorings with one or more display group(s).

7. The method of claim 5, wherein the silica nanorings of claim 1 comprise an interior, the method further comprising removing substantially all or all of the one or more surfactant(s) and/or the one or more pore expander(s) from the interior of the silica nanorings.

8. The method of claim 5, wherein before or after the PEG-silane is added, adding a PEG-silane conjugate comprising a display group is added at room temperature to the reaction mixture, holding the reaction mixture at a second time and second temperature, and subsequently heating the reaction mixture at a third time and third temperature, whereby silica nanorings surface functionalized with PEG groups comprising a display group are formed.

9. The method of claim 5, wherein at least a portion of or all of the PEG-silane has a reactive group on a terminus of the PEG group opposite the terminus conjugated to a silane group of the PEG-silane conjugate and after formation of the silica nanoring surface functionalized with PEG groups having a reactive group, and, optionally, PEG groups, are reacted with a second display group functionalized with a second reactive group thereby forming silica nanorings surface functionalized with PEG groups functionalized with a second display group and, optionally, PEG groups.

10. The method of claim 5, wherein the reaction mixture further comprises water and a pH, and the pH of the reaction mixture is 6-9.

11. A silica nanoring comprising a silica matrix, a hydrodynamic size of 7 nm to 15 nm, a single pore comprising a diameter of 4 nm to 8 nm, and an outer surface and an inner surface, wherein at least a portion of or substantially all of the outer surface, and optionally, at least a portion of or substantially all of the inner surface, or all of the surfaces of the silica nanoring are functionalized with polyethylene glycol (PEG) groups.

12. The silica nanoring of claim 11, wherein the at least a portion of or all of the outer surface is functionalized with PEG groups, independently at each occurrence comprising 6, 7, 8, or 9 ethyleneoxide groups, and, optionally, one or more drug group(s), and at least a portion of or all of the inner surface is functionalized with PEG groups, independently at each occurrence comprising 2, 3, or 4 ethylene oxide groups, and, optionally, one or more drug groups(s), and the silica matrix of the nanoring comprises one or more fluorescent group(s) covalently bound to the silica matrix.

13. The silica nanoring of claim 11, wherein the at least a portion or substantially all or all of the outer surface and/or at least a portion or substantially all or all of the inner surface is functionalized with one or more display group(s) chosen from peptide groups, nucleic acid groups, antibody groups, antibody fragment groups, dye groups, metal chelating groups, radiolabel groups, radiotherapeutics, drug groups, drug-linker groups, sensor groups, functional groups, and combinations thereof.

14. The silica nanoring of claim 11, wherein the silica nanoring is a diagnostic agent, drug delivery agent, a therapeutic agent, a theranostic agent, or a combination thereof.

15. The silica nanoring of claim 1, wherein the single aperture comprises a diameter of 4 nm to 8 nm.

16. The silica nanoring of claim 1, wherein the silica nanoring comprises more than one display group and at least a portion of the display groups are structurally distinct.

17. The silica nanoring of claim 1, wherein the at least a portion of or all of the outer surface is functionalized with PEG groups, independently at each occurrence comprising 6, 7, 8, or 9 ethyleneoxide groups, and, optionally, one or more drug group(s), and at least a portion of or all of the inner surface is functionalized with PEG groups, independently at each occurrence comprising 2, 3, or 4 ethylene oxide groups, and, optionally, one or more drug groups(s), and the silica matrix of the nanoring comprises one or more fluorescent group(s) covalently bound to the silica matrix.

18. The silica nanoring of claim 1, wherein the silica nanoring is a diagnostic agent, drug delivery agent, a therapeutic agent, a theranostic agent, or a combination thereof.

19. The method of claim 5, wherein the one or more surfactant(s) is/are chosen from $C_{10}$ to $C_{18}$ alkyltrimethylammonium halides, sodium dodecyl sulfate (SDS), N-myristoyl-L-glutamic acid (C14GluA), and combinations thereof, and/or the one or more pore expander(s) is/are chosen from trialkylated benzene, polymer monomers, hydrophobic solvents, cycloalkanes, benzene, alkylated benzene, chlorinated alkanes, and combinations thereof.

20. The method of claim 5, wherein the one or more silica precursor(s) is/are chosen from tetraalkoxysilanes, alkyltrialkoxysilanes, functionalized silica precursors, and combinations thereof.

21. The method of claim 5, wherein reaction mixture comprises a molar ratio of moles of the one or more surfactant(s) to moles of the one or more pore expander(s) and the molar ratio is 1:2 to 1:10.

22. The method of claim 5, wherein at least a portion of or all of the one or more of the silica precursor(s) comprises one or more display group(s).

23. A silica nanoring comprising a silica matrix, defining a single aperture and comprising an outer surface and an inner surface, wherein at least a portion of or substantially all of the outer surface, and optionally, at least a portion of or substantially all of the inner surface, or all of the surfaces of the silica nanoring are functionalized with polyethylene glycol (PEG) groups, functionalized PEG groups, or a combination thereof, and at least a portion of or all the silica matrix of the silica nanoring is microporous, wherein the at least a portion of or all of the outer surface is functionalized with PEG groups, independently at each occurrence, comprising 6, 7, 8, or 9 ethylene oxide groups, and, optionally, one or more drug group(s), and at least a portion of or all of the inner surface is functionalized with PEG groups, independently at each occurrence comprising 2, 3, or 4 ethylene oxide groups, and, optionally, one or more drug groups(s), and the silica matrix of the nanoring comprises one or more fluorescent group(s) covalently bound to the silica matrix.

* * * * *